US007880008B2

(12) United States Patent
Wilson et al.

(10) Patent No.: US 7,880,008 B2
(45) Date of Patent: Feb. 1, 2011

(54) HETEROCYCLES USEFUL AS MODULATORS OF ION CHANNELS

(75) Inventors: Dean Wilson, San Diego, CA (US); Andreas Termin, Encinitas, CA (US); Lev T. D. Fanning, San Marcos, CA (US); Paul Krenitsky, San Diego, CA (US); Pramod Joshi, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 148 days.

(21) Appl. No.: 11/441,487

(22) Filed: May 26, 2006

(65) Prior Publication Data

US 2008/0255147 A1   Oct. 16, 2008

Related U.S. Application Data

(60) Provisional application No. 60/685,971, filed on May 31, 2005.

(51) Int. Cl.
  A61K 31/496 (2006.01)
  A61K 31/454 (2006.01)
  C07D 417/04 (2006.01)
  C07D 417/14 (2006.01)
  A61P 25/00 (2006.01)

(52) U.S. Cl. .................. 546/209; 514/326; 514/254.02; 514/254.03

(58) Field of Classification Search ........................ None
See application file for complete search history.

(56) References Cited

U.S. PATENT DOCUMENTS

| | | | |
|---|---|---|---|
| 3,040,047 A | 6/1962 | Sirakawa | |
| 3,850,928 A | 11/1974 | Kim et al. | |
| 5,051,347 A | 9/1991 | Uchida et al. | |
| 5,342,851 A | 8/1994 | Sanfilippo et al. | |
| 6,380,230 B1 | 4/2002 | Brodin et al. | |
| 2002/0183335 A1 | 12/2002 | Dextraze et al. | |
| 2003/0229068 A1 | 12/2003 | Huang et al. | |
| 2004/0157883 A1 | 8/2004 | Chen et al. | |
| 2005/0049247 A1 | 3/2005 | Wilson et al. | |
| 2005/0090533 A1 | 4/2005 | Hoffmann et al. | |
| 2005/0227989 A1 | 10/2005 | Wang et al. | |
| 2007/0082889 A1 | 4/2007 | Wilson et al. | |
| 2007/0093454 A1 | 4/2007 | Wilson et al. | |
| 2008/0090837 A1 | 4/2008 | Termin et al. | |

FOREIGN PATENT DOCUMENTS

| DE | 2341925 A | 3/1975 |
|---|---|---|
| EP | 0257102 A | 3/1988 |
| EP | 0 320 778 | 6/1989 |
| EP | 0410225 A1 | 12/1990 |
| EP | 0675118 | 10/1995 |
| GB | 901749 A | 7/1962 |
| GB | 1512101 | 5/1978 |
| WO | 9915525 | 4/1999 |
| WO | 00/53572 | 9/2000 |
| WO | 00/59510 | 10/2000 |
| WO | WO 02/02539 A1 * | 1/2002 |
| WO | 02/088101 | 11/2002 |
| WO | 03/002062 | 1/2003 |
| WO | 03044019 A1 | 5/2003 |
| WO | 2004/094395 | 11/2004 |
| WO | 2005/014558 | 2/2005 |
| WO | 2005/021523 | 3/2005 |
| WO | 2005019200 * | 3/2005 |
| WO | 2005/058876 | 6/2005 |
| WO | 2005/099673 | 10/2005 |
| WO | 2005/110416 | 11/2005 |
| WO | 2005/117909 | 12/2005 |
| WO | 2006/047277 | 5/2006 |
| WO | 2006/065600 | 6/2006 |
| WO | 2006/065706 | 6/2006 |
| WO | 2006/071762 | 7/2006 |
| WO | 2006124865 | 11/2006 |
| WO | 03101985 A1 | 5/2009 |

OTHER PUBLICATIONS

International Search Report of International Application No. PCT/US2006/017046.
International Search Report of International Application No. PCT/US2004/021440.
International Search Report of International Application No. PCT/US2006/017214.
International Search Report of International Application No. PCT/US2006/018871.
Database Chemcats Chemical Abstracts Service, Columbus, Ohio, US' XP002397389 retrieved from STN Accession No. 2004:1976992, 2004:1976991, 2004:1976990, 2004:1976987 & "ChemDiv, Inc. Product Library" Apr. 25, 2003 (Mar. 3, 2003).
Database Chemcats Chemical Abstracts Service, Columbus, Ohio, US' XP002397395 retrieved from STN Accessopm Mp/ 2005:432837, 2005:432417, 2005:431047, 2005:430868, 2005:430523, and 2005: 421395 & "ChemBridge Screening Library" Jan. 12, 2005.
Juby et al. "4-Anilinopyrimidine-5-carboxylic Acids and Esters with Anti-Inflammatory and Analgetic Properties" J. Med. Chem., vol. 10, pp. 954-957, 1967.

(Continued)

Primary Examiner—Brian-Yong S Kwon
Assistant Examiner—Bong-Sook Baek
(74) Attorney, Agent, or Firm—Michael C. Badia

(57) ABSTRACT

The present invention relates to compounds useful as inhibitors of ion channels. The invention also provides pharmaceutically acceptable compositions comprising the compounds of the invention and methods of using the compositions in the treatment of various disorders.

11 Claims, No Drawings

OTHER PUBLICATIONS

Kim et al. "Reactions of 4-(2-Hydroxyethylamino)-2-phenyl-5-pyrimidinecarboxylic Acid with Acetic Anhydride. Syntheses of 8,9-Dihydro-6a-methyl-2-phenyl-5H,6aH-oxazolo-[2,3-b]pyrimido[4,5-d][1,3]oxazin-5-one and 8,9-Dihydro-8,8-dimethyl-2-phenyl-5H-oxazolo[2',3':6,1]pyrido[2,3-d]pyrimidin-5-one," J. Org. Chem. vol. 37 No. 18, pp. 2854-2857 (1972).

Kim et al. "Pyrimido[4,5-e][1,4]diazepin-5-ones and 4,4-Ethylenediaminobis(2-phenyl-pyrimidine-5-carboxylic acid) Diethyl Esters" J. Med. Chem., vol. 12, pp. 1121-1122, 1969.

Koppel et al. "Pyrimidines. X. (Antibiotics. II) Synthesis of Bacimethrin, 2-Methoxy Analog of Thiamine, and Related Alkoxypyrimidines" J. Org. Chem., vol. 27, pp. 3614-3617, 1962.

Saad et al. "Functionalization and Heteroannelation of Ethyl 2-(4'-chlorophenyl)-4-mercapto-6-methylpyrimidine-5-caboxylate", Bull. Korean Chem. Soc., vol. 22, No. 3, pp. 311-314, 2001.

Hainsworth et al. "Effects of Extracellular pH on the Interaction of Sipatrigine and Lamotrigine with High-voltage-activated (HVA) Calcium Channels in Dissociated Neurones of Rat Cortex" Neuropharmacology, vol. 40, pp. 784-791, 2001.

International Search Report of International Application No. PTC/US2006/020521.

Office Action mailed Aug. 22, 2007 for U.S. Appl. No. 10/884,865.

Office Action mailed Sep. 16, 2008 for U.S. Appl. No. 11/418,163.

Office Action mailed Jul. 6, 2007 for U.S. Appl. No. 11/418,163.

Mrs. Anjali Milind Rahatgaonkar, Synthesis and Biological Evaluation of 2-Imino-Benzal-4-(2'-Hydroxy Aryl)-Thiazole]-4-Aryl-2-Azetidinones. Asian Journal of Chemistry (1999), 1427-1430, vol. 11 No. 4, Institute of Science, Nagpur 440 001, India.

R H Khan et al., Synthesis and antimicrobial activity of 3-(4'-aryl-2'thiazolyl)-2,4-dioxo-1,2,3,4-tetrahydroquinazolines and 2-(4'-aryl-2'-thiazolylamino)-4-oxo-4H-3,1-benzoxazinesfrom methyl N-(4-arul-2-thiazolyl)dithiocarbamates. Indian Journal of Chemistry (1993) 595-598, vol. 32B, Organic Chemistry Division Regional Research Laboratory, Jorhat 785 006.

Hui-Ling Liu et al., Synthesis and Fungicidal Activity of 2-Imino-3-(4-arylthiazol-2-yl)-thiazolidin-4-ones and Their 5-Arylidene Derivatives. Molecules (2000) 1055-1061, 5, MDPI.

S. Kumar et al., Synthesis and Biological Evaluation of Some New 2-Aryl/Substituted Aryl-6, 8-Substituted Quinazol-4 (3H)-Ones, Part-2. Indian Journal of Heterocyclic Chemistry (1997) 51-54, vol. 7, Chemistry Department, Ranchi College, Ranchi University, Ranchi-834-008.

PH Patel et al., Synthesis and Antimicrobial Activity of 4-Thiazolidinone and Imidazolinone Derivatives Bearing 2-Aminothiazole Moiety. Indian Journal of Heterocyclic Chemistry (1997) 73-76, vol. 7, Department of Chemistry, Saurashtra University, Rajkot-360 005.

* cited by examiner

HETEROCYCLES USEFUL AS MODULATORS OF ION CHANNELS

CROSS-REFERENCE TO RELATED APPLICATIONS

This application claims the benefit under 35 U.S.C. §119 of U.S. Provisional application Ser. No. 60/685,971 filed May 31, 2005, the entire contents of which is incorporated herein by reference.

TECHNICAL FIELD OF THE INVENTION

The present invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12(1): 85-91)), pain (ee, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). As shown in Table 1, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

TABLE 1

(Abbreviations: CNS = central nervous system, PNS = peripheral nervous sytem, DRG = dorsal root ganglion, TG = Trigeminal ganglion):

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrhythmia, long QT |
| NaV1.6 | CNS widespread, most abuntant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87(1): 7-17.) bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8.), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94.). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (ee, Akopian, A. N., V. Souslova, et al. (1999) "The tetrodotoxin-resistant sodium channel SNS has a specialized function in pain pathways" *Nat Neurosci* 2(6): 541-8). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62). The primary role of these neurons is the detection and transmission of nociceptive stimuli. Antisense and immunohistochemical evidence also supports a role for NaV1.8 in neuropathic pain (ee Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain." *Pain* 83(3): 591-600.) The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See, Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21(16): 5952-61). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." *J Neurosci* 22(17): 7425-33). It has a slow rate of inactivation and left-shifted voltage dependence for activation (See, Dib-Hajj, S., J. A. Black, et al. (2002) "NaN/Nav1.9: a sodium channel with unique properties" *Trends Neurosci* 25(5): 253-9). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir (Wien)* 144(8): 803-10; discussion 810). NaV1.6 and NaV1.7 are also expressed in dorsal root ganglion neurons and contribute to the small TTX sensitive component seen in these cells. NaV1.7 in particular my therefore be a potential pain target in addition to it's role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14(6): 1084-90).

NaV1.1 (See, Sugawara, T., E. Mazaki-Miyazaki, et al. (2001) "Nav1.1 mutations cause febrile seizures associated with afebrile partial seizures." *Neurology* 57(4): 703-5.) and NaV1.2 (See, Sugawara, T., Y. Tsurubuchi, et al. (2001) "A missense mutation of the $Na^+$ channel alpha II subunit gene Na(v)1.2 in a patient with febrile and afebrile seizures causes channel dysfunction" *Proc Natl Acad Sci USA* 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99(7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91.); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant $Na^+$ currents and inflammatory hyperalgesia." *Proc Natl Acad Sci USA* 96(14): 7645-9), and neuropathic pain (ee Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human $Na^+$ channels" *Circ Res* 79(1): 103-8, and Wang, D. W., K. Yazawa, et al. (1997) "Pharmacological targeting of long QT mutant sodium channels" *J Clin Invest* 99(7): 1714-20); neuroprotection (ee Taylor, C. P. and L. S, Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found Symp* 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48(3):382-3; femur cancer pain (see, Kohase, H., et al., Acta Anaesthesiol Scand. 2004; 48(3):382-3); non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1):11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); Neuropathic low back pain (see, Hines, R., et al., Pain Med. 2002; 3(4):361-5; Massie, J. B., et al., J Neurosci Methods. 2004; 137(2):283-9; neuropathic low back pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K A et al., Muscle Nerve. 2001; 24(1):37-46); fibromyalgia (see, Bennet & Tai, Int J Clin Pharmacol Res. 1995; 15(3):115-9); temporomandibular joint pain (see, Ime H, Ren K, Brain Res Mol Brain Res. 1999; 67(1):87-97); chronic visceral pain, including, abdominal (see, Al-Chaer, E. D., et al., Gastroenterology. 2000; 119(5):1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84); IBS pain (see, Verne, G. N., et al., Pain. 2003; 105(1-2):223-30; La J H et al., World Gastroenterol. 2003; 9(12):2791-5); chronic headache pain (see, Willimas & Stark, Cephalalgia. 2003; 23(10):963-71); migraine (see, Yamamura, H., et al., J Neurophysiol. 1999; 81(2):479-93); tension headache, including, cluster headaches (see, Costa, A., et al., Cephalalgia. 2000; 20(2):85-91); chronic neuropathic pain, including, post-herpetic neuralgia (see, Attal, N., et al., Neurology. 2004; 62(2):218-25; Kim & Chung 1992, Pain 50:355); diabetic neuropathy (see, Beidoun A et al., Clin J Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E K et al., Pain. 2004; 107(1-2):147-58; Oh, S. B., et al., J. Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol. Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1):119-27); radiculopathy (see, Devers & Galer, (see, Clin J Pain. 2000; 16(3):205-8; Hayashi N et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J Pain. 2000; 16(3):205-8); central pain (Cahana, A., et al., Anesth Analg. 2004; 98(6):1581-4), spinal cord injury pain (see, Hains, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos D et al., J Pain. 2004; 5(3 Suppl 2):S1); phanton pain (see, Weber, W. E., Ned Tijdschr Geneeskd. 2001; 145(17):813-7; Levitt & Heyback, Pain. 1981; 10(1): 67-73); intractable pain (see, Yokoyama, M., et al., Can J Anaesth. 2002; 49(8):810-3); acute pain, acute post-operative pain (see, Koppert, W., et al., Anesth Analg. 2004; 98(4): 1050-5; Brennan, T. J., et al., Pain. 1996; 64(3):493-501); acute musculoskeletal pain; joint pain (see, Gotoh, S., et al., Ann Rheum Dis. 1993; 52(11):817-22); mechanical low back pain (see, Kehl, L. J., et al., Pain. 2000; 85(3):333-43); neck pain; tendonitis; injury/exercise pain (see, Sesay, M., et al., Can J Anaesth. 2002; 49(2):137-43); acute visceral pain, including, abdominal pain; pyelonephritis; appendicitis; cholecystitis; intestinal obstruction; hernias; etc (see, Giambernardino, M. A., et al., Pain. 1995; 61(3):459-69); chest pain, including, cardiac Pain (see, Vergona, R. A., et al., Life Sci. 1984; 35(18):1877-84); pelvic pain, renal colic pain, acute obstetric pain, including, labor pain (see, Segal, S., et al., Anesth Analg. 1998; 87(4):864-9); cesarean section pain; acute inflammatory, burn and trauma pain; acute intermittent pain, including, endometriosis (see, Cason, A. M., et al., Horm Behav. 2003; 44(2):123-31); acute herpes zoster pain; sickle cell anemia; acute pancreatitis (see, Toma, H; Gastroenterology. 2000; 119(5):1373-81); breakthrough pain; orofacial pain, including, sinusitis pain, dental pain (see, Nusstein, J., et al., J Endod. 1998; 24(7):487-91; Chidiac, J. J., et al., Eur J Pain. 2002; 6(1):55-67); multiple sclerosis (MS) pain (see, Sakurai & Kanazawa, J Neurol Sci. 1999; 162(2):162-8; Waxman, Stephen G. et al, PNAS 2000; 97(21): 11598-602); pain in depression (see, Greene B, Curr Med Res Opin. 2003; 19(4):272-7); leprosy pain; behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130(4):429-33); Fabry's disease pain (see, Germain, D. P., J Soc Biol. 2002; 196(2):183-90);

Bladder and urogenital disease, including, urinary incontinence (see, Berggren, T., et al., J Urol. 1993; 150(5 Pt 1):1540-3); hyperactivity bladder (see, Chuang, Y. C., et al., Urology. 2003; 61(3):664-70); painful bladder syndrome (see, Yoshimura, N., et al., J. Neurosci. 2001; 21(21):8690-6); interstitial cyctitis (IC) (see, Giannakopoulos & Campilomatos, Arch Ital Urol Nefrol Androl. 1992; 64(4):337-9; Boucher, M., et al., J Urol. 2000; 164(1):203-8); and prostatitis (see, Mayersak, J. S., Int Surg. 1998; 83(4):347-9; Keith, I. M., et al., J Urol. 2001; 166(1):323-8).

Voltage-gated calcium channels are membrane-spanning, multi-subunit proteins that open in response to membrane depolarization, allowing Ca entry from the extracellular milieu. Calcium channels were initially classified based on the time and voltage-dependence of channel opening and on the sensitivity to pharmacological block. The categories were low-voltage activated (primarily T-type) and high-voltage activated (L, N, P, Q or R-type). This classification scheme was replaced by a nomenclature based upon the molecular subunit composition, as summarized in Table B (Hockerman G H, Peterson B Z, Johnson B D, Catterall W A. 1997. *Annu Rev Pharmacol Toxicol* 37: 361-96; Striessnig J. 1999. *Cell Physiol Biochem* 9: 242-69). There are four primary subunit types that make up calcium channels—$\alpha_1$, $\alpha_2\delta$, $\beta$ and $\gamma$ (See, e.g., De Waard et al. Structural and functional diversity of voltage-activated calcium channels. In Ion Channels, (ed. T. Narahashi) 41-87, (Plenum Press, New York, 1996)). The $\alpha_1$ subunit is the primary determinant of the pharmacological properties and contains the channel pore and voltage sensor (Hockerman et al., 1997; Striessnig, 1999). Ten isoforms of the $\alpha_1$ subunit are known, as indicated in Table I below. The $\alpha_2\delta$ subunit consists of two disulfide linked subunits, $\alpha_2$, which is primarily extracellular and a transmembrane $\delta$ subunit. Four isoforms of $\alpha_2\delta$ are known, $\alpha_2\delta$-1, $\alpha_2\delta$-2, $\alpha_2\delta$-3 and $\alpha_2\delta$-4. The $\beta$ subunit is a non-glycosylated cytoplasmic protein that binds to the $\alpha_1$ subunit. Four isoforms are known, termed $\beta_1$ to $\beta_4$. The $\gamma$ subunit is a transmembrane protein that has been biochemically isolated as a component of $Ca_v1$ and $Ca_v2$ channels. At least 8 isoforms are known ($\gamma_1$ to $\gamma_8$) [Kang M G, Campbell K P. 2003. *J Biol Chem* 278: 21315-8]. The nomenclature for voltage-gated calcium channels is based upon the content of the $\alpha_1$ subunit, as indicated in Table I. Each type of $\alpha_1$ subunit can associate with a variety of $\beta$, $\alpha_2\delta$ or $\gamma$ subunits, so that each $Ca_v$ type corresponds to many different combinations of subunits.

TABLE B

| Cav Nomenclature | $\alpha_1$ subunit | Pharmacological name |
| --- | --- | --- |
| $Ca_v1.1$ | $\alpha_{1S}$ | L-type |
| $Ca_v1.2$ | $\alpha_{1C}$ | L-type |
| $Ca_v1.3$ | $\alpha_{1D}$ | L-type |
| $Ca_v1.4$ | $\alpha_{1F}$ | |
| $Ca_v2.1$ | $\alpha_{1A}$ | P- or Q-type |
| $Ca_v2.2$ | $\alpha_{1B}$ | N-type |
| $Ca_v2.3$ | $\alpha_{1E}$ | R-type |
| $Ca_v3.1$ | $\alpha_{1G}$ | T-type |
| $Ca_v3.2$ | $\alpha_{1H}$ | T-type |
| $Ca_v3.3$ | $\alpha_{1I}$ | T-type |

$Ca_v2$ currents are found almost exclusively in the central and peripheral nervous system and in neuroendocrine cells and constitute the predominant forms of presynaptic voltage-gated calcium current. Presynaptic action potentials cause channel opening and neurotransmitter release is steeply dependent upon the subsequent calcium entry. Thus, $Ca_v2$ channels play a central role in mediating neurotransmitter release.

$Ca_v2.1$ and $Ca_v2.2$ contain high affinity binding sites for the peptide toxins ω-conotoxin-MVIIC and ω-conotoxin-GVIA, respectively, and these peptides have been used to determine the distribution and function of each channel type. $Ca_v2.2$ is highly expressed at the presynaptic nerve terminals of neurons from the dorsal root ganglion and neurons of lamina I and II of the dorsal horn (Westenbroek R E, Hoskins L, Catterall W A. 1998. *J Neurosci* 18: 6319-30; Cizkova D, Marsala J, Lukacova N, Marsala M, Jergova S, et al. 2002. *Exp Brain Res* 147: 456-63). $Ca_v2.2$ channels are also found in presynaptic terminals between second and third order interneurons in the spinal cord. Both sites of neurotransmission are very important in relaying pain information to the brain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain on the other had may last for much longer periods of time and it's intensity is more graded. Inflammation may occur for many reasons including tissue damage, autoimmune response, and pathogen invasion. Inflammatory pain is mediated by an "inflammatory soup" that consists of substance P, histamines, acid, prostaglandin, bradykinin, CGRP, cytokines, ATP, and neurotransmitter release. The third class of pain is neuropathic and involves nerve damage that results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX2 inhibitors, opioids, tricyclic antidepressants, and anticonvulsants. Neuropathic pain has been particularly difficult to treat as it does not respond well to opioids until high doses are reached. Gabapentin is currently the favored therapeutic for the treatment of neuropathic pain although it works in only 60% of patients where it shows modest efficacy. The drug is however very safe and side effects are generally tolerable although sedation is an issue at higher doses.

Validation of Cav2.2 as a target for the treatment of neuropathic pain is provided by studies with ziconotide (also known as ω-conotoxin-MVIIA), a selective peptide blocker of this channel (Bowersox S S, Gadbois T, Singh T, Pettus M, Wang Y X, Luther R R. 1996. *J Pharmacol Exp Ther* 279: 1243-9; Jain K K. 2000. *Exp. Opin. Invest. Drugs* 9: 2403-10; Vanegas H, Schaible H. 2000. *Pain* 85: 9-18). In man, intrathecal infusion of Ziconotide is effective for the treatment of intractable pain, cancer pain, opioid resistant pain, and neuropathic pain. The toxin has an 85% success rate for the treatment of pain in humans with a greater potency than morphine. An orally available antagonist of $Ca_v2.2$ should have similar efficacy without the need for intrathecal infusion. $Ca_v2.1$ and $Ca_v2.3$ are also in neurons of nociceptive pathways and antagonists of these channels could be used to treat pain.

Antagonists of $Ca_v2.1$, $Ca_v2.2$ or $Ca_v2.3$ should also be useful for treating other pathologies of the central nervous system that apparently involve excessive calcium entry. Cerebral ischaemia and stroke are associated with excessive calcium entry due to depolarization of neurons. The $Ca_v2.2$ antagonist ziconotide is effective in reducing infarct size in a focal ischemia model using laboratory animals, suggesting that $Ca_v2.2$ antagonists could be used for the treatment of stroke. Likewise, reducing excessive calcium influx into neurons may be useful for the treatment of epilepsy, traumatic brain injury, Alzheimer's disease, multi-infarct dementia and other classes of dementia, amyotrophic lateral sclerosis, amnesia, or neuronal damage caused by poison or other toxic substances.

$Ca_v2.2$ also mediates release of neurotransmitters from neurons of the sympathetic nervous system and antagonists could be used to treat cardiovascular diseases such as hypertension, cardiac arrhythmia, angina pectoris, myocardial infarction, and congestive heart failure.

Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel and Ca channel antagonists, preferably those with higher potency and fewer side effects. Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel and Ca channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels and/or calcium channels. These are compounds of formula I:

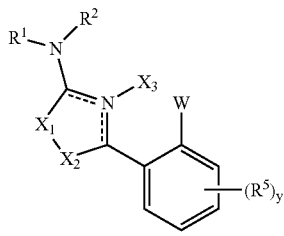

or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

I. General Description of Compounds of the Invention

In one embodiment, the present invention provides compounds of formula I:

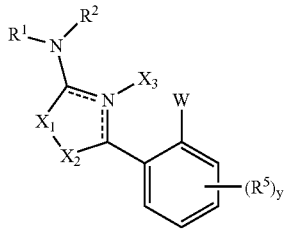

or a pharmaceutically acceptable salt thereof, wherein:

$\rightleftharpoons$ is a single or double bond;

$X_1$ and $X_2$ each is independently $=CR^3-$, $=N-$, $-O-$, $-S-$, or $-NR^3-$;

$X_3$ is $R^3$ or a lone pair of electrons;

provided that $X_1$, $X_2$, and $N(X_3)$, taken together with the intervening carbon atoms form a 5-membered heteroaryl ring;

W is halo, OR', SR', N(R')$_2$, NRC(O)R', S(O)$_2$N(R')$_2$, OC(O)R', OC(O)N(R')$_2$, NR(S(O)$_2$R', OP(O)(OR')$_2$, OP(O)$_2$OR', OP(O)(R')$_2$, CHF$_2$, CH$_2$F, or CF$_3$;

$R^1$ and $R^2$, taken together with the nitrogen atom, form a 3-12-membered monocyclic or bicyclic saturated, partially unsaturated, or fully unsaturated ring having 0-3 additional heteroatoms independently selected from nitrogen, sulfur, or oxygen, wherein said ring is optionally substituted at one or more substitutable ring atoms with z independent occurrences of $-R^4$, wherein z is 0-5;

y is 0-5;

each occurrence of $R^3$, $R^4$, and $R^5$ is independently Q-R$^x$; wherein Q is a bond or is a $C_1$-$C_6$ alkylidene chain wherein up to two non-adjacent methylene units of Q are optionally and independently replaced by $-NR-$, $-S-$, $-O-$, $-CS-$, $-CO_2-$, $-OCO-$, $-CO-$, $-COCO-$, $-CONR-$, $-NRCO-$, $-NRCO_2-$, $-SO_2NR-$, $-NRSO_2-$, $-CONRNR-$, $-NRCONR-$, $-OCONR-$, $-NRNR-$, $-NRSO_2NR-$, $-SO-$, $-SO_2-$, $-PO-$, $-PO_2-$, $-OP(O)(OR)-$, or $-POR-$; and each occurrence of Rx is independently selected from $-R'$, halogen, $-NO_2$, $-CN$, $-OR'$, $-SR'$, $-N(R')_2$, $-NR'COR'$, $-NR'CON(R')_2$, $-NR'CO_2R'$, $-COR'$, $-CO_2R'$, $-OCOR'$, $-CON(R')_2$, $-OCON(R')_2$, $-SOR'$, $-SO_2R'$, $-SO_2N(R')_2$, $-NR'SO_2R'$, $-NR'SO_2N(R')_2$, $-COCOR'$, $-COCH_2COR'$, $-OP(O)(OR')_2$, $-P(O)(OR')_2$, $-OP(O)_2OR'$, $-P(O)_2OR'$, $-PO(R')_2$, or $-OPO(R')_2$;

each occurrence of R is independently hydrogen or an optionally substituted $C_{1-6}$ aliphatic group;

each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In one embodiment, the following compounds are excluded:

(i) when $X_1$ is S, $X_2$ is =CH—, $X^3$ is a lone pair of electrons, W, together with $R^5$ and y is 2,4-difluorophenyl, then $R^1$ and $R^2$ taken together is not optionally substituted 2,3-dihydro-1H-isoindol-1-one-2-yl;

(ii) when $X_1$ is S, $X_2$ is =CH—, $X^3$ is a lone pair of electrons, W, together with $R^5$ and y is 2,4-dichlorophenyl, then $R^1$ and $R^2$ taken together is not optionally substituted 2,3-dihydro-1H-indol-1-yl or an optionally substituted tetracyclic ring system;

(iii) when $X_1$ is S, $X_2$ is =CMe-, $X^3$ is a lone pair of electrons, W, together with $R^5$ and y is 2,4-dimethoxyphenyl, then $R^1$ and $R^2$ taken together is not an optionally substituted pyrrol-1-yl ring fused to an optionally substituted pyridazine ring;

(iv) when $X_1$ is S, $X_2$ is =$CR^3$—, and $X^3$ is a lone pair of electrons, then $R^1$ and $R^2$ taken together is not an optionally substituted pyrrol-1-yl;

(v) when $X_1$ is =N—, $X^2$ is O, $X^3$ is a lone pair of electrons, and W is halo, then $R^1$ and $R^2$ taken together is not 1,4-diazabicyclo[3.2.2]nonan-1-yl;

(vi) when $X_1$ is S, $X_2$ is =CH—, $X^3$ is a lone pair of electrons, W, together with $R^5$ and y is 2-chlorophenyl, then $R^1$ and $R^2$ taken together is not an optionally substituted imidazol-1-yl;

(vii) when $X_1$ is =N—, $X_2$ is =CH—, $X_3$ is H, y is 0, and W is $NHSO_2Ar'$, wherein Ar' is an optionally substituted phenyl, then $R^1$ and $R^2$ taken together is not 2-butanamido-pyrrolidin-1-yl;

(viii) when $X_1$ is =N—, $X_2$ is =CH— or =C(Cl)—, $X_3$ is H, and W is $NHSO_2Ar'$, wherein Ar' is an optionally substituted phenyl or NHC(O)R, wherein R is an optionally substituted aliphatic, then $R^1$ and $R^2$ taken together is not 3-[(dimethylamino)sulfonyl]amino-morpholin-4-yl or 2-(methoxycarbonyl)amino-4,5-dichloro-1H-imidazol-1-yl;

(ix) when $X_1$ is S, $X_2$ is =CH—, $X_3$ is a lone pair of electrons, W is OH or OMe, then $R^1$ and $R^2$ taken together is not 3,4-dihydro-2-(1H)-quinozolin-3-one-2-yl;

(x) when $X_1$ is S, $X_2$ is =CH—, $X_3$ is a lone pair of electrons, and W is halo or OR', then $R^1$ and $R^2$ taken together is not an optionally substituted 2-imino-thiazolidin-4-one-3-yl;

(xi) when $X_1$ is S, $X_2$ is =CH—, and $X_3$ is a lone pair of electrons, then $R^1$ and $R^2$ taken together is not an optionally substituted azetidin-2-one-1-yl;

(xii) when $X_1$ is S, $X_2$ is =$CR^3$—, $X_3$ is a lone pair of electrons, and W is OH or halo, then $R^1$ and $R^2$ taken together is not an optionally substituted 3,4-dihydro-(3H)-quinazolin-4-one-3-yl;

(xiii) when $X_1$ is S, $X_2$ is =$CR^3$—, $X_3$ is a lone pair of electrons, and W is halo, OMe, or $NHSO_2Ar'$, wherein Ar' is an optionally substituted phenyl, then $R^1$ and $R^2$ taken together is not an optionally substituted ring selected from thiazolidin-4-one-3-yl, 2,4-dioxo-imidazolin-1-yl, 4,5-dihydro-5-oxo-(1H)-imidazol-1-yl, or azetidin-1-yl;

(xiv) when $X_1$ is S, $X_2$ is =CH—, $X_3$ is a lone pair of electrons, and W is halo, then $R^1$ and $R^2$ taken together is not 1,2,3,4-tetrahydro-(1H)-quinazolin-2,4-dioxo-3-yl; and (xv) when $X_1$ is =N—, $X_2$ is =$CR^3$—, $X_3$ is H, then $R^1$ and $R^2$ taken together is not 3,5-dioxo-1,2,4-triazolidin-4-yl, 2,5-dioxo-pyrrolidin-1-yl, or 2,5-dioxo-imidazolidin-1-yl.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In some embodiments, "cycloaliphatic" (or "carbocycle" or "cycloalkyl") refers to a monocyclic or bicyclic hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise specified herein, suitable substituents on the unsaturated carbon atom of an aryl or heteroaryl group are generally selected from halogen; —$R^o$; —$OR^o$; —$SR^o$; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —C(O)C(O)$R^o$; —C(O)$CH_2$C(O)$R^o$; —$CO_2R^o$; —C(O)$R^o$; —C(S)$R^o$; —C(O)N($R^o$)$_2$; —C(S)N($R^o$)$_2$; —OC(O)N($R^o$)$_2$; —OC(O)$R^o$; —C(O)N(O$R^o$)$R^o$; —C(NO$R^o$)$R^o$; —$S(O)_2R^o$; —$S(O)_3R^o$; —$SO_2N(R^o)_2$; —$S(O)R^o$; —$NR^oSO_2N(R^o)_2$; —$NR^oSO_2R^o$; —N(O$R^o$)$R^o$; —C(=NH)—N($R^o$)$_2$; —$P(O)_2R^o$; —PO($R^o$)$_2$; —OPO($R^o$)$_2$; —$(CH_2)_{0-2}$NHC(O)$R^o$; phenyl (Ph) optionally substituted with $R^o$; —O(Ph) optionally substituted with $R^o$; —$(CH_2)_{1-2}$(Ph), optionally substituted with $R^o$; or —CH=CH(Ph), optionally substituted with $R^o$; wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Unless otherwise specified herein, optional substituents on the aliphatic group of $R^o$ are selected from $NH_2$, NH($C_{1-4}$ aliphatic), N($C_{1-4}$aliphatic)$_2$, halogen, $C_{1-4}$aliphatic, OH, O($C_{1-4}$aliphatic), $NO_2$, CN, $CO_2H$, $CO_2(C_{1-4}$aliphatic), O(halo$C_{1-4}$ aliphatic), or halo$C_{1-4}$aliphatic, wherein each of the foregoing $C_{1-4}$aliphatic groups of $R^o$ is unsubstituted.

An aliphatic or heteroaliphatic group, or a non-aromatic heterocyclic ring may contain one or more substituents and thus may be "optionally substituted". Unless otherwise specified herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic group.

Unless otherwise specified herein, optional substituents on the nitrogen of a non-aromatic heterocyclic ring are generally selected from —$R^+$, —N($R^+$)$_2$, —C(O)$R^+$, —$CO_2R^+$, —C(O)C(O)$R^+$, —C(O)$CH_2$C(O)$R^+$, —$SO_2R^+$, —$SO_2N(R^+)_2$, —C(=S)N($R^+$)$_2$, —C(=NH)—N($R^+$)$_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Unless otherwise specified herein, optional substituents on the aliphatic group or the phenyl ring of $R^+$ are selected from —$NH_2$, —NH($C_{1-4}$ aliphatic), —N($C_{1-4}$ aliphatic)$_2$, halogen, $C_{1-4}$ aliphatic, —OH, —O($C_{1-4}$ aliphatic), —$NO_2$, —CN, —$CO_2H$, —$CO_2(C_{1-4}$ aliphatic), —O(halo $C_{1-4}$ aliphatic), or halo($C_{1-4}$ aliphatic), wherein each of the foregoing $Cl_4$aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of $R^o$ (or $R^+$, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of $R^o$ (or $R^+$, R, R' or any other variable similarly defined herein), are taken together with the atom(s) to which each variable is bound include, but are not limited to the following: a) two independent occurrences of $R^o$ (or $R^+$, R, R' or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, R, R' or any other variable similarly defined herein) that are bound to different atoms and are taken together with both of those atoms to form a ring, for example where a phenyl group is substituted with two occurrences of

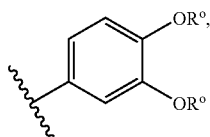

these two occurrences of $R^o$ are taken together with the oxygen atoms to which they are bound to form a fused 6-membered oxygen containing ring:

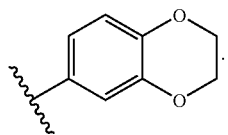

It will be appreciated that a variety of other rings can be formed when two independent occurrences of $R^o$ (or $R^+$, R, R' or any other variable similarly defined herein) are taken together with the atom(s) to which each variable is bound and that the examples detailed above are not intended to be limiting.

Unless otherwise specified herein, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon or a nitrogen by a $^{15}N$ nitrogen are within the scope of this invention. Such compounds are useful, for example, as analytical tools or probes in biological assays.

3. Description of Exemplary Compounds

In one embodiment, $X_1$, $X_2$, and $X_3$ taken together form a ring selected from:

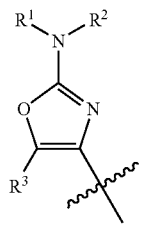

i

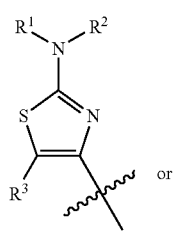

ii or

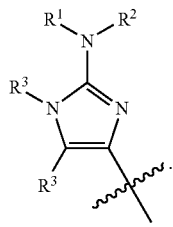

iii

In one embodiment, $X_1$, $X_2$, and $X_3$ taken together form ring i. Or, said ring is ring ii. Or, said ring is ring iii.

In another embodiment, $X_1$, $X_2$, and $X_3$ taken together form a ring selected from:

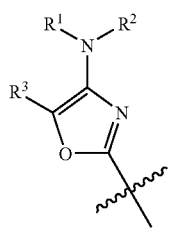

iv

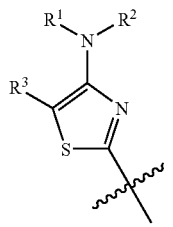

v

-continued

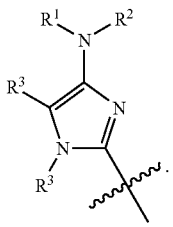
vi

In one embodiment, $X_1$, $X_2$, and $X_3$ taken together form ring iv. Or, said ring is ring v. Or, said ring is ring vi.

In another embodiment, $X_1$, $X_2$, and $X_3$ taken together form a ring selected from:

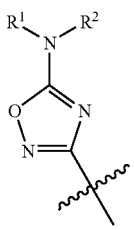
vii

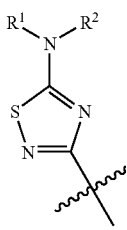
viii

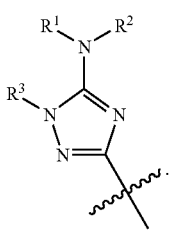
ix

In one embodiment, $X_1$, $X_2$, and $X_3$ taken together form ring vii. Or, said ring is ring viii. Or, said ring is ring ix.

In another embodiment, $X_1$, $X_2$, and $X_3$ taken together form a ring selected from:

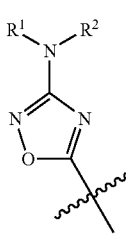
x

-continued xi xii

In one embodiment, $X_1$, $X_2$, and $X_3$ taken together form ring x. Or, said ring is ring xi. Or, said ring is ring xii.

In another embodiment $X_1$, $X_2$, and $X_3$ taken together form ring xiii:

xiii

In one embodiment, $X_1$, $X_2$, and $X_3$ are taken together to form ring ii, W is halo or OR', $R^1$ and $R^2$, taken together with the nitrogen atom, form a 6-membered monocyclic saturated ring having 0-1 additional heteroatoms selected from nitrogen, wherein said ring is optionally substituted at one or more substitutable ring atoms with z independent occurrences of —$R^4$, wherein z is 0.

In another embodiment, $X_1$, $X_2$, and $X_3$ are taken together to form ring ii, W is halo or OR', and $R^1$ and $R^2$ taken together, form ring mm or nn.

In another embodiment, $X_1$, $X_2$, and $X_3$ are taken together to form ring ii, W is halo or OR', and $R^1$ and $R^2$ form a ring shown below:

In another embodiment, $X_1$, $X_2$, and $X_3$ are taken together to form ring viii or xi, W is halo or OR', $R^1$ and $R^2$, taken together with the nitrogen atom, form a 6-membered monocyclic saturated ring having 0-1 additional heteroatoms selected from nitrogen, wherein said ring is optionally substituted at one or more substitutable ring atoms with z independent occurrences of —$R^4$, wherein z is 0.

In another embodiment, $X_1$, $X_2$, and $X_3$ are taken together to form viii or xi, W is halo or OR', and $R^1$ and $R^2$ taken together, form ring mm or nn.

In one embodiment, $R^1$ and $R^2$, taken together with the nitrogen atom to which they are bound, form an optionally substituted 3-8-membered monocyclic, saturated or partially unsaturated ring having 0-3 additional heteroatoms independently selected from nitrogen, sulfur, or oxygen; wherein the ring formed by $R^1$ and $R^2$ taken together, are each optionally and independently substituted at one or more substitutable carbon, nitrogen, or sulfur atoms with z independent occurrences of —$R^4$, wherein z is 0-5.

In another embodiment, $R^1$ and $R^2$, taken together with the nitrogen atom to which they are bound, form an optionally substituted 3-8-membered monocyclic, saturated or partially unsaturated ring having 0-3 additional heteroatoms independently selected from nitrogen, sulfur, or oxygen, wherein the ring atom in each of $R^1$ and $R^2$ adjacent to said nitrogen atom is a —$CH_2$—; wherein the ring formed by $R^1$ and $R^2$ taken together, are each optionally and independently substituted at one or more substitutable carbon, nitrogen, or sulfur atoms with z independent occurrences of —$R^4$, wherein z is 0-5.

In one embodiment of the present invention, $R^1$ and $R^2$ taken together form an azetidinyl ring:

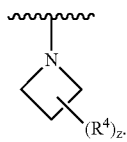

aa

In another embodiment of the present invention, $R^1$ and $R^2$ taken together form a pyrrolidinyl ring:

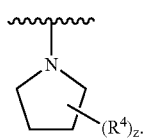

bb

In another embodiment of the present invention, $R^1$ and $R^2$ taken together form a piperidinyl ring:

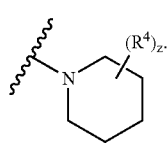

cc

In another embodiment of the present invention, $R^1$ and $R^2$ taken together form a piperazinyl ring:

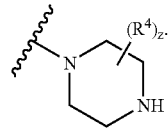

dd

In another embodiment of the present invention, $R^1$ and $R^2$ taken together form a morpholinyl ring:

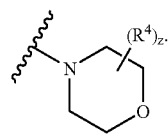

ee

In another embodiment of the present invention, $R^1$ and $R^2$ taken together form a thiomorpholinyl ring:

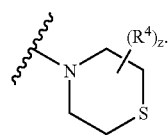

ff

In another embodiment of the present invention, $R^1$ and $R^2$ taken together form an azepanyl ring:

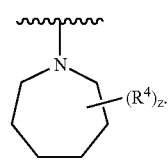

gg

In another embodiment of the present invention, $R^1$ and $R^2$ taken together form an azocanyl ring:

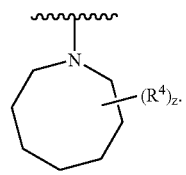

hh

In one embodiment, $R^1$ and $R^2$ together form a ring (ii) or (jj) as shown below:

(ii)
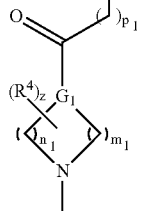

(jj)
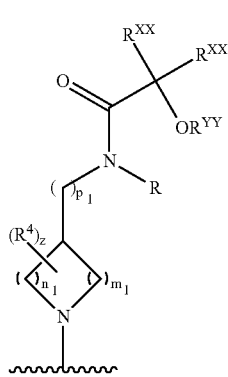

wherein:

$G_1$ is —N—, —CH—NH—, or —CH—CH$_2$—NH—;

each of $m_1$ and $n_1$ is independently 0-3, provided that $m_1+n_1$ is 2-6;

$p_1$ is 0-2;

z is 0-4;

each $R^{XX}$ is hydrogen, $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $R^{XX}$ is optionally substituted with $w_1$ independent occurrences of —$R^{11}$, wherein $w_1$ is 0-3;

provided that both $R^{XX}$ are not simultaneously hydrogen;

$R^{YY}$ is hydrogen, —COR', —CO$_2$R', —CON(R')$_2$, —SOR', —SO$_2$R', —SO$_2$N(R')$_2$, —COCOR', —COCH$_2$COR', —P(O)(OR')$_2$, —P(O)$_2$OR', or —PO(R');

each occurrence of $R^{11}$ is independently Q-$R^X$; wherein Q is a bond or is a $C_1$-$C_6$ alkylidene chain wherein up to two non-adjacent methylene units of Q are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, —OP(O)(OR)—, or —POR—; and each occurrence of Rx is independently selected from —R', halogen, =O, =NR', —NO$_2$, —CN, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or $C_{1-6}$ aliphatic group having up to three substituents; and each occurrence of R' is independently hydrogen or $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R' has up to four substituents; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In one embodiment of the present invention, one $R^{XX}$ is hydrogen and the other $R^{XX}$ is not hydrogen.

In another embodiment of the present invention, both $R^{XX}$ are not hydrogen.

In one embodiment of the present invention, $p_1$ is 0. Or, $p_1$ is 1. Or, $p_1$ is 2.

In one embodiment of the present invention, $m_1$ and $n_1$ each is 1. Or, $m_1$ and $n_1$ each is 2. Or, $m_1$ and $n_1$ each is 3.

In one embodiment of the present invention, $R^{XX}$ is $C_{1-6}$ aliphatic group, wherein $R^{XX}$ is optionally substituted with $w_1$ independent occurrences of —$R^{11}$, wherein $w_1$ is 0-3. Or, $R^{XX}$ is C1-C6 alkyl group optionally substituted with $w_1$ independent occurrences of —$R^{11}$, wherein $w_1$ is 0-3.

In one embodiment of the present invention, $R^{XX}$ is C1-C6 alkyl group.

In another embodiment of the present invention, $R^{XX}$ is a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein $R^{XX}$ is optionally substituted with $w_1$ independent occurrences of —$R^{11}$, wherein $w_1$ is 0-3.

In another embodiment, $R^{XX}$ is a 3-8-membered saturated, partially unsaturated, or fully unsaturated monocyclic ring having 0-3 heteroatoms independently selected from nitrogen, oxygen, or sulfur, wherein $R^{XX}$ is optionally substituted with $w_1$ independent occurrences of —$R^{11}$, wherein $w_1$ is 0-3.

In another embodiment, $R^{XX}$ is an 8-12 membered saturated, partially unsaturated, or fully unsaturated bicyclic ring system having 0-5 heteroatoms independently selected from nitrogen, oxygen, or sulfur, wherein $R^{XX}$ is optionally substituted with $w_1$ independent occurrences of —$R^{11}$, wherein $w_1$ is 0-3.

In another embodiment, $R^{YY}$ is hydrogen, —COR', —CO$_2$R', —CON(R')$_2$, —SOR', —SO$_2$R', —SO$_2$N(R')$_2$, —COCOR', —COCH$_2$COR', —P(O)(OR')$_2$, —P(O)$_2$OR', or —PO(R').

Or, $R^{YY}$ is hydrogen.

In another embodiment, $R^{YY}$ is —COR', —CO$_2$R', —CON(R')$_2$, —SOR', —SO$_2$R', —SO$_2$N(R')$_2$, —COCOR', —COCH$_2$COR', —P(O)(OR')$_2$, —P(O)$_2$OR', or —PO(R').

In one embodiment, R is hydrogen. Or, R is C1-C6 alkyl. Preferred R include methyl, ethyl, propyl, or butyl.

In another embodiment, $R^{YY}$ is hydrogen, one $R^{XX}$ is hydrogen, and the other $R^{XX}$ is C1-C6 alkyl.

In yet another embodiment, $p_1$ is 0, $R^{YY}$ is hydrogen, one $R^{XX}$ is hydrogen, and the other $R^{XX}$ is C1-C6 alkyl.

In another embodiment, $R^{YY}$ is hydrogen, one $R^{XX}$ is hydrogen, and the other $R^{XX}$ is C1-C6 alkyl.

In yet another embodiment, $p_1$ is 0, $R^{YY}$ is hydrogen, one $R^{XX}$ is hydrogen, and the other $R^{XX}$ is C1-C6 alkyl.

In one embodiment of the present invention, $R^1$ and $R^2$ together form a ring as shown below:

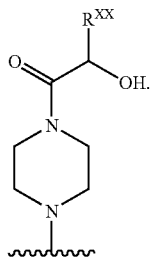

In one embodiment, $R^{XX}$ is C1-C6 alkyl.

In one embodiment, $R^{XX}$ is methyl, n-propyl, isopropyl, n-butyl, isobutyl, or t-butyl.

In one embodiment, $R^1$ and $R^2$ taken together form ring (kk) as shown below:

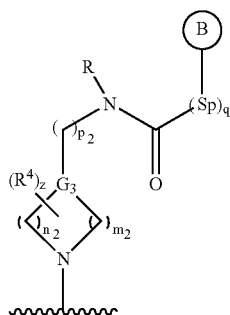

kk $G_3$ is —N—, or CH;

each of $m_2$ and $n_2$ is independently 0-3, provided that $m_2+n_2$ is 2-6;

$p_2$ is 0-2; provided that when $G_3$ is N, then $p_2$ is not 0;

$q_2$ is 0 or 1;

z is 0-4;

Sp is a bond or a C1-C6 alkylidene linker, wherein up to two methylene units are optionally and independently replaced by —O—, —S—, —CO—, —CS—, —COCO—, —CONR'—, —CONR'NR'—, —CO$_2$—, —OCO—, —NR'CO$_2$—, —NR'CONR'—, —OCONR'—, —NR'NR', —NR'NR'CO—, —NR'CO—, —SO, —SO$_2$—, —NR'—, —SO$_2$NR'—, NR'SO$_2$—, or —NR'SO$_2$NR'—;

ring B is a 4-8 membered, saturated, partially unsaturated, or aromatic, monocyclic heterocyclic ring having 1-4 heteroatoms selected from O, S, or N, wherein ring B is optionally substituted with $w_2$ independent occurrences of —$R^{12}$, wherein $w_2$ is 0-4;

each occurrence of $R^{12}$ is independently Q-Rx; wherein Q is a bond or is a $C_1$-$C_6$ alkylidene chain wherein up to two non-adjacent methylene units of Q are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, —OP(O)(OR)—, or —POR—; and each occurrence of $R^X$ is independently selected from —R', halogen, =O, =NR', —NO$_2$, —CN, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or $C_{1-6}$ aliphatic group having up to three substituents; and each occurrence of R is independently hydrogen or $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R' has up to four substituents; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In one embodiment, $G_3$ is N. Or, $G_3$ is CH.

In one embodiment, $p_2$ is 0. Or, $p_2$ is 1. Or, $p_2$ is 2.

In another embodiment, $q_2$ is 0. Or, $q_2$ is 1.

In one embodiment, $p_2$ is 1, and $q_2$ is 1.

In another embodiment, $G_3$ is CH, $p_2$ is 0, and $q_2$ is 1.

In one embodiment, $m_2$ and $n_2$ each is 1. Or, $m_2$ and $n_2$ each is 2.

In another embodiment, Sp is selected from —O—, —S—, or —NR'—. In one embodiment, Sp is —O—. Or, Sp is —NR'—. Or, Sp is —NH—.

In one embodiment, ring B is a 4-8 membered, saturated, partially unsaturated, or aromatic, monocyclic heterocyclic ring having 1-4 heteroatoms selected from O, S, or N, wherein ring B is optionally substituted with $w_2$ independent occurrences of —$R^{12}$ wherein $w_2$ is 0-4.

In another embodiment, ring B is a 4-8 membered, saturated, monocyclic heterocyclic ring having 1-4 heteroatoms selected from O, S, or N, wherein ring B is optionally substituted with $w_2$ independent occurrences of —$R^{12}$, wherein $w_2$ is 0-4.

In yet another embodiment, ring B is a 5-6 membered, saturated, monocyclic heterocyclic ring having 1-2 heteroatoms selected from O, S, or N, wherein ring B is optionally substituted with $w_2$ independent occurrences of —$R^{12}$, wherein $w_2$ is 0-4.

In one embodiment, $w_2$ is 0.
In another embodiment, ring B is tetrahydrofuranyl.
In yet another embodiment, i) Sp is a bond, O, or —$CH_2$—;

ii) $p_2$ is 1;

iii) R is hydrogen; and iv) $n_2$ and $m_2$ are both simultaneously 1 or 2.

In one embodiment, R is hydrogen. Or, R is C1-C6 alkyl. Preferred R include methyl, ethyl, propyl, or butyl.

In one embodiment, $R^1$ and $R^2$ taken together form a ring of formula (kk-i) or formula (kk-ii):

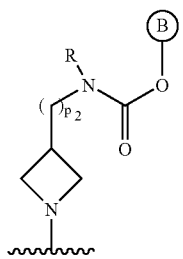

kk-i

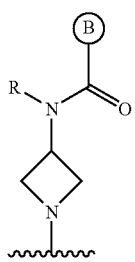

kk-ii

According to one embodiment, ring B is a 5-6 membered, saturated, monocyclic heterocyclic ring having 1-2 heteroatoms selected from O, S, or N, wherein ring B is optionally substituted with $w_2$ independent occurrences of —$R^2$, wherein $w_2$ is 0-4.

According to another embodiment, R is hydrogen. Or, R is hydrogen and ring B is tetrahydrofuranyl.

According to yet another embodiment, Sp is a bond, —O—, or —O—$CH_2$—.

In one embodiment, $R^1$ and $R^2$ taken together form a ring (ll):

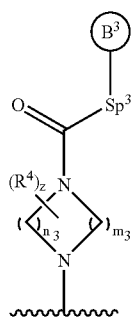

II each of $m_3$ and $n_3$ is independently 0-3, provided that $m_3+n_3$ is 2-6;

z is 0-4;

$Sp^3$ is —O—, —S—, —NR'—, or a C1-C6 alkylidene linker, wherein up to two methylene units are optionally and independently replaced by —O—, —S—, —CO—, —CS—, —COCO—, —CONR'—, —CONR'NR'—, —$CO_2$—, —OCO—, —NR'$CO_2$—, —NR'CONR'—, —OCONR'—, —NR'NR', —NR'NR'CO—, —NR'CO—, —SO, —$SO_2$—, —NR'—, —$SO_2$NR'—, NR'$SO_2$—, or —NR'$SO_2$NR'—, provided that $Sp^3$ is attached to the carbonyl group through an atom other than carbon;

ring $B_3$ is a 4-8 membered, saturated, partially unsaturated, or aromatic, monocyclic heterocyclic ring having 1-4 heteroatoms selected from O, S, or N, wherein ring $B_3$ is optionally substituted with $w_3$ independent occurrences of —$R^{13}$, wherein $w_3$ is 0-4;

each occurrence of $R^{13}$ is independently Q-$R^x$; wherein Q is a bond or is a $C_1$-$C_6$ alkylidene chain wherein up to two non-adjacent methylene units of Q are optionally and independently replaced by —NR—, —S—, —O—, —CS—, —$CO_2$—, —OCO—, —CO—, —COCO—, —CONR—, —NRCO—, —$NRCO_2$—, —$SO_2$NR—, —$NRSO_2$—, —CONRNR—, —NRCONR—, —OCONR—, —NRNR—, —$NRSO_2$NR—, —SO—, —$SO_2$—, —PO—, —$PO_2$—, —OP(O)(OR)—, or —POR—; and each occurrence of Rx is independently selected from —R', halogen, =O, =NR', —$NO_2$, —CN, —OR', —SR', —N(R')$_2$, —NR'COR', —NR'CON(R')$_2$, —NR'$CO_2$R', —COR', —$CO_2$R', —OCOR', —CON(R')$_2$, —OCON(R')$_2$, —SOR', —$SO_2$R', —$SO_2$N(R')$_2$, —NR'$SO_2$R', —NR'$S_2$N(R')$_2$, —COCOR', —$COCH_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or $C_{1-6}$ aliphatic group having up to three substituents; and each occurrence of R is independently hydrogen or $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R' has up to four substituents; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In one embodiment, $Sp^3$ is selected from —O—, —S—, or —NR'—. Or, Sp is —O—. Or, $Sp^3$ is —O—$CH_2$—. In another embodiment, $Sp^3$ is —NR'—. Or, $Sp^3$ is —NH—. Or, $Sp^3$ is —NH—$CH_2$—.

In one embodiment, each of $m_3$ and $n_3$ is 1. In another embodiment, each of $m_3$ and $n_3$ is 2.

In one embodiment, ring $B_3$ is a 4-8 membered, saturated, partially unsaturated, or aromatic, monocyclic heterocyclic ring having 1-4 heteroatoms selected from O, S, or N, wherein ring $B_3$ is optionally substituted with $w_3$ independent occurrences of —$R^{13}$, wherein $w_3$ is 0-4.

In another embodiment, ring $B_3$ is a 4-8 membered, saturated, monocyclic heterocyclic ring having 1-4 heteroatoms selected from O, S, or N, wherein ring $B_3$ is optionally substituted with $w_3$ independent occurrences of —$R^3$, wherein $w_3$ is 0-4.

In yet another embodiment, ring $B_3$ is a 5-6 membered, saturated, monocyclic heterocyclic ring having 1-2 heteroatoms selected from O, S, or N, wherein ring $B_3$ is optionally substituted with $w_3$ independent occurrences of —$R^3$, wherein $w_3$ is 0-4.

In one embodiment, $w_3$ is 0.

In another embodiment, ring $B_3$ is tetrahydrofuranyl.

In yet another embodiment, $Sp^3$ is a bond, 0, or —O—$CH_2$—; R is hydrogen; and $n_3$ and $m_3$ are both simultaneously 1 or 2.

In one embodiment, R is hydrogen. Or, R is $C_1$-$C_6$ alkyl. Preferred R include methyl, ethyl, propyl, or butyl.

In another embodiment, z is 0.

According to one embodiment, ring $B_3$ is a 5-6 membered, saturated, monocyclic heterocyclic ring having 1-2 heteroatoms selected from O, S, or N, wherein ring $B_3$ is optionally substituted with $w_3$ independent occurrences of —$R^3$, wherein $w_3$ is 0-4.

According to another embodiment, R is hydrogen. Or, R is hydrogen and ring $B_3$ is tetrahydrofuranyl.

According to yet another embodiment, $Sp_3$ is a bond, —O—, —O—$CH_2$—, or —NH—$CH_2$.

In one embodiment, $R^1$ and $R^2$ taken together form a ring (mm):

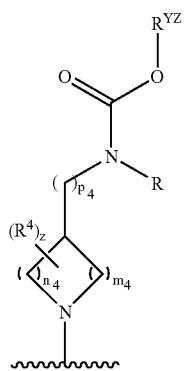

mm each of $m_4$ and $n_4$ is independently 0-3, provided that $m_4+n_4$ is 2-6;

$p_4$ is 1-2;

$R^{YZ}$ is $C_1$-$C_6$ aliphatic group, optionally substituted with $w_4$ independent occurrences of —$R^{14}$, wherein $w_4$ is 0-3;

each occurrence of $R^{14}$ is independently Q-Rx; wherein Q is a bond or is a $C_1$-$C_6$ alkylidene chain wherein up to two non-adjacent methylene units of Q are optionally and independently replaced by —NR—, —S—, —O—, —CS—, —$CO_2$—, —OCO—, —CO—, —COCO—, —CONR—, —NRCO—, —NRCO_2—, —SO_2NR—, —NRSO_2—, —CONRNR—, —NRCONR—, —OCONR—, —NRNR—, —NRSO_2NR—, —SO—, —SO_2—, —PO—, —PO_2—, —OP(O)(OR)—, or —POR—; and each occurrence of Rx is independently selected from —R', halogen, =O, =NR', —NO_2, —CN, —OR', —SR', —N(R')_2, —NR'COR', —NR'CON(R')_2, —NR'CO_2R', —COR', —CO_2R', —OCOR', —CON(R')_2, —OCON(R')_2, —SOR', —SO_2R', —SO_2N(R')_2, —NR'SO_2R', —NR'SO_2N(R')_2, —COCOR', —COCH_2COR', —OP(O)(OR')_2, —P(O)(OR')_2, —OP(O)_2OR', —P(O)_2OR', —PO(R')_2, or —OPO(R')_2; and each occurrence of R is independently hydrogen or $C_{1-6}$ aliphatic group having up to three substituents; and each occurrence of R is independently hydrogen or $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R' has up to four substituents; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In one embodiment, $p_4$ is 1. Or, $p_4$ is 2.

In one embodiment, $m_4$ and $n_4$ each is 1. Or, $m_4$ and $n_4$ each is 2. Or, $m_4$ and $n_4$ each is 3.

In one embodiment, $R^{YZ}$ is C1-C6 alkyl, optionally substituted with $w_4$ independent occurrences of —$R^{14}$, wherein $w_4$ is 0-3. In another embodiment, $R^{YZ}$ is C1-C4 alkyl group optionally substituted with $w_4$ independent occurrences of —$R^{14}$, wherein $w_4$ is 0-3. Or, $R^Y$ is C1-C6 alkyl group.

In one embodiment, R is hydrogen. Or, R is C1-C6 alkyl. Preferred R groups include methyl, ethyl, propyl, or butyl.

In another embodiment, $R^1$ and $R^2$ taken together form a ring (mm-1):

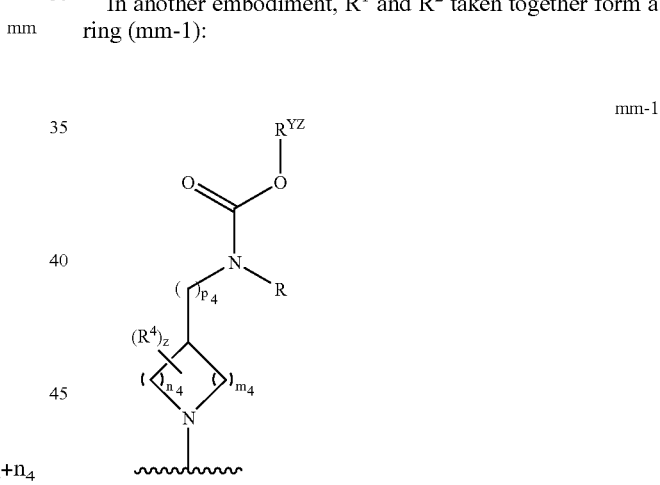

mm-1 each of $m_4$ and $n_4$ is independently 0-3, provided that $m_4+n_4$ is 2-6;

$p_4$ is 0-2;

$R^{YZ}$ is $C_1$-$C_6$ aliphatic group, optionally substituted with $w_4$ independent occurrences of —$R^{14}$, wherein $w_4$ is 0-3;

wherein up to two methylene units in $R^{YZ}$ are optionally replaced with —NR—, —O—, —$CO_2$—, —OCO—, —NRCO—, —CONR—, —CO—, —$SO_2$NR—, or —$NRSO_2$—;

each occurrence of $R^{14}$ is independently Q-$R^X$; wherein Q is a bond or is a $C_1$-$C_6$ alkylidene chain wherein up to two non-adjacent methylene units of Q are optionally and independently replaced by —NR—, —S—, —O—, —CS—, —$CO_2$—, —OCO—, —CO—, —COCO—, —CONR—, —NRCO—, —NRCO_2—, —SO_2NR—, —NRSO_2—, —CONRNR—, —NRCONR—, —OCONR—, —NRNR—, —NRSO$_2$NR—, —SO—, —SO$_2$—, —PO—, —PO$_2$—, —OP(O)(OR)—, or —POR—; and each occurrence of Rx is independently selected from —R', halogen, =O, =NR', —NO$_2$, —CN, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or C$_{1-6}$ aliphatic group having up to three substituents; and each occurrence of R' is independently hydrogen or C$_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R' has up to four substituents; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In one embodiment, $p_4$ is 1. Or, $p_4$ is 2.

In another embodiment, $p_4$ is 0.

In one embodiment, $m_4$ and $n_4$ each is 1. Or, $m_4$ and $n_4$ each is 2. Or, $m_4$ and $n_4$ each is 3.

In one embodiment, $R^{YZ}$ is C1-C6 alkyl, optionally substituted with $w_4$ independent occurrences of —$R^{14}$, wherein $w_4$ is 0-3. In another embodiment, $R^{YZ}$ is C1-C4 alkyl group optionally substituted with $w_4$ independent occurrences of —$R^4$, wherein $w_4$ is 0-3. Or, $R^Y$ is C1-C6 alkyl group.

In one embodiment, R is hydrogen. Or, R is C1-C6 alkyl. Preferred R groups include methyl, ethyl, propyl, or butyl.

In another embodiment, the present invention provides a compound of formula mm-2 or mm-3:

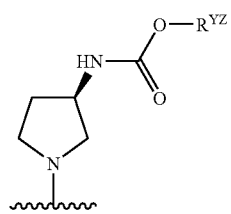

mm-2

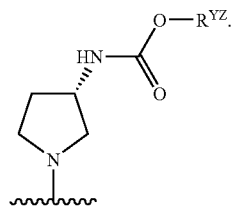

mm-3

In one embodiment of formula mm-2 and mm-3, $R^{YZ}$ is an unsubstituted C$_1$-C$_6$ aliphatic group.

In one embodiment of formula mm-2, $R^{YZ}$ is —CH$_3$, —CH$_2$CH$_3$, —CH(CH$_3$)$_2$, —CH$_2$CH$_2$CH$_3$, —CH(CH$_3$)$_3$, —CH$_2$CH(CH$_3$)$_2$, or —CH$_2$C(CH$_3$)$_3$.

In one embodiment of formula mm-3, $R^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In one embodiment, $R^1$ and $R^2$ are taken together to form a ring (nn):

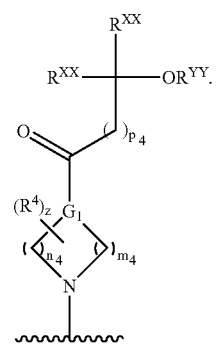

nn

In one embodiment, G$_1$ is —N—. Or, G$_1$ is —CH—NH—. Or, G$_1$ is —CH—CH$_2$—NH—.

In another embodiment, $R^{YY}$ is hydrogen, one $R^{XX}$ is hydrogen, and the other $R^{XX}$ is C1-C6 alkyl.

In yet another embodiment, $p_4$ is 0, $R^{YY}$ is hydrogen, one $R^{XX}$ is hydrogen, and the other $R^{XX}$ is C1-C6 alkyl.

In one embodiment, $R^1$ and $R^2$ are taken together to form a ring (pp):

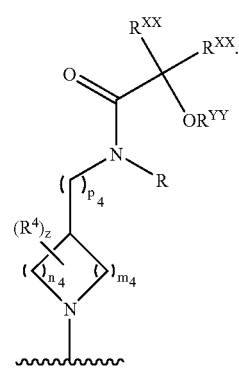

pp

In another embodiment, $R^{YY}$ is hydrogen, one $R^{XX}$ is hydrogen, and the other $R^{XX}$ is C1-C6 alkyl.

In yet another embodiment, $p_4$ is 0, $R^{YY}$ is hydrogen, one $R^{XX}$ is hydrogen, and the other $R^{XX}$ is C1-C6 alkyl.

In one embodiment of the present invention, W is OR'. In another embodiment, W is OH.

In one embodiment of the present invention, W is SR'. In another embodiment, W is SH.

In one embodiment of the present invention, W is N(R')$_2$. In another embodiment, W is NHR'. Or, W is NH$_2$.

In one embodiment of the present invention, W is CHF$_2$, or CH$_2$F. In one embodiment, W is CHF$_2$. In another embodiment, W is CH$_2$F.

In another embodiment, W is CF$_3$.

In one embodiment of the present invention, z is 0-5. In another embodiment, z is 1-3. In yet another embodiment, z is 1-2. In yet another embodiment, z is 1.

In one embodiment of the present invention, $R^4$ is independently halogen, CN, NO$_2$, —N(R')$_2$, —CH$_2$N(R')$_2$, —OR', —$CH_2OR'$, —$SR'$, —$CH_2SR'$, —$COOR'$, —$NRCOR'$, —$CON(R')_2$, —$OCON(R')_2$, $COR'$, —$NHCOOR'$, —$SO_2R'$, —$SO_2N(R')_2$, or an optionally substituted group selected from $C_1$-$C_6$aliphatic, aryl, heteroaryl, cycloaliphatic, heterocycloaliphatic, aryl$C_1$-$C_6$alkyl, heteroaryl$C_1$-$C_6$alkyl, cycloaliphatic$C_1$-$C_6$alkyl, or heterocycloaliphatic$C_1$-$C_6$alkyl.

In another embodiment of the present invention, $R^4$ is independently Cl, Br, F, $CF_3$, $CH_3$, —$CH_2CH_3$, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, —$SO_2(CH_2)_3CH_3$, —$SO_2CH(CH_3)_2$, —$SO_2N(CH_3)_2$, —$SO_2CH_2CH_3$, —$C(O)OCH_2CH(CH_3)_2$, —$C(O)NHCH_2CH(CH_3)_2$, —$NHCOOCH_3$, —$C(O)C(CH_3)_3$, —$COO(CH_2)_2CH_3$, —$C(O)NHCH(CH_3)_2$, —$C(O)CH_2CH_3$, or an optionally substituted group selected from piperidinyl, piperizinyl, morpholino, $C_{1-4}$alkoxy, phenyl, phenyloxy, benzyl, benzyloxy, —$CH_2$cyclohexyl, pyridyl, —$CH_2$pyridyl, or —$CH_2$thiazolyl.

In one embodiment of the present invention, $R^1$ and $R^2$, taken together is optionally substituted azetidin-1-yl (aa), wherein z is 1 or 2 and at least one occurrence of $R^4$ is —$NRSO_2R'$, —$NRCOOR'$, or —$NRCOR'$. In another embodiment, $R^1$ and $R^2$, taken together is optionally substituted azetidin-1-yl (aa), wherein z is 1 and $R^4$ is —$NRSO_2R'$. In another embodiment, $R^1$ and $R^2$, taken together is optionally substituted azetidin-1-yl (aa), wherein z is 1 and $R^4$ is —$NRCOOR'$. In another embodiment, $R^1$ and $R^2$, taken together is optionally substituted azetidin-1-yl (aa), wherein z is 1 and $R^4$ is —$NRCOR'$.

In yet another embodiment, $R^1$ and $R^2$, taken together is optionally substituted pyrrolidin-1-yl (bb), wherein z is 1 or 2 and $R^4$ is Cl, Br, F, $CF_3$, $CH_3$, —$CH_2CH_3$, —$OR'$, or —$CH_2OR'$.

In another embodiment, $R^1$ and $R^2$, taken together is optionally substituted piperidin-1-yl (cc), wherein z is 1 or 2 and at least one occurrence of $R^4$ is Cl, Br, F, $CF_3$, $CH_3$, —$CH_2CH_3$, —$OR'$, or —$CH_2OR'$, —$NRSO_2R'$, —$NRCOOR'$, or —$OCON(R')_2$. In another embodiment, $R^1$ and $R^2$, taken together is optionally substituted piperidin-1-yl (cc), wherein z is 1 and $R^4$ is F, $CF_3$, $CH_3$, —$CH_2CH_3$, —$OR'$, or —$CH_2OR'$. In another embodiment, $R^1$ and $R^2$, taken together is optionally substituted piperidin-1-yl (cc), wherein z is 1 and $R^4$ is —$NRSO_2R'$. In another embodiment, $R^1$ and $R^2$, taken together is optionally substituted piperidin-1-yl (cc), wherein z is 1 and $R^4$ is —$NRCOOR'$.

In yet another embodiment, $R^1$ and $R^2$, taken together is optionally substituted piperazin-1-yl (dd), wherein z is 1 or 2 and at least one occurrence of $R^4$ is —$SOR'$, —$CON(R')_2$, —$SO_2N(R')_2$, —$COR'$, or —$COOR'$. In another embodiment, $R^1$ and $R^2$, taken together is optionally substituted piperazin-1-yl (dd), wherein z is 1 and $R^4$ is —$SOR'$. In another embodiment, $R^1$ and $R^2$, taken together is optionally substituted piperazin-1-yl (dd), wherein z is 1 and $R^4$ is —$COOR'$. In another embodiment, $R^1$ and $R^2$, taken together is optionally substituted piperazin-1-yl (dd), wherein z is 1 and $R^4$ is —$CON(R')_2$. In another embodiment, $R^1$ and $R^2$, taken together is optionally substituted piperazin-1-yl (dd), wherein z is 1 and $R^4$ is —$SO_2N(R')_2$. In another embodiment, $R^1$ and $R^2$, taken together is optionally substituted piperazin-1-yl (dd), wherein z is 1 and $R^4$ is —$COR'$.

In yet another embodiment, $R^1$ and $R^2$, taken together is optionally substituted morpholin-1-yl (ee) or thiomorpholin-1-yl (ff), wherein z is 1 or 2 and at least one occurrence of $R^4$ is —$SOR'$, —$CON(R')_2$, —$SO_2N(R')_2$, —$COR'$, or —$COOR'$. In another embodiment, $R^1$ and $R^2$, taken together is optionally substituted morpholin-1-yl (ee) or thiomorpholin-1-yl (ff), wherein z is 1 and $R^4$ is —$SOR'$. In another embodiment, $R^1$ and $R^2$, taken together is optionally substituted morpholin-1-yl (ee) or thiomorpholin-1-yl (ff), wherein z is 1 and $R^4$ is —$COOR'$. In another embodiment, $R^1$ and $R^2$, taken together is optionally substituted morpholin-1-yl (ee) or thiomorpholin-1-yl (ff), wherein z is 1 and $R^4$ is —$CON(R')_2$. In another embodiment, $R^1$ and $R^2$, taken together is optionally substituted morpholin-1-yl (ee) or thiomorpholin-1-yl (ff), wherein z is 1 and $R^4$ is —$SO_2N(R')_2$. In another embodiment, $R^1$ and $R^2$, taken together is optionally substituted morpholin-1-yl (ee) or thiomorpholin-1-yl (ff), wherein z is 1 and $R^4$ is —$COR'$.

In yet another embodiment, $R^1$ and $R^2$, taken together is optionally substituted azepan-1-yl (gg), wherein z is 1 or 2 and at least one occurrence of $R^4$ is —$SOR'$, —$CON(R')_2$, —$SO_2N(R')_2$, —$COR'$, or —$COOR'$. In another embodiment, $R^1$ and $R^2$, taken together is optionally substituted azepan-1-yl (gg), wherein z is 1 and $R^4$ is —$SOR'$. In another embodiment, $R^1$ and $R^2$, taken together is optionally substituted azepan-1-yl (gg), wherein z is 1 and $R^4$ is —$COOR'$. In another embodiment, $R^1$ and $R^2$, taken together is optionally substituted azepan-1-yl (gg), wherein z is 1 and $R^4$ is —$CON(R')_2$. In another embodiment, $R^1$ and $R^2$, taken together is optionally substituted azepan-1-yl (gg), wherein z is 1 and $R^4$ is —$SO_2N(R')_2$. In another embodiment, $R^1$ and $R^2$, taken together is optionally substituted azepan-1-yl (gg), wherein z is 1 and $R^4$ is —$COR'$.

In yet another embodiment, $R^1$ and $R^2$, taken together is optionally substituted azocan-1-yl (hh), wherein z is 1 or 2 and at least one occurrence of $R^4$ is —$SOR'$, —$CON(R')_2$, —$SO_2N(R')_2$, —$COR'$, or —$COOR'$. In another embodiment, $R^1$ and $R^2$, taken together is optionally substituted azocan-1-yl (hh), wherein z is 1 and $R^4$ is —$SOR'$. In another embodiment, $R^1$ and $R^2$, taken together is optionally substituted azocan-1-yl (hh), wherein z is 1 and $R^4$ is —$COOR'$. In another embodiment, $R^1$ and $R^2$, taken together is optionally substituted azocan-1-yl (hh), wherein z is 1 and $R^4$ is —$CON(R')_2$. In another embodiment, $R^1$ and $R^2$, taken together is optionally substituted azocan-1-yl (hh), wherein z is 1 and $R^4$ is —$SO_2N(R')_2$. In another embodiment, $R^1$ and $R^2$, taken together is optionally substituted azocan-1-yl (hh), wherein z is 1 and $R^4$ is —$COR'$.

In one embodiment, $R^3$ is hydrogen. In one embodiment, $R^3$ is independently halogen, CN, $NO_2$, —$N(R')_2$, —$CH_2N(R')_2$, —$OR'$, —$CH_2OR'$, —$SR'$, —$CH_2SR'$, —$COOR'$, —$NRCOR'$, —$CON(R')_2$, —$OCON(R')_2$, $COR'$, —$NHCOOR'$, —$SO_2R'$, —$SO_2N(R')_2$, or an optionally substituted group selected from $C_1$-$C_6$aliphatic, aryl, heteroaryl, cycloaliphatic, heterocycloaliphatic, aryl$C_1$-$C_6$alkyl, heteroaryl$C_1$-$C_6$alkyl, cycloaliphatic$C_1$-$C_6$alkyl, or heterocycloaliphatic$C_1$-$C_6$alkyl.

In yet another embodiment, each occurrence of $R^3$ is independently Cl, Br, F, $CF_3$, —$OCF_3$, Me, Et, CN, —COOH, —$NH_2$, —$N(CH_3)_2$, —$N(Et)_2$, —$N(iPr)_2$, —$O(CH_2)_2OCH_3$, —$CONH_2$, —$COOCH_3$, —OH, —$OCH_3$, —$OCH_2CH_3$, —$CH_2OH$, —$NHCOCH_3$, —$NHCOCH(CH_3)_2$, —$SO_2NH_2$, —$CONH$(cyclopropyl), —$CONHCH_3$, —$CONHCH_2CH_3$, or an optionally substituted group selected from piperidinyl, piperizinyl, morpholino, phenyl, phenyloxy, benzyl, or benzyloxy.

In another embodiment, each occurrence of $R^3$ is independently halogen, CN, optionally substituted $C_1$-$C_6$alkyl, $OR'$, $N(R')_2$, $CON(R')_2$, or $NRCOR'$.

In yet another embodiment, each $R^3$ is independently —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In yet another embodiment, each $R^3$ is independently —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In another embodiment, $R^3$ is independently selected —Cl, —CH$_3$, —CH$_2$CH$_3$, —F, —CF$_3$, —OCF$_3$, —OCH$_3$, or —OCH$_2$CH$_3$.

In yet other embodiments, $R^3$ is independently selected from —Cl, —CH$_3$, —CH$_2$CH$_3$, —F, —CF$_3$, —OCF$_3$, —OCH$_3$, or —OCH$_2$CH$_3$.

In another embodiment, $R^3$ is —CON(R')$_2$, or —NRCOR'.

In one embodiment, y is 0-5. In another embodiment, y is 0. Or, y is 1-3. In another embodiment, y is 1-2. Or, y is 1.

In one embodiment, $R^5$ is independently halogen, CN, NO$_2$, —N(R')$_2$, —CH$_2$N(R')$_2$, —OR', —CH$_2$OR', —SR', —CH$_2$SR', —NRCOR', —CON(R')$_2$, —S(O)$_2$N(R')$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphaticC$_1$-C$_6$alkyl.

In another embodiment, $R^5$ is independently Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy.

In another embodiment, $R^5$ is F. Or, $R^5$ is OR'. In one embodiment, $R^5$ is OH.

In one embodiment, the present invention provides a compound of formula I-i-A, formula I-ii-A, or formula I-iii-A:

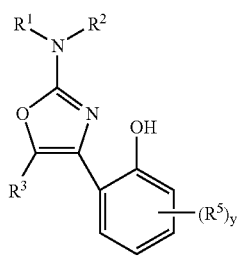

I-i-A

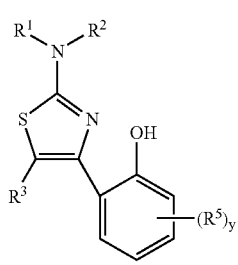

I-ii-A

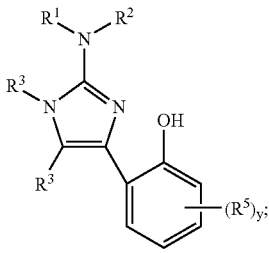

I-iii-A wherein $R^1$, $R^2$, $R^3$, $R^5$, and y are as defined above.

In one embodiment, the present invention provides a compound of formula I-iv-A, formula I-v-A, or formula I-vi-A:

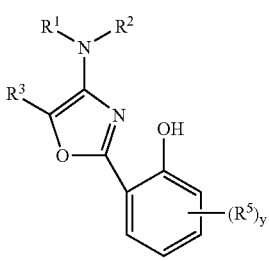

I-iv-A

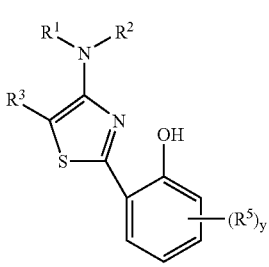

I-v-A

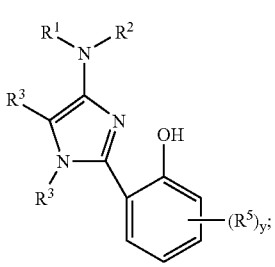

I-vi-A wherein $R^1$, $R^2$, $R^3$, $R^5$, and y are as defined above.

In one embodiment, the present invention provides a compound of formula I-vii-A, formula I-viii-A, or formula I-ix-A:

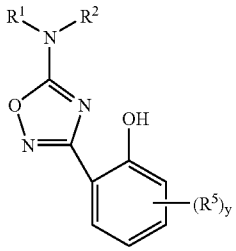
I-vii-A

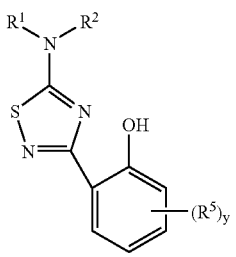
I-viii-A

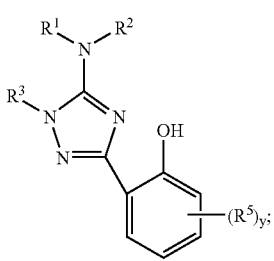
I-ix-A wherein $R^1$, $R^2$, $R^3$, $R^5$, and y are as defined above.

In one embodiment, the present invention provides a compound of formula I-x-A, formula I-xi-A, or formula I-xii-A:

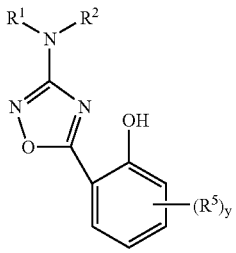
I-x-A

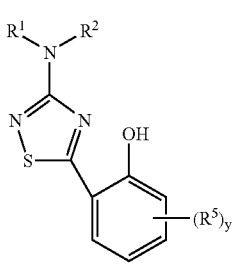
I-xi-A

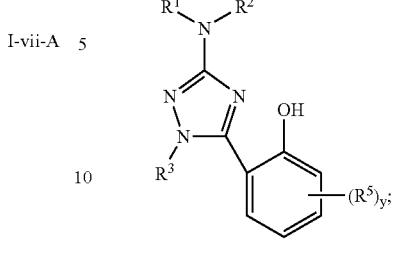
I-xii-A wherein $R^1$, $R^2$, $R^3$, $R^5$, and y are as defined above.

In one embodiment, the present invention provides a compound of formula I-xiii-A:

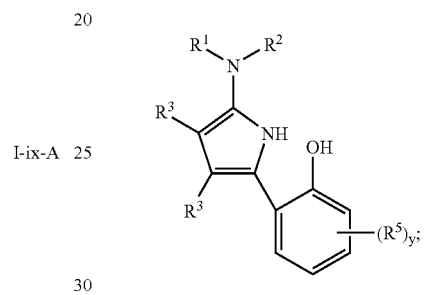
I-xiii-A wherein $R^1$, $R^2$, $R^3$, $R^5$, and y are as defined above.

In one embodiment, y is 0.

In another embodiment, $R^3$ is hydrogen.

In another embodiment, $R^3$ is X—$R^Q$ and X is a C1-C6 alkylidene. In another embodiment, X is a C1-C4 alkylidene. Or, X is —CH$_2$—.

In one embodiment, $R^Q$ is independently selected from —R', —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$.

In another embodiment $R^Q$ is R'.

In one embodiment, $R^3$ is independently halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, arylC$_1$-C$_6$alkyl, heteroarylC$_1$-C$_6$alkyl, cycloaliphaticC$_1$-C$_6$alkyl, or heterocycloaliphaticC$_1$-C$_6$alkyl.

In yet another embodiment, each occurrence of $R^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from piperidinyl, piperazinyl, morpholino, phenyl, phenyloxy, benzyl, or benzyloxy.

In another embodiment, each occurrence of $R^3$ is independently halogen, CN, optionally substituted C$_1$-C$_6$alkyl, OR', N(R')$_2$, CON(R')$_2$, or NRCOR'.

In yet another embodiment, each $R^3$ is independently —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In yet another embodiment, each $R^3$ is independently —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In another embodiment, $R^3$ is independently selected —Cl, —CH$_3$, —CH$_2$CH$_3$, —F, —CF$_3$, —OCF$_3$, —OCH$_3$, or —OCH$_2$CH$_3$.

In yet other embodiments, $R^3$ is independently selected from —Cl, —CH$_3$, —CH$_2$CH$_3$, —F, —CF$_3$, —OCF$_3$, —OCH$_3$, or —OCH$_2$CH$_3$.

In another embodiment, $R^3$ is —CON(R')$_2$, or —NRCOR'.

In one embodiment, the present invention provides a compound of formula I-i-B, formula I-ii-B, or formula I-iii-B:

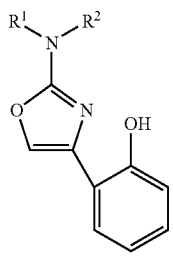

I-i-B

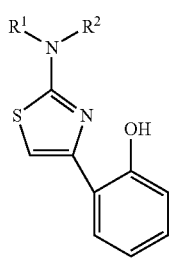

I-ii-B

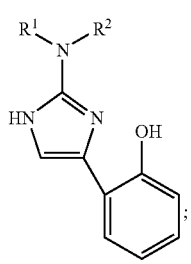

I-iii-B wherein $R^1$, $R^2$, $R^3$, $R^5$, and y are as defined above.

In one embodiment, the present invention provides a compound of formula I-iv-B, formula I-v-B, or formula I-vi-B:

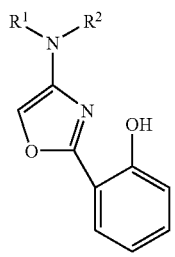

I-iv-B

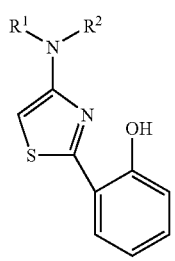

I-v-B

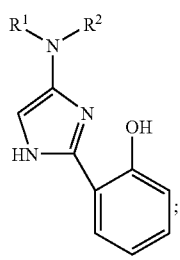

I-vi-B wherein $R^1$, $R^2$, $R^3$, $R^5$, and y are as defined above.

In one embodiment, the present invention provides a compound of formula I-vii-B, formula I-viii-B, or formula I-ix-B:

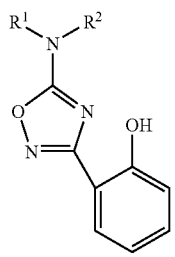

I-vii-B

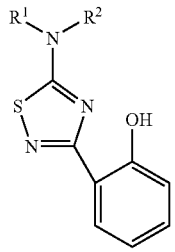

I-viii-B

-continued

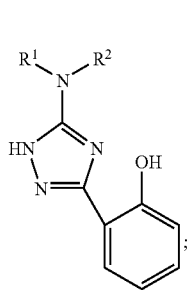
I-ix-B wherein $R^1$, $R^2$, $R^3$, $R^5$, and y are as defined above.

In one embodiment, the present invention provides a compound of formula I-x-B, formula I-xi-B, or formula I-xii-B:

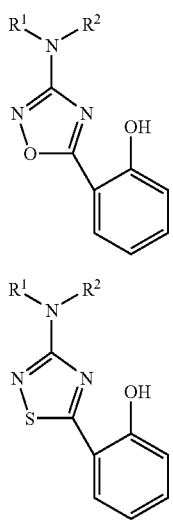
I-x-B

I-xi-B

-continued

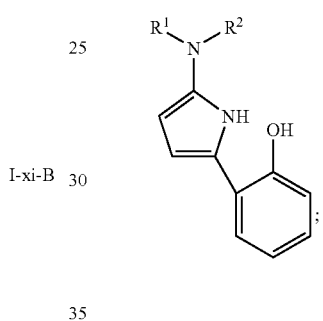
I-xii-B wherein $R^1$, $R^2$, $R^3$, $R^5$, and y are as defined above.

In one embodiment, the present invention provides a compound of formula I-xiii-B:

I-xiii-B wherein $R^1$, $R^2$, $R^3$, $R^5$, and y are as defined above.

Exemplary compounds of formula I are shown below in Table 1:

TABLE 1

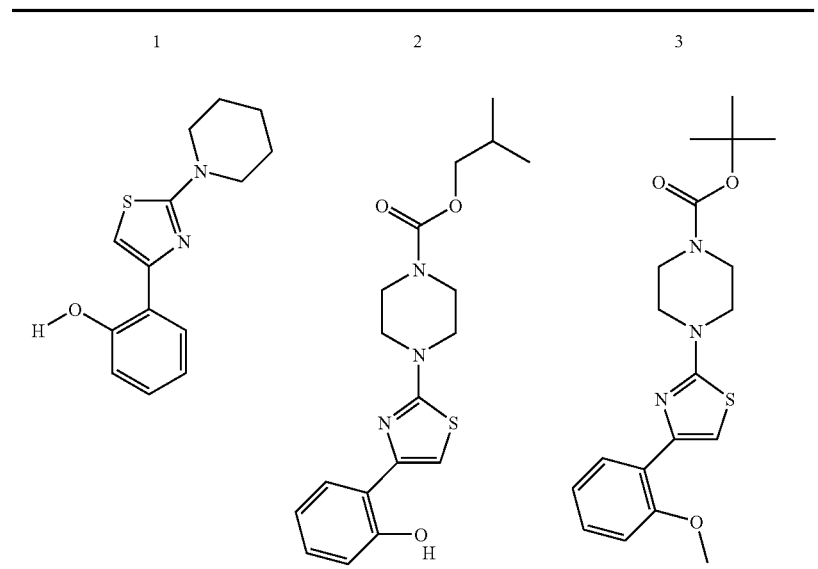

| 1 | 2 | 3 |

TABLE 1-continued
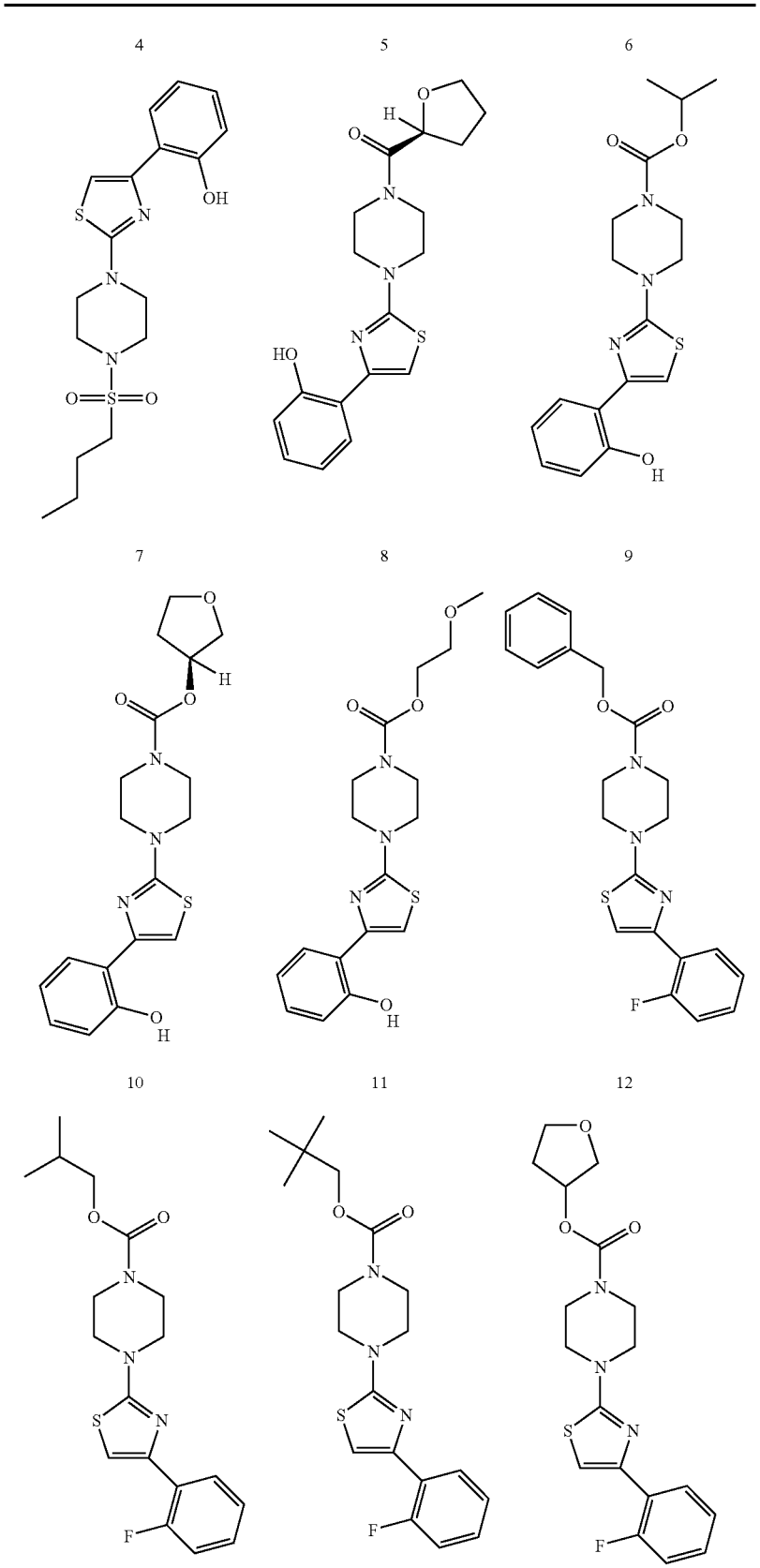

TABLE 1-continued
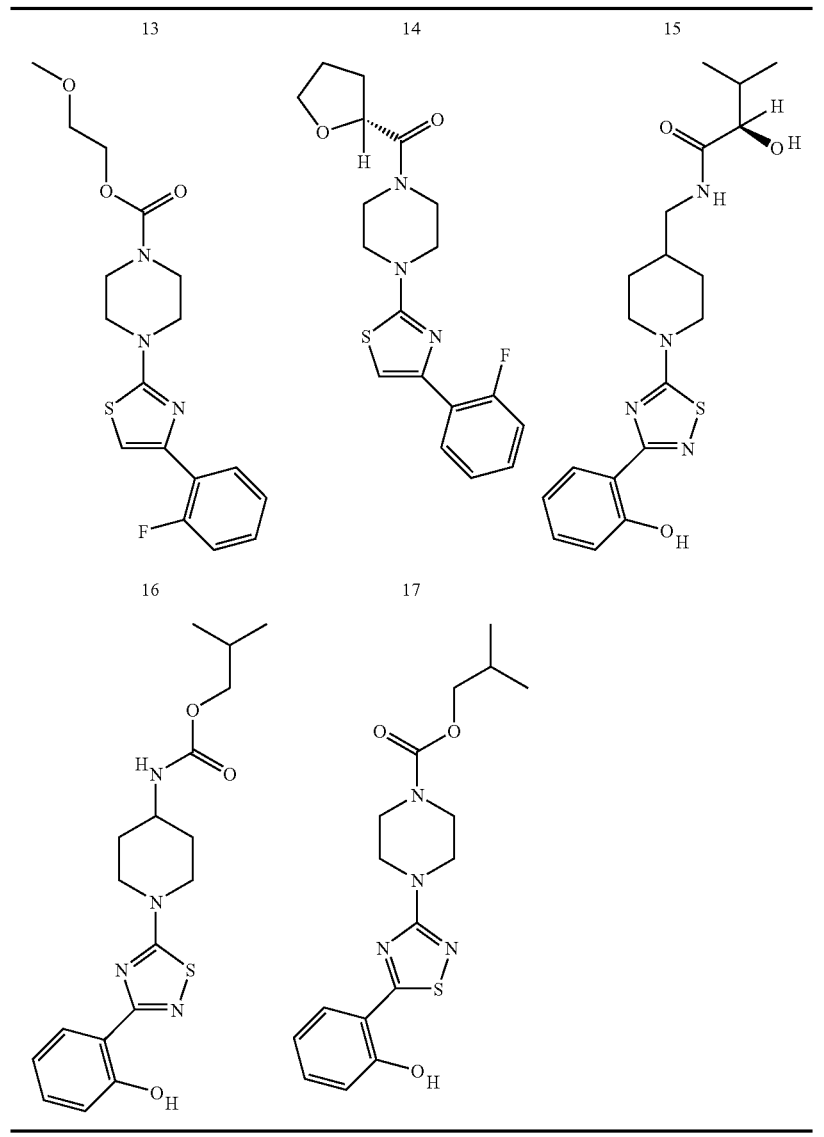
4. General Synthetic Methodology
The compounds of this invention may be prepared in general by methods known to those skilled in the art. Exemplary synthetic routes are illustrated below for the preparation of the compounds of the present invention.
Compounds of formula I-i may be prepared as illustrated below in Scheme 1.
Scheme 1:
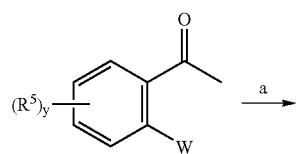
-continued
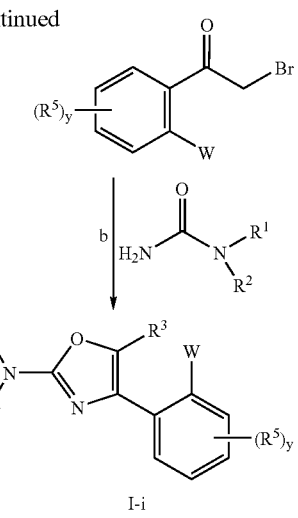

Conditions: a) Br$_2$, MeOH; b) 1. Et$_3$N, DMF, heat

Compounds of formula I-i may also be prepared as illustrated below in Scheme 1a.

Scheme 1a:

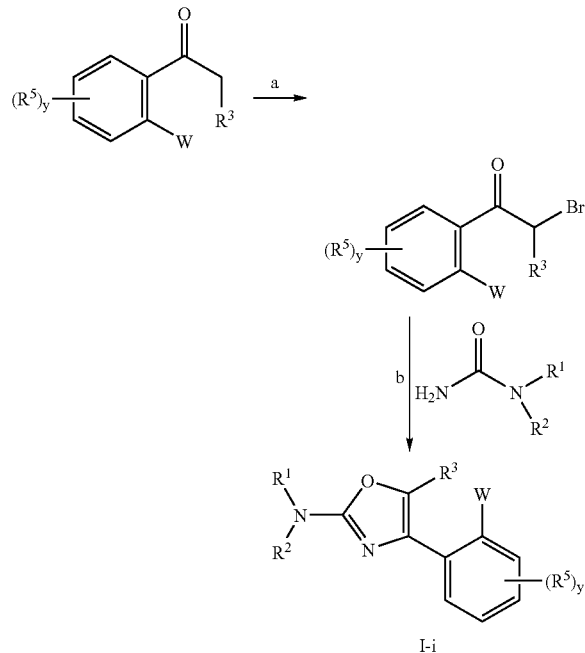

Conditions: a) Br$_2$, MeOH; b) Et$_3$N, DMF, heat

Compounds of formula I-ii may be prepared as illustrated below in Scheme 2.

Scheme 2:

Conditions: a) Et$_3$N, THF, heat

Compounds of formula I-ii may also be prepared as illustrated below in Scheme 2a-1.

Scheme 2a-1:

Conditions: a) Et$_3$N, THF, heat

Compounds of formula I-iii may be prepared as illustrated below in Scheme 3.

Scheme 2a: Compounds of Formula I-ii(ii)

PG = Boc, Bn, Bz, R$_3$Si, etc.

Conditions: a) Et$_3$N, THF, heat; b) deprotect: 1:1 TFA/DCM, rt, for Boc; H$_2$, Pd/C for Bn; NaOH for Bz, TBAF for R$_3$Si, etc.; c) For acid halides, DCM or THF, Et$_3$N; for carboxylic acids, EDC, HOBt, Et$_3$N, DMF; for X=OR', THF or DMF, heat.

Scheme 2b: Compounds of Formula I-ii(jj)

Scheme 2c: Compounds of Formula I-ii(kk)

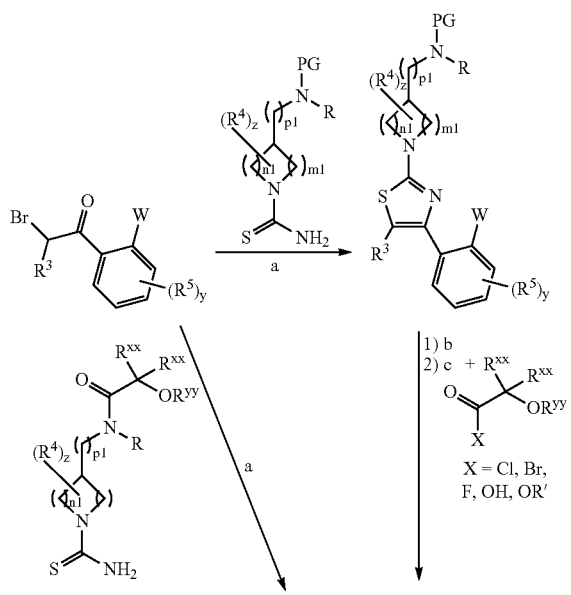
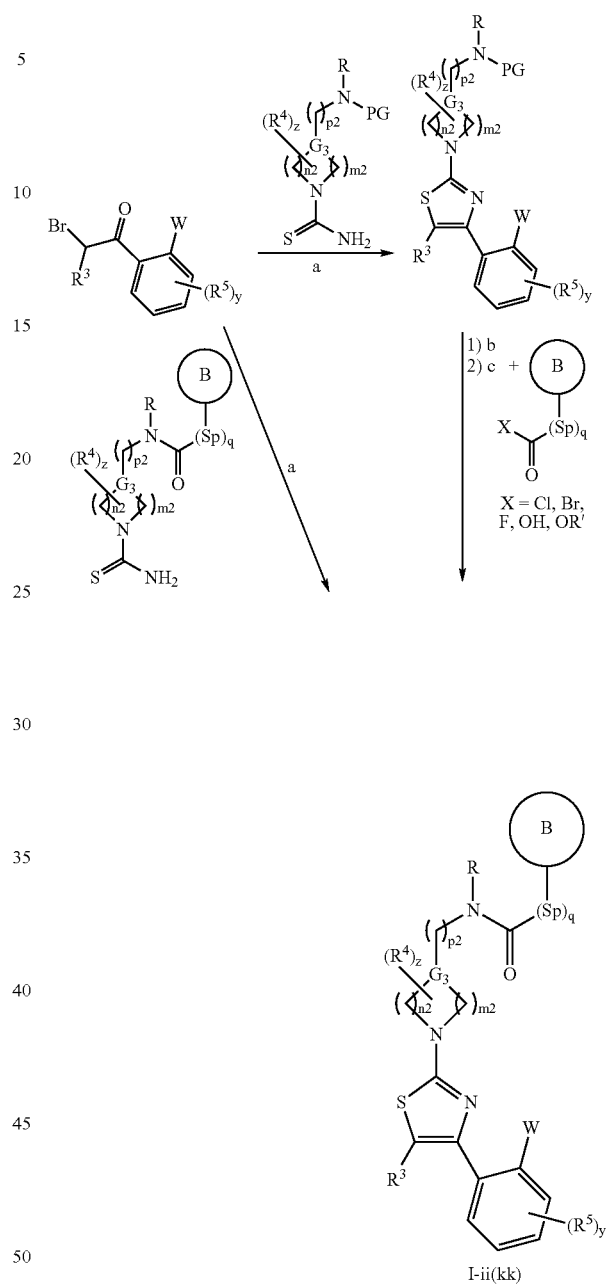

PG = Boc, Bn, Bz, R$_3$Si, etc.

PG = Boc, Bn, Bz, R$_3$Si, etc.

Conditions: a) Et$_3$N, THF, heat; b) deprotect: 1:1 TFA/DCM, rt, for Boc; H$_2$, Pd/C for Bn; NaOH for Bz, TBAF for R$_3$Si, etc.; c) For acid halides, DCM or THF, Et$_3$N; for carboxylic acids, EDC, HOBt, Et$_3$N, DMF; for X=OR', THF or DMF, heat.

Conditions: a) Et$_3$N, THF, heat; b) deprotect: 1:1 TFA/DCM, rt, for Boc; H$_2$, Pd/C for Bn; NaOH for Bz, TBAF for R$_3$Si, etc.; c) For X=Cl, Br, or F, DCM or THF, Et$_3$N; for carboxylic acids, EDC, HOBt, Et$_3$N, DMF; for X=OR', THF or DMF, heat.

Scheme 2d: Compounds of Formula I-ii(ll)

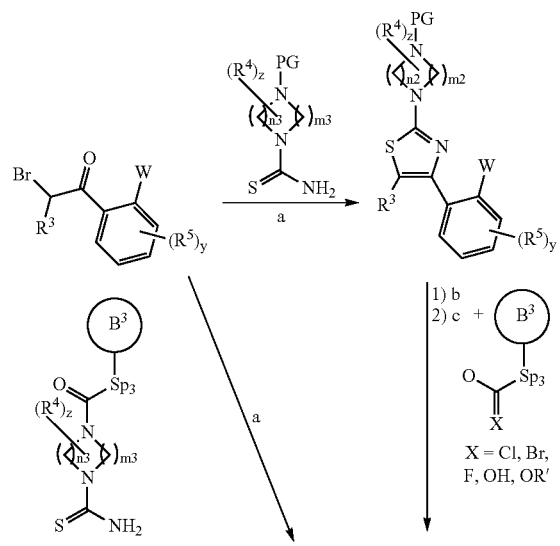

Scheme 2e: Compounds of Formula I-ii(mm)

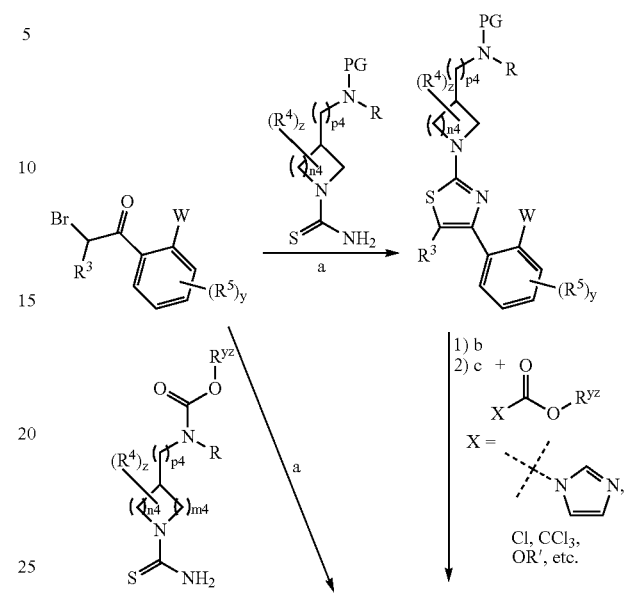

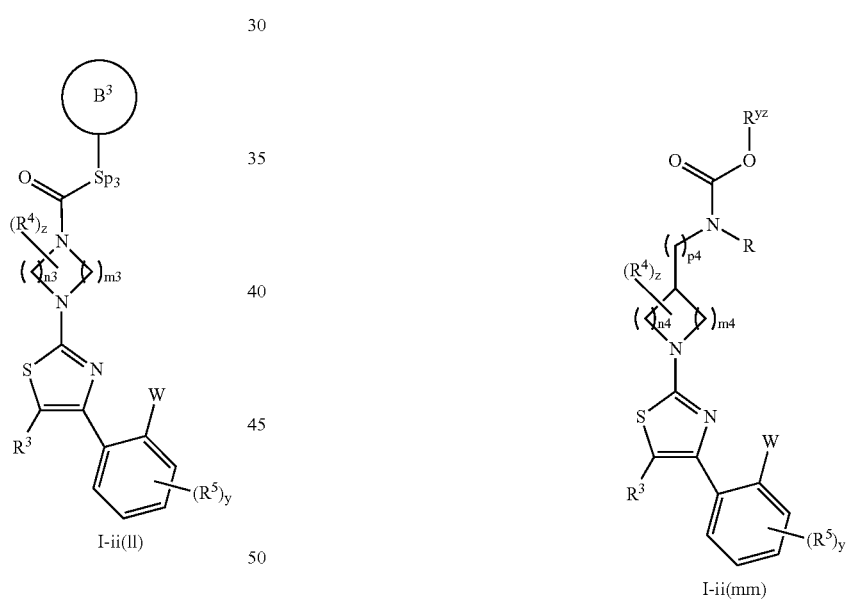

PG = Boc, Bn, Bz, R$_3$Si, etc.

PG = Boc, Bn, Bz, R$_3$Si, etc.

Conditions: a) Et$_3$N, THF, heat; b) deprotect: 1:1 TFA/DCM, rt, for Boc; H$_2$, Pd/C for Bn; NaOH for Bz, TBAF for R$_3$Si, etc.; c) For X=Cl, Br, or F, DCM or THF, Et$_3$N; for carboxylic acids, EDC, HOBt, Et$_3$N, DMF; for X=OR', THF or DMF, heat.

Conditions: a) Et$_3$N, THF, heat; b) deprotect: 1:1 TFA/DCM, rt, for Boc; H$_2$, Pd/C for Bn; NaOH for Bz, TBAF for R$_3$Si, etc.; c) For X=Cl, CCl$_3$, or imidazolyl, DCM or THF, Et$_3$N; for carboxylic acids, EDC, HOBt, Et$_3$N, DMF; for X=OR', THF or DMF, heat.

Scheme 2f: Compounds of Formula I-ii(nn)

Scheme 2g: Compounds of Formula I-ii(pp)

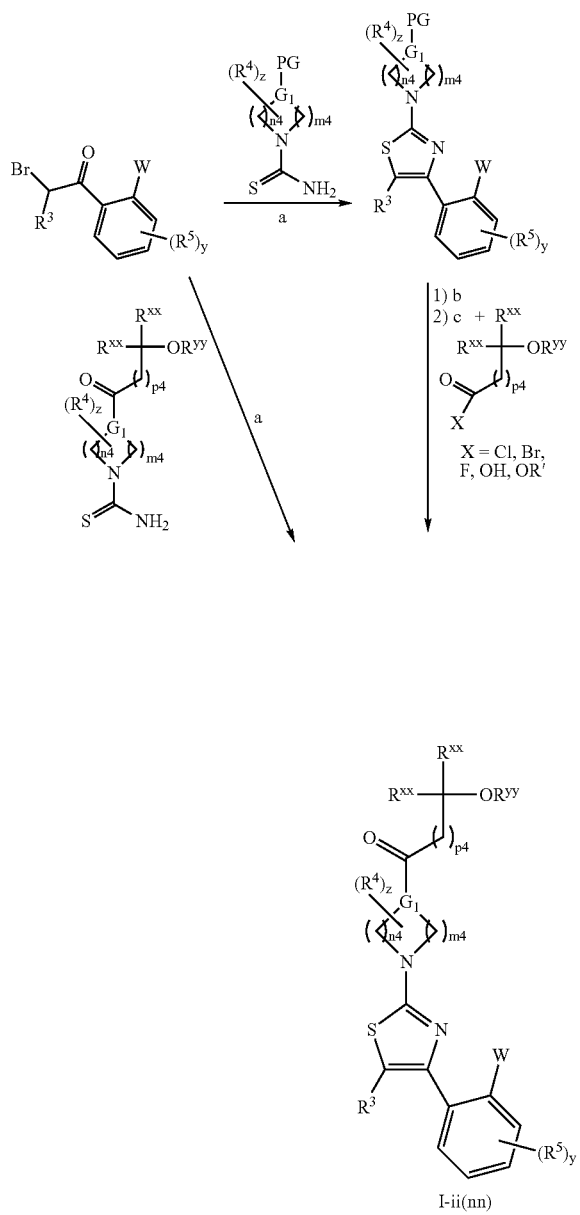

I-ii(nn)

PG = Boc, Bn, Bz, R$_3$Si, etc.

Conditions: a) Et$_3$N, THF, heat; b) deprotect: 1:1 TFA/DCM, rt, for Boc; H$_2$, Pd/C for Bn; NaOH for Bz, TBAF for R$_3$Si, etc.; c) For acid halides, DCM or THF, Et$_3$N; for carboxylic acids, EDC, HOBt, Et$_3$N, DMF; for X=OR', THF or DMF, heat.

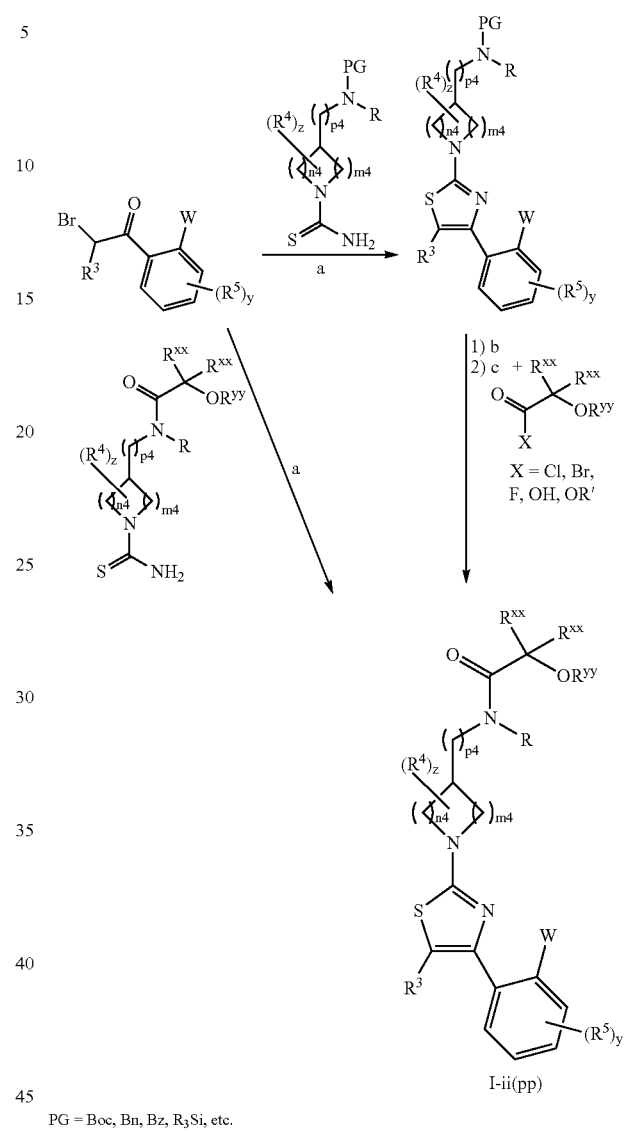

I-ii(pp)

PG = Boc, Bn, Bz, R$_3$Si, etc.

Conditions: a) Et$_3$N, THF, heat; b) deprotect: 1:1 TFA/DCM, rt, for Boc; H$_2$, Pd/C for Bn; NaOH for Bz, TBAF for R$_3$Si, etc.; c) For acid halides, DCM or THF, Et$_3$N; for carboxylic acids, EDC, HOBt, Et$_3$N, DMF; for X=OR', THF or DMF, heat.

Compounds of formula I-iii may be prepared as illustrated below in Scheme 3.

Scheme 3:

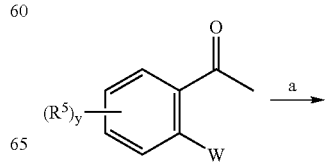

-continued

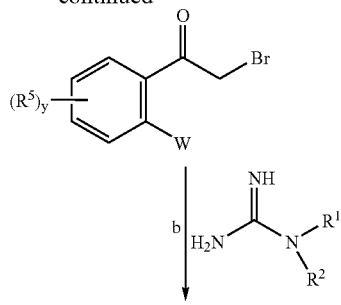

b | 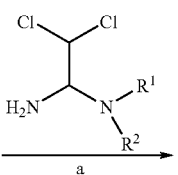

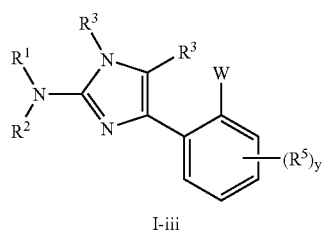

I-iii

Conditions: a) Br$_2$, MeOH; b) Et$_3$N, DMF, heat, 10 h

Compounds of formula I-iii may also be prepared as illustrated below in Scheme 3a.

Scheme 3a: Compounds of formula I-iii

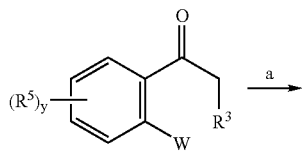

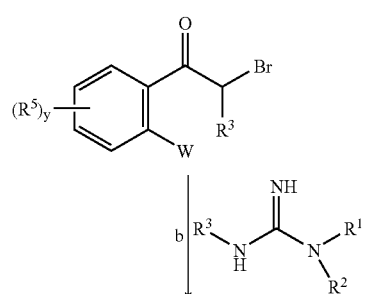

b | 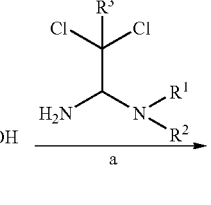

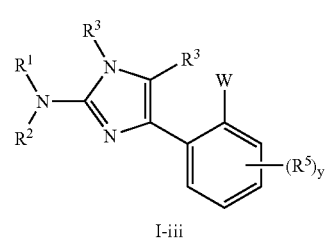

I-iii

Conditions: a) Br$_2$, MeOH; b) Et$_3$N, DMF, heat

Compounds of formula I-iv may be prepared as illustrated below in Scheme 4.

Scheme 4:

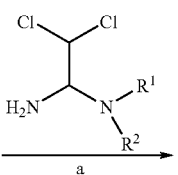

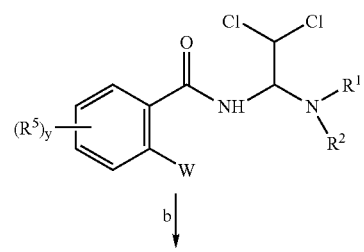

I-iv

Conditions: a) HBTU, DIEA, DMF; b) NaOMe-MeOH-THF

Compounds of formula I-iv may be prepared as illustrated below in Scheme 4a.

Scheme 4a: Compounds of formula I-iv

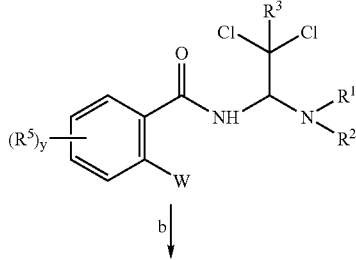

b

-continued

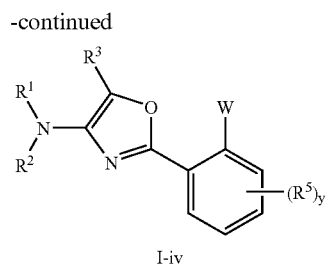

I-iv

Conditions: a) HBTU, DIEA, DMF; b) NaOMe, MeOH, THF

Compounds of formula I-v may be prepared as illustrated below in Scheme 5.

Scheme 5:

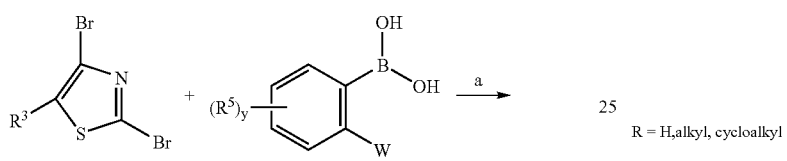

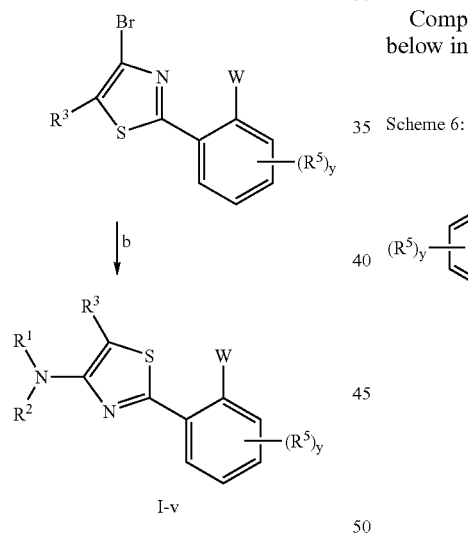

I-v

Conditions: a) PdCl$_2$(dppf), Na$_2$CO$_3$, Tol, 140° C.; b) HNR$^1$R$^2$, DMF heat Compounds of formula I-v may also be prepared as illustrated below in Scheme 5a.

Scheme 5a:

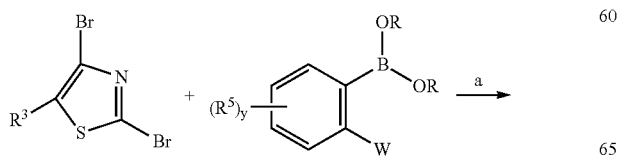

-continued

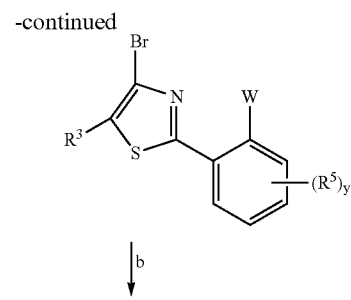

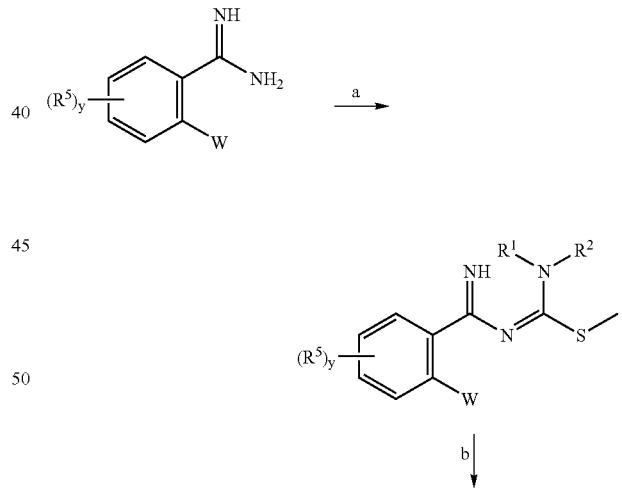

I-v

R = H, alkyl, cycloalkyl

Conditions: a) PdCl$_2$(dppf), Na$_2$CO$_3$, toluene, 140° C.; b) HNR$^1$R$^2$, DMF, heat.

Compounds of formula I-vi may be prepared as illustrated below in Scheme 6.

Scheme 6:

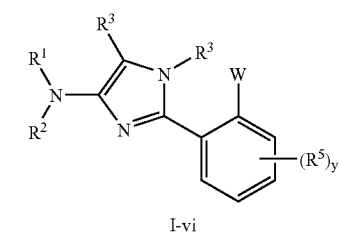

I-vi

Conditions: a) p-TsOH, CH$_2$Cl$_2$; b) Zn(Cu), CH$_2$I$_2$, THF, heat

Compounds of formula I-vi may also be prepared as illustrated below in Scheme 6a.

Scheme 6a:

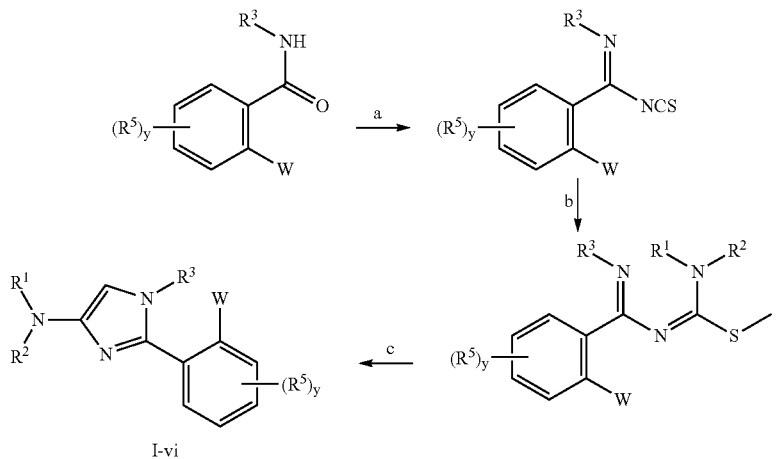

Conditions: a) i. PCl$_5$, CH$_2$Cl$_2$; ii. NaSCN, acetone; b) i. HNR$^1$R$^2$, acetone; ii. MeI; c) Zn(Cu), CH$_2$I$_2$, 12, THF, heat.

Compounds of formula I-vii may be prepared as illustrated below in Scheme 7.

Scheme 7:

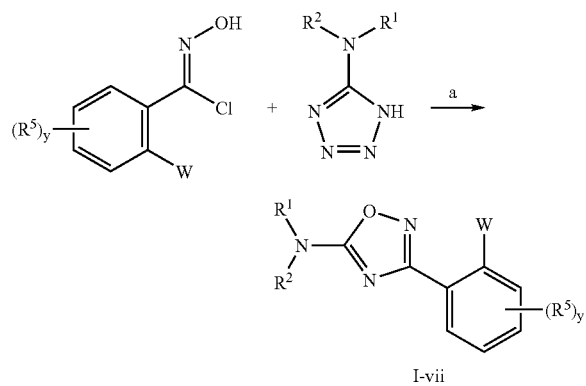

Conditions: a) Et$_3$N, Dioxane-Ethanol, heat

Compounds of formula I-vii may also be prepared as illustrated below in Scheme 7a.

Scheme 7a:

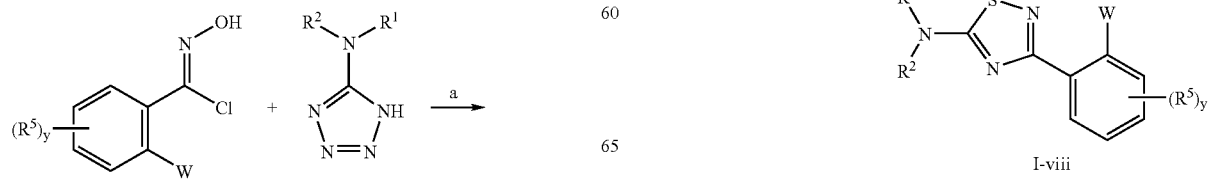

-continued

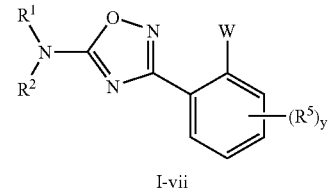

Conditions: a) Et$_3$N, dioxane, ethanol, heat

Compounds of formula I-viii may be prepared as illustrated below in Scheme 8.

Scheme 8:

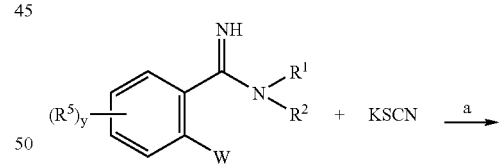

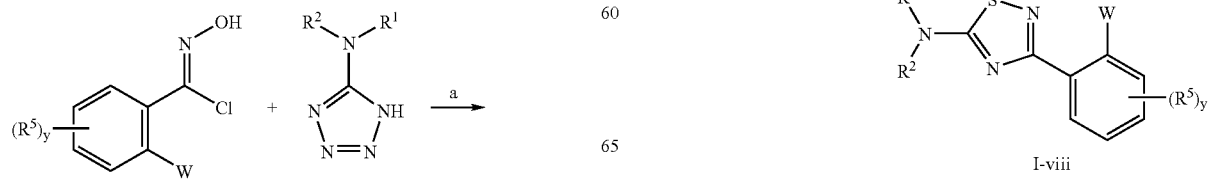

I-viii

Conditions: a) NaOMe, methanol, heat

Compounds of formula I-viii may also be prepared as illustrated below in Scheme 8a.

Scheme 8a:

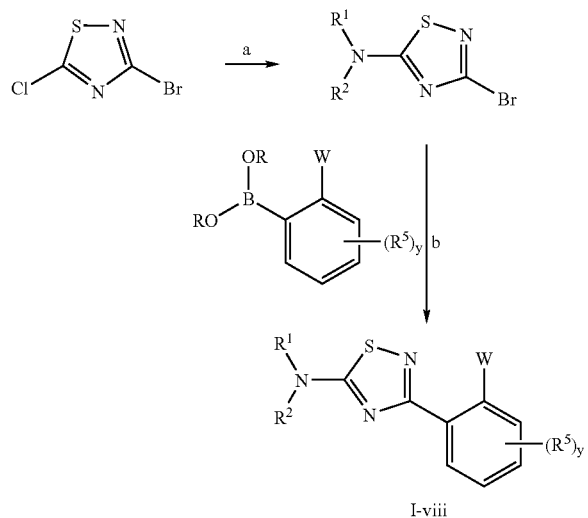

R = H, alkyl, cycloalkyl

Conditions: a) HNR$^1$R$^2$, DMF; b) Pd(Ph$_3$)$_4$, K$_2$CO$_3$, CH$_3$CN, H$_2$O Compounds of formula I-ix may be prepared as illustrated below in Scheme 9.

Scheme 9:

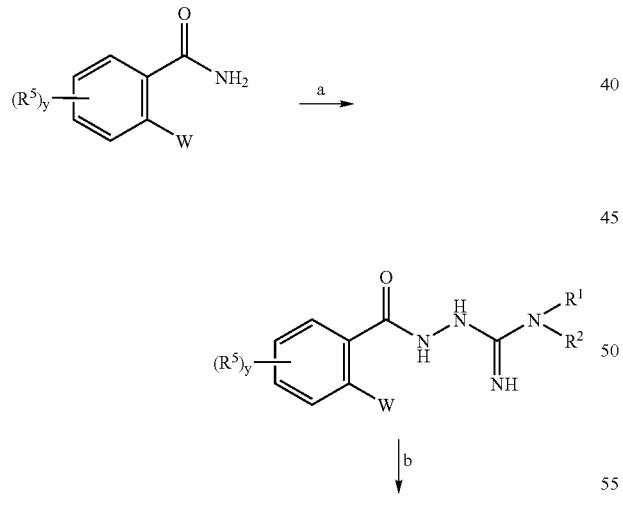

Conditions: a) Nitrosoguanidine, THF; b) 220° C.

Compounds of formula I-ix may be prepared as illustrated below in Scheme 9a.

Scheme 9a:

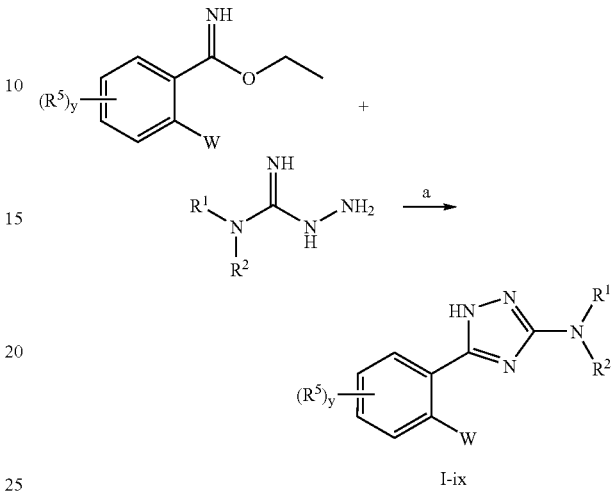

Conditions: a) NaOH, ethanol, H$_2$O, heat

Compounds of formula I-x may be prepared as illustrated below in Scheme 10.

Scheme 10:

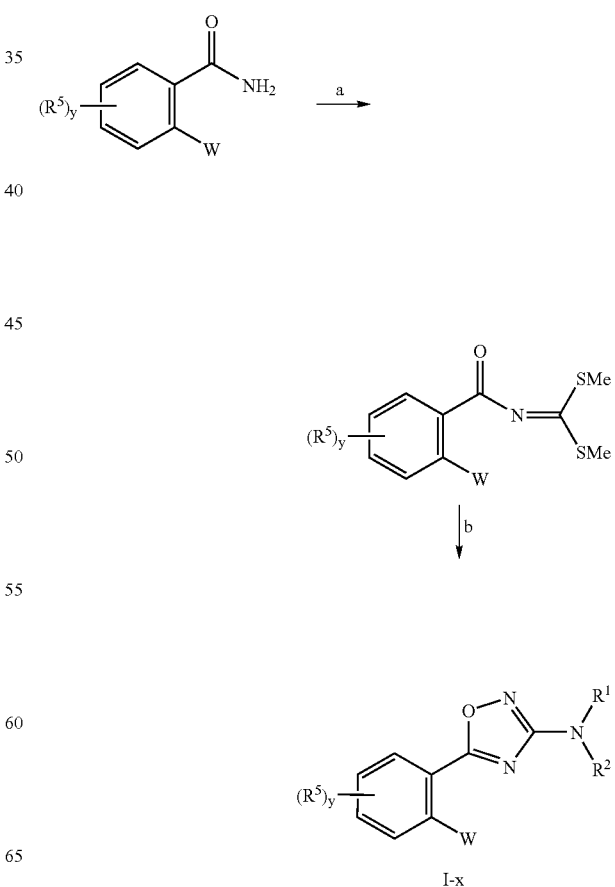

Conditions: a) NaH, THF, MeI, CS$_2$; b) NH$_2$OH, HNR$^1$R$^2$

Compounds of formula I-xi may be prepared as illustrated below in Scheme 11.

Scheme 11:

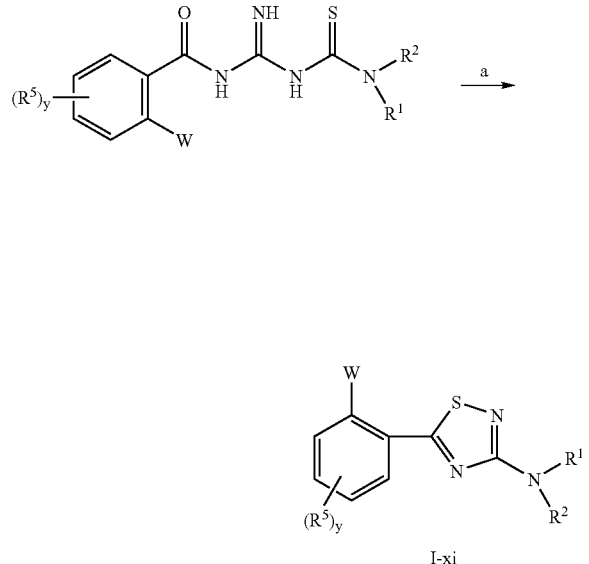

I-xi

Conditions: a) H$_2$O$_2$, ethanol-H$_2$O, heat

Compounds of formula I-xi may also be prepared as illustrated below in Scheme 11a.

Scheme 11a:

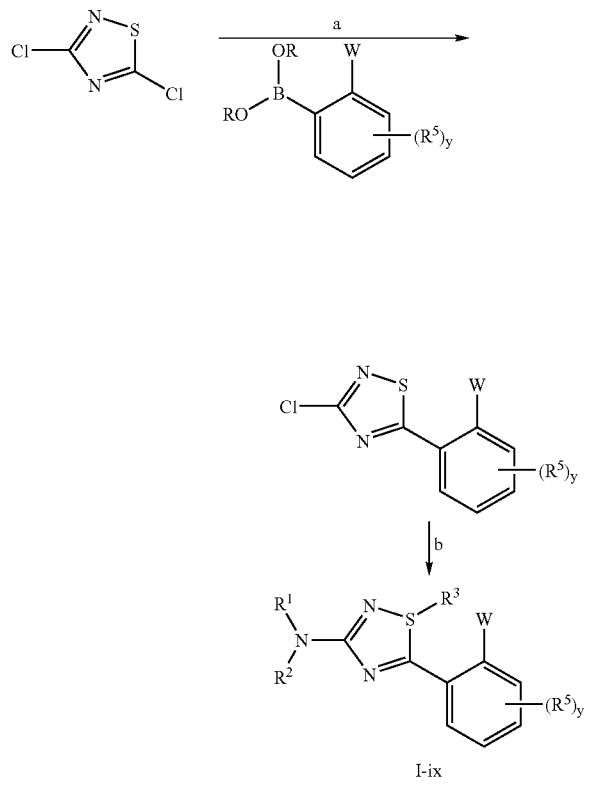

I-ix

R = H, alkyl, cycloalkyl

Conditions: a) Pd(Ph$_3$)$_4$, K$_2$CO$_3$, CH$_3$CN, H$_2$O; b) HNR$^1$R$^2$, DMF Compounds of formula I-xii may be prepared as illustrated below in Scheme 12.

Scheme 12:

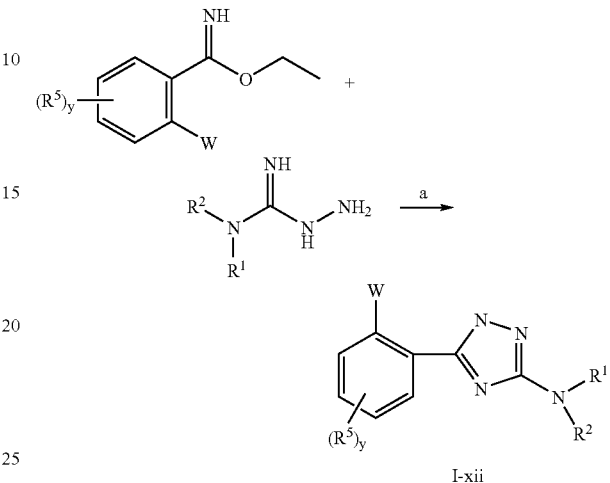

I-xii

Conditions: a) NaOH, ethanol-H$_2$O, heat

Compounds of formula I-xii may also be prepared as illustrated below in Scheme 12a.

Scheme 12a:

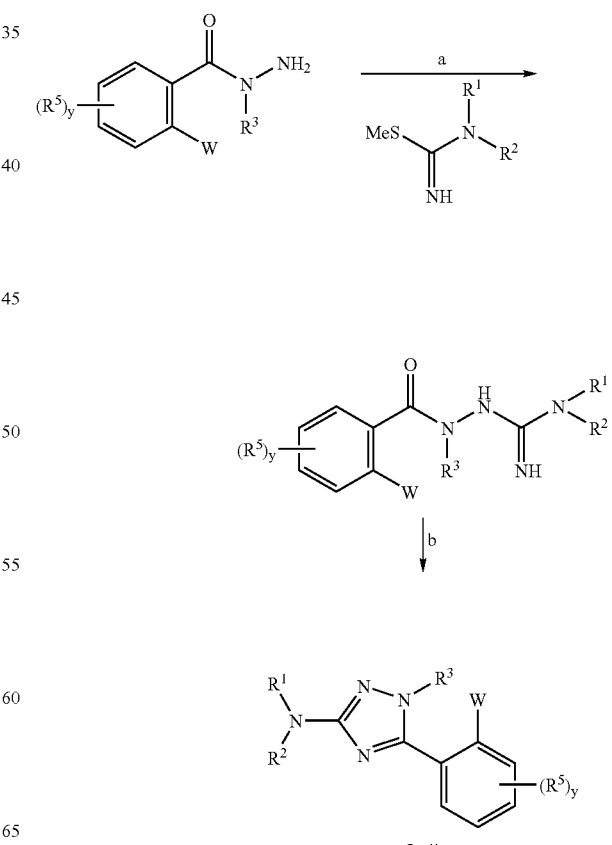

I-xii

Conditions: a) NaOH, H₂O; b) 220° C.

Compounds of formula I-xiii may be prepared as illustrated below in Scheme 13.

Scheme 13:

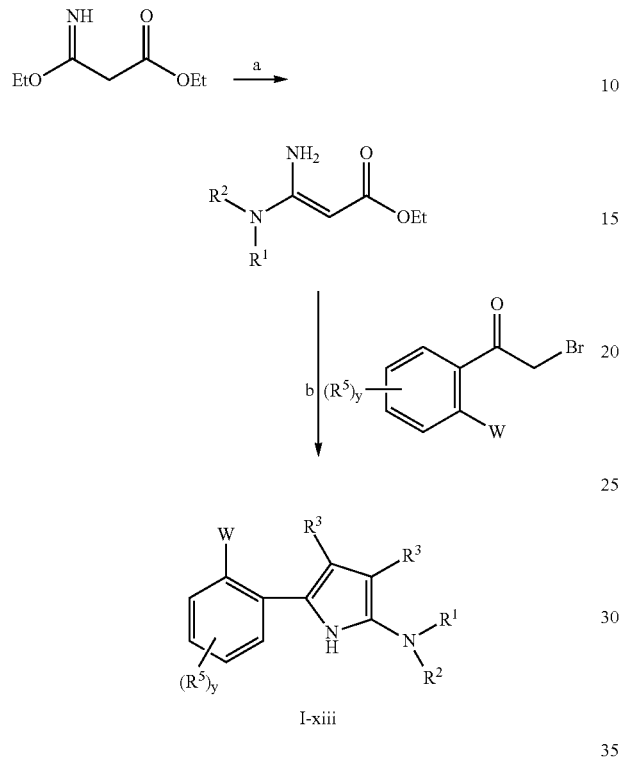

Conditions: a) Et₃NR¹R²NH, DMF; b) Ethanol, 0° C.-25° C.

Compounds of formula I-xiii may also be prepared as illustrated below in Scheme 13a.

Scheme 13a:

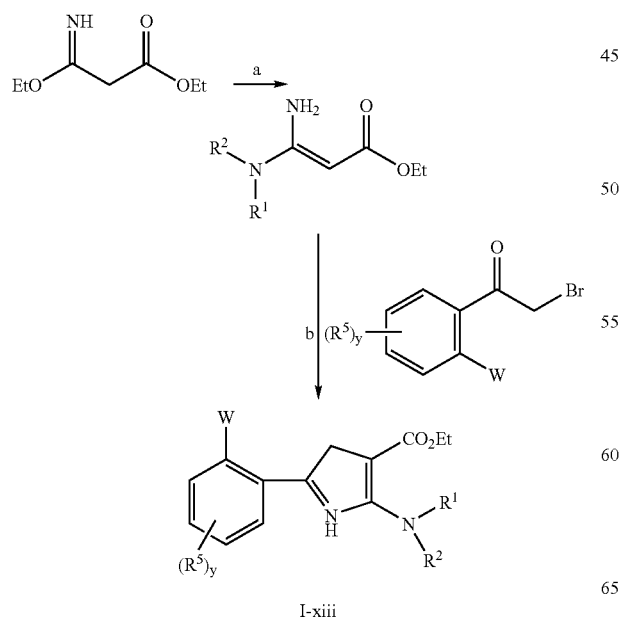

Conditions: a) Et₃N, R¹R²NH, DMF; b) ethanol, 0° C.-25° C.

Compounds of formula I-i-A may be prepared as illustrated below in Scheme A-1.

Scheme A-1:

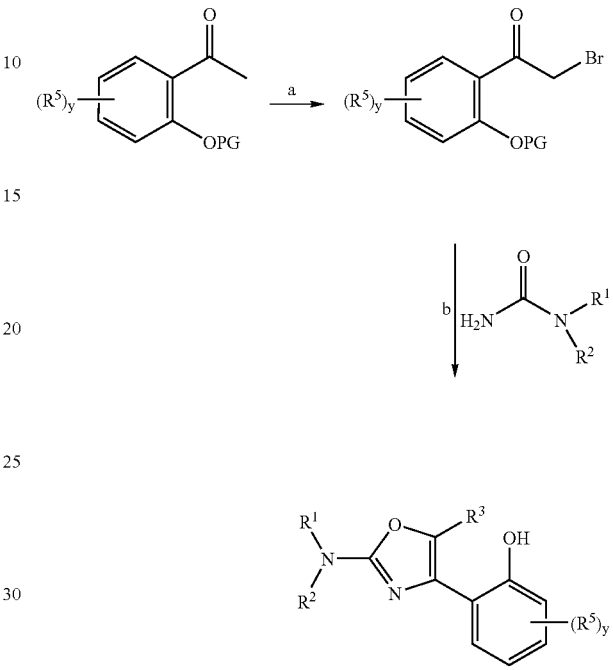

PG = Me, SiR₃, COR, CO₂R, P(O)R₂, SO₂R, etc.

Conditions: a) Br₂, MeOH; b) i. Et₃N, DMF, heat; ii. deprotect

Compounds of formula I-ii-A may be prepared as illustrated below in Scheme A-2.

Scheme A-2:

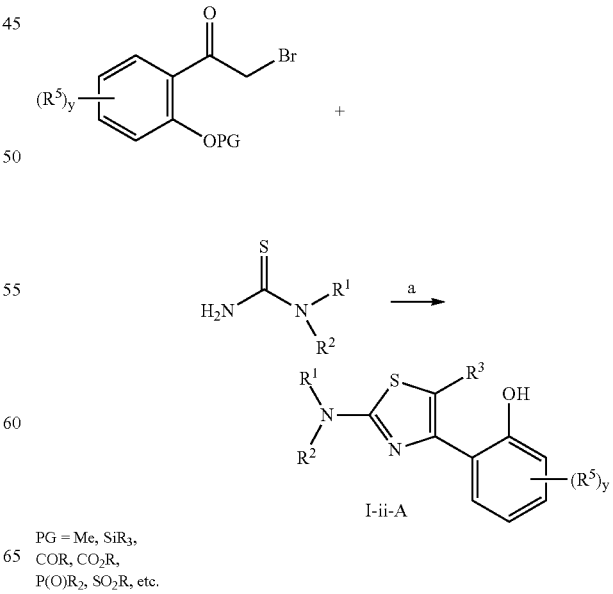

PG = Me, SiR₃, COR, CO₂R, P(O)R₂, SO₂R, etc.

Conditions: a) i. Et₃N, THF, heat; ii. deprotect

Compounds of formula I-ii-A may also be prepared as illustrated below in Scheme A-2-1.

Scheme A-2-1:

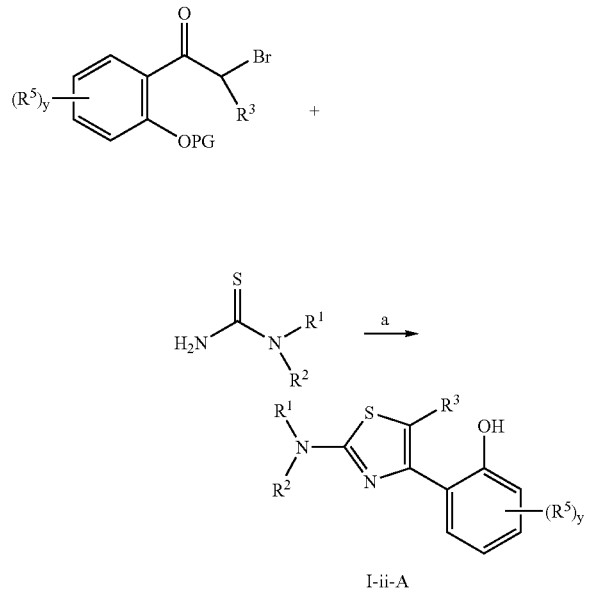

PG = Me, SiR₃,
COR, CO₂R,
P(O)R₂, SO₂R, etc.

Conditions: a) i. Et₃N, THF, heat; ii. Deprotect.

Compounds of formula I-iii-A may be prepared as illustrated below in Scheme A-3.

Scheme A-3:

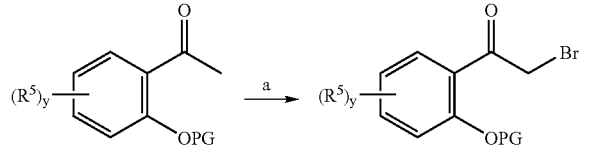

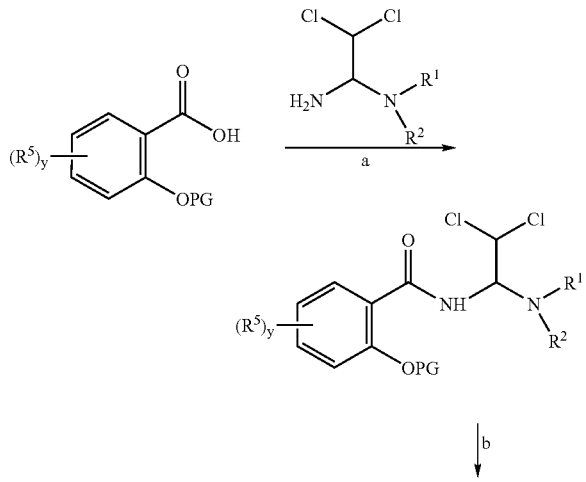

PG = Me, SiR₃,
COR, CO₂R,
P(O)R₂, SO₂R, etc.

Conditions: a) Br₂, MeOH; b) i. Et₃N, DMF, heat, 10 h; ii. deprotect

Compounds of formula I-iii-A may also be prepared as illustrated below in Scheme A-3-1.

Scheme A-3-1:

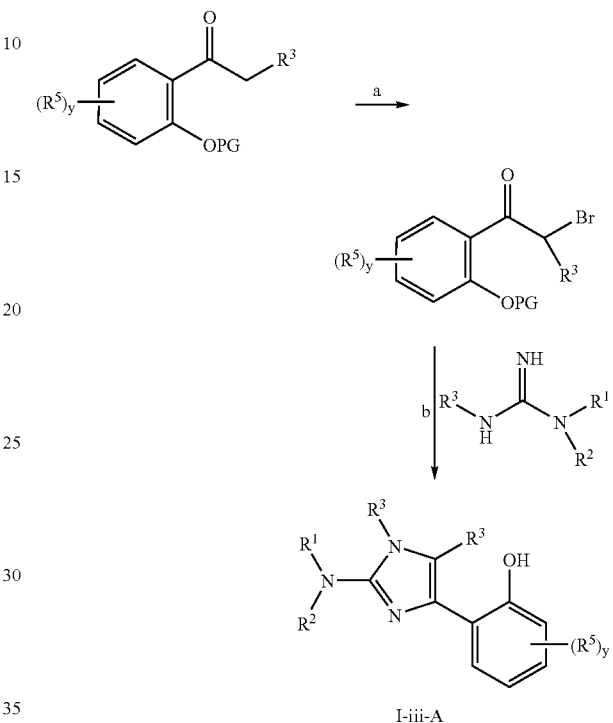

PG = Me, SiR₃,
COR, CO₂R,
P(O)R₂, SO₂R, etc.

Conditions: a) Br₂, MeOH; b) i. Et₃N, DMF, heat; ii. deprotect

Compounds of formula I-iv-A may be prepared as illustrated below in Scheme A-4.

Scheme A-4:

-continued

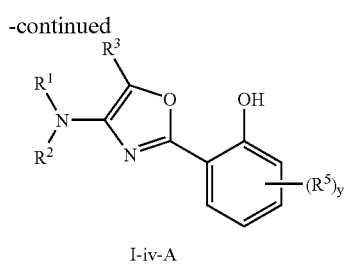

I-iv-A

PG = Me, SiR₃,
COR, CO₂R,
P(O)R₂, SO₂R, etc.

Conditions: a) HBTU, DIEA, DMF; b) i. NaOMe-MeOH-THF; ii. deprotect

Compounds of formula I-iv-A may also be prepared as illustrated below in Scheme A-4-1.

Scheme A-4-1:

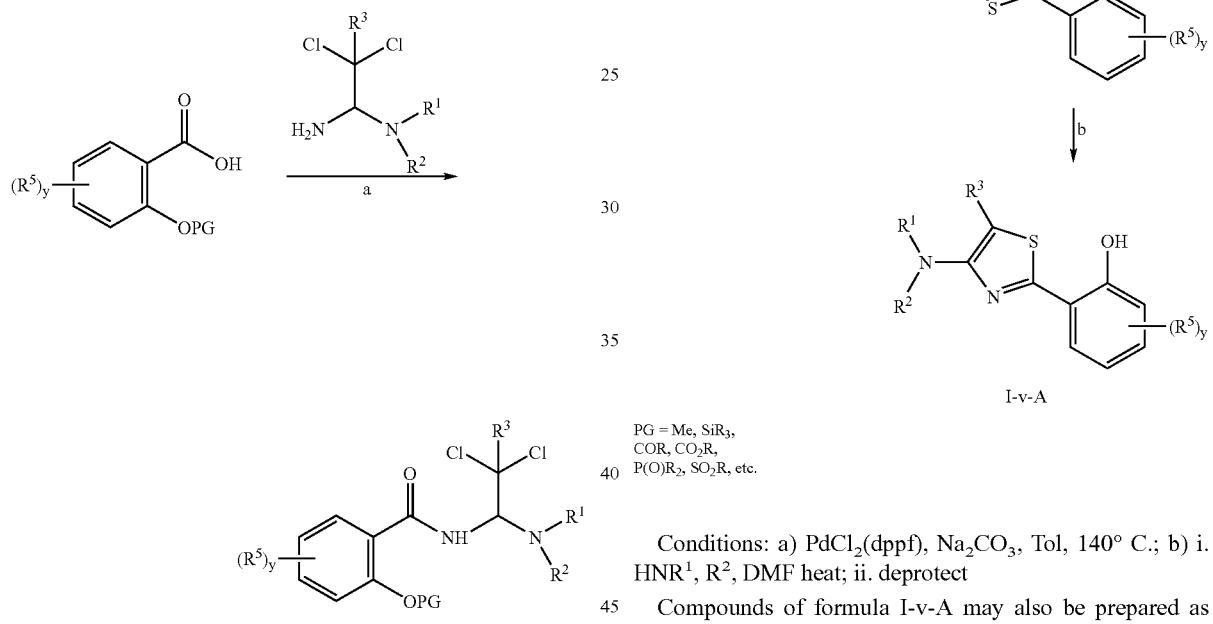

I-iv-A

PG = Me, SiR₃,
COR, CO₂R,
P(O)R₂, SO₂R, etc.

Conditions: a) HBTU, DIEA, DMF; b) i. NaOMe, MeOH, THF; ii. deprotect

Compounds of formula I-v-A may be prepared as illustrated below in Scheme A-5.

Scheme A-5:

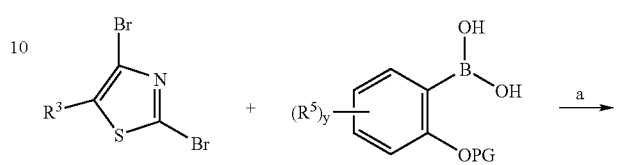

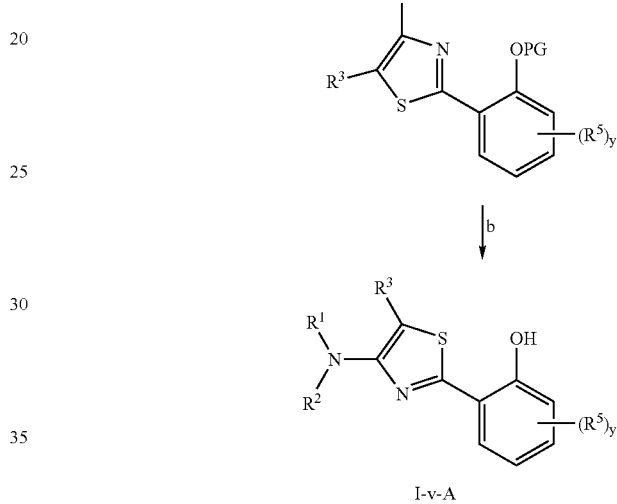

I-v-A

PG = Me, SiR₃,
COR, CO₂R,
P(O)R₂, SO₂R, etc.

Conditions: a) PdCl₂(dppf), Na₂CO₃, Tol, 140° C.; b) i. HNR¹, R², DMF heat; ii. deprotect Compounds of formula I-v-A may also be prepared as illustrated below in Scheme A-5-1.

Scheme A-5-1:

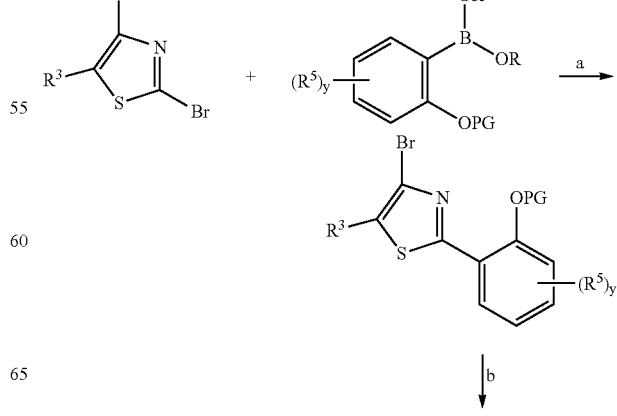

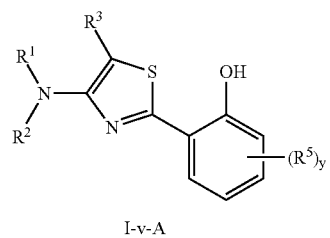

I-v-A

R = H, alkyl, cycloalkyl
PG = Me, SiR₃,
COR, CO₂R,
P(O)R₂, SO₂R, etc.

Compounds of formula I-vi-A may be prepared as illustrated below in Scheme A-6.

Scheme A-6:

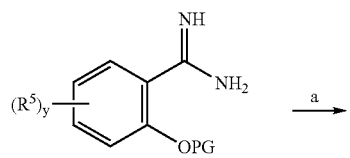

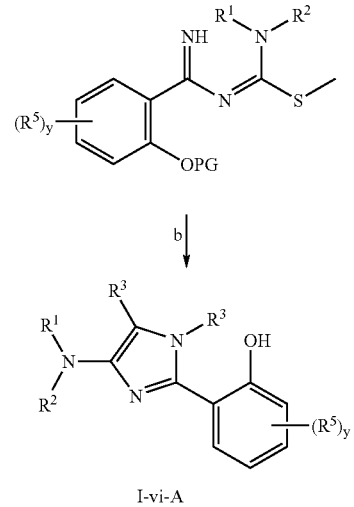

I-vi-A

PG = Me, SiR₃,
COR, CO₂R,
P(O)R₂, SO₂R, etc.

Conditions: a) p-TsOH, CH₂Cl₂; b) i. Zn(Cu), CH₂I₂, THF, heat; ii. deprotect

Compounds of formula I-vi-A may also be prepared as illustrated below in Scheme A-6-1.

Scheme A-6-1:

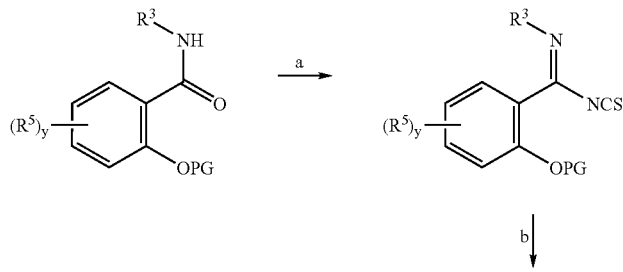

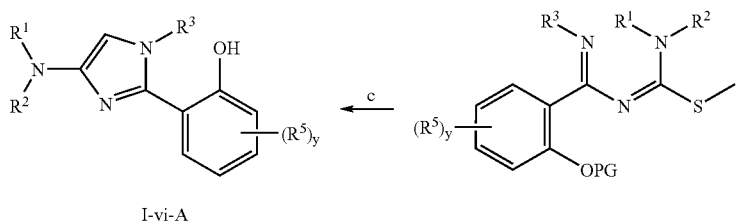

I-vi-A

PG = Me, SiR₃,
COR, CO₂R,
P(O)R₂, SO₂R, etc.

Conditions: a) i. PCl$_5$, CH$_2$Cl$_2$; ii. NaSCN, acetone; b) i. HNR$^1$R$^2$, acetone; ii. MeI; c) i. Zn(Cu), CH$_2$I$_2$, I$_2$, THF, heat; ii. Deprotect.

Compounds of formula I-vii-A may be prepared as illustrated below in Scheme A-7.

Scheme A-7:

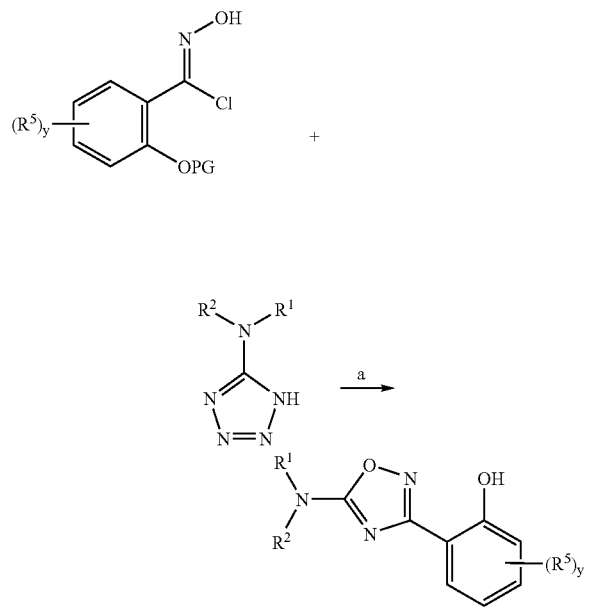

PG = Me, SiR$_3$,
COR, CO$_2$R,
P(O)R$_2$, SO$_2$R, etc.

Conditions: a) i. Et$_3$N, Dioxane-Ethanol, heat; ii. deprotect

Compounds of formula I-viii-A may be prepared as illustrated below in Scheme A-8.

Scheme A-8:

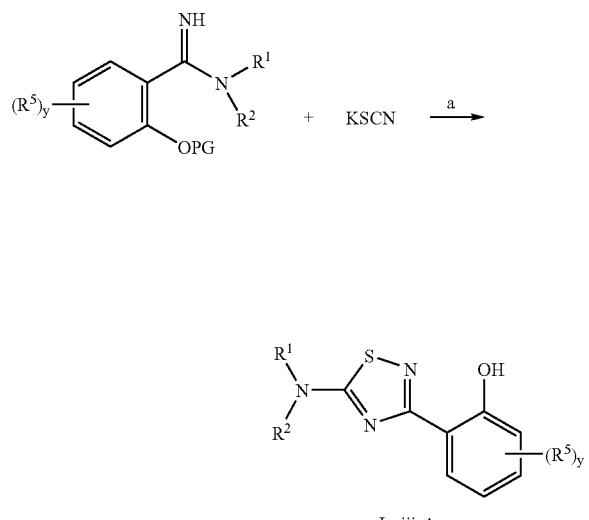

PG = Me, SiR$_3$,
COR, CO$_2$R,
P(O)R$_2$, SO$_2$R, etc.

Conditions: a) i. NaOMe, methanol, heat; ii. deprotect

Compounds of formula I-viii-A may also be prepared as illustrated below in Scheme A-8-1.

Scheme A-8-1:

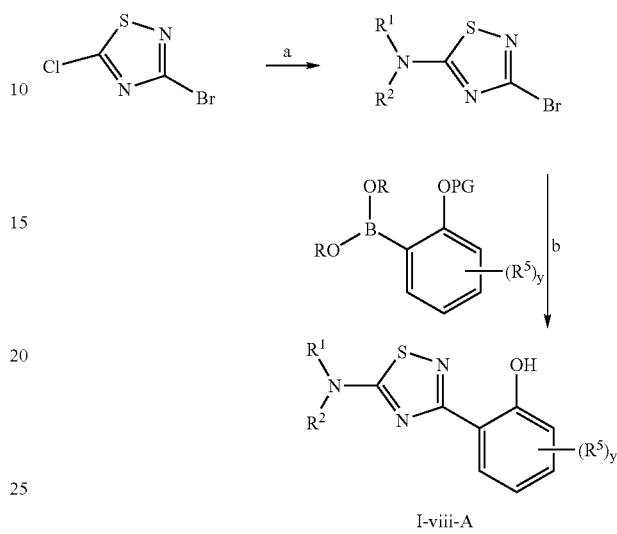

R = H, alkyl, cycloalkyl
PG = Me, SiR$_3$,
COR, CO$_2$R,
P(O)R$_2$, SO$_2$R, etc.

Conditions: a) HNR$^1$R$^2$, DMF; b) i. Pd(Ph$_3$)$_4$, K$_2$CO$_3$, CH$_3$CN, H$_2$O; ii. deprotect Compounds of formula I-ix-A may be prepared as illustrated below in Scheme A-9.

Scheme A-9:

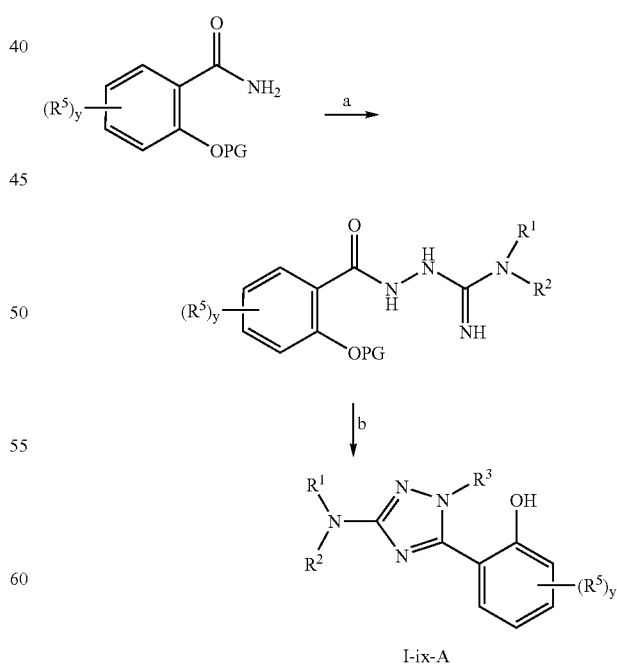

PG = Me, SiR$_3$,
COR, CO$_2$R,
P(O)R$_2$, SO$_2$R,
etc.

Conditions: a) Nitrosoguanidine, THF; b) i. 220° C.; ii. deprotect

Compounds of formula I-ix-A may also be prepared as illustrated below in Scheme A-9-1.

Scheme A-9-1:

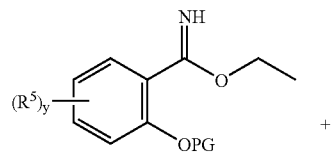

+

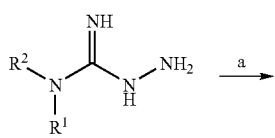

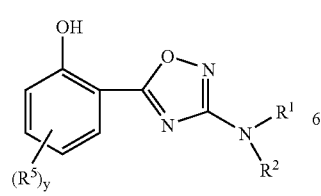

I-ix-A

PG = Me, SiR₃,
COR, CO₂R,
P(O)R₂, SO₂R, etc.

Conditions: a) i. NaOH, ethanol, H₂O, heat; ii. Deprotect.

Compounds of formula I-x-A may be prepared as illustrated below in Scheme A-10.

Scheme A-10:

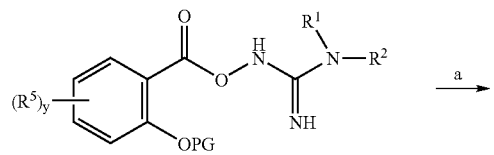

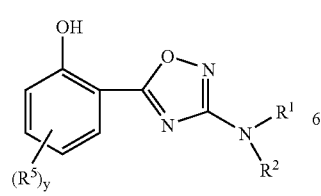

I-x-A

PG = Me, SiR₃,
COR, CO₂R,
P(O)R₂, SO₂R, etc.

Conditions: a) i. NaOH, methanol, heat; ii. deprotect

Compounds of formula I-x-A may also be prepared as illustrated below in Scheme A-10-1.

Scheme A-10-1:

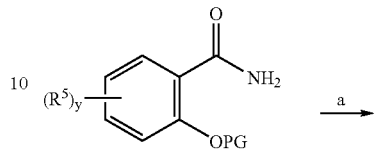

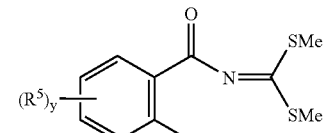

b

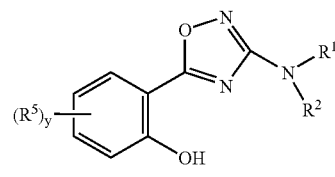

I-x-A

PG = Me, SiR₃,
COR, CO₂R,
P(O)R₂, SO₂R,
etc.

Conditions: a) NaH, THF, MeI, CS₂; b) NH₂OH, HNR¹R²

Compounds of formula I-xi-A may be prepared as illustrated below in Scheme A-11.

Scheme A-11:

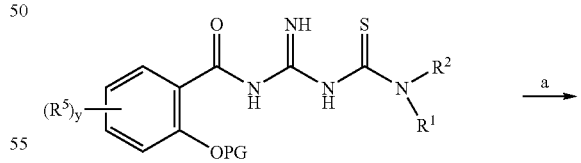

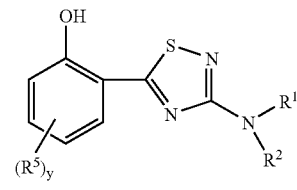

I-xi-A

PG = Me, SiR₃,
COR, CO₂R,
P(O)R₂, SO₂R, etc.

Conditions: a) i. H$_2$O$_2$, ethanol-H$_2$O, heat; ii. deprotect

Compounds of formula I-xi-A may also be prepared as illustrated below in Scheme A-11-1.

Scheme A-11-1:

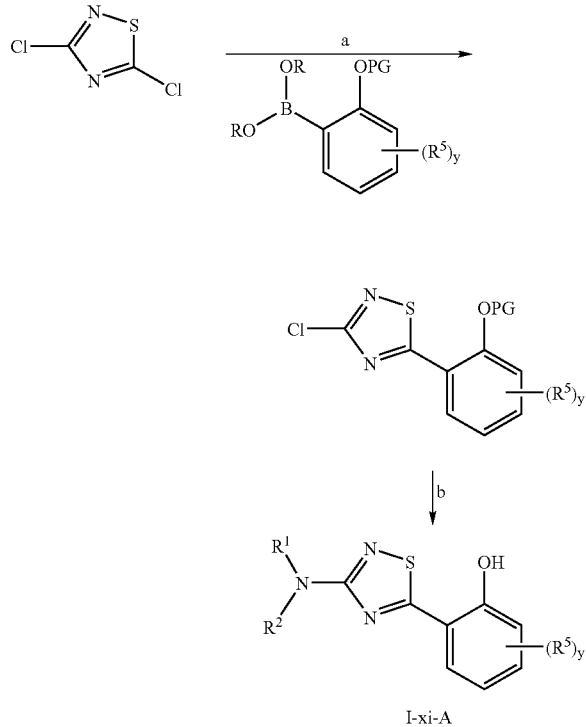

R = H, alkyl, cycloalkyl
PG = Me, SiR$_3$, COR,
CO$_2$R, P(O)R$_2$, SO$_2$R, etc.

Conditions: a) Pd(Ph$_3$)$_4$, K$_2$CO$_3$, CH$_3$CN, H$_2$O; b) i. HNR$^1$R$^2$, DMF; ii. deprotect.

Compounds of formula I-xii-A may be prepared as illustrated below in Scheme A-12.

Scheme A-12:

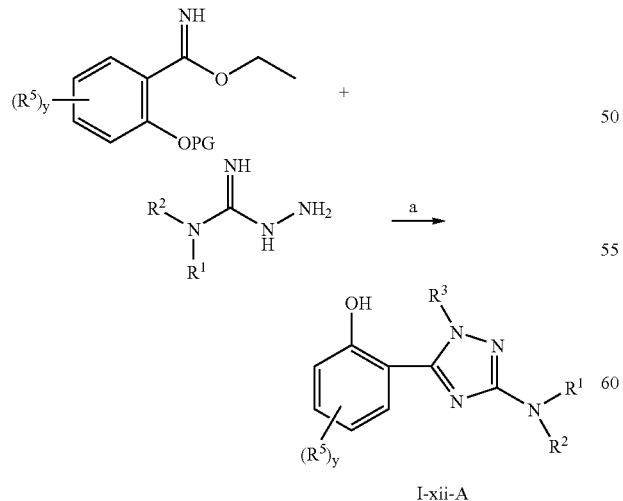

PG = Me, SiR$_3$,
COR, CO$_2$R,
P(O)R$_2$, SO$_2$R, etc.

Conditions: a) i. NaOH ethanol-H$_2$O, heat; ii. deprotect

Compounds of formula I-xii-A may also be prepared as illustrated below in Scheme A-12-1.

Scheme A-12-1:

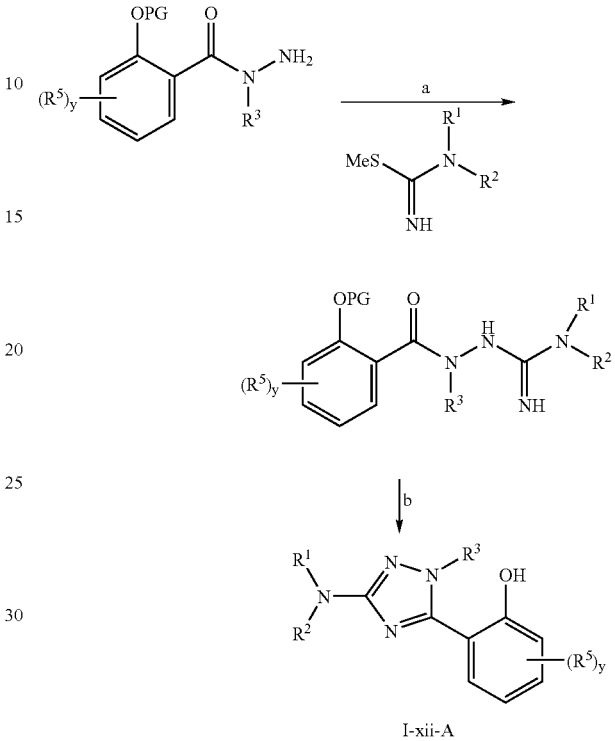

PG = Me, SiR$_3$,
COR, CO$_2$R,
P(O)R$_2$, SO$_2$R,
etc.

Conditions: a) NaOH, H$_2$O; b) i. 220° C.; ii. deprotect.

Compounds of formula I-xiii-A may be prepared as illustrated below in Scheme A-13.

Scheme A-13:

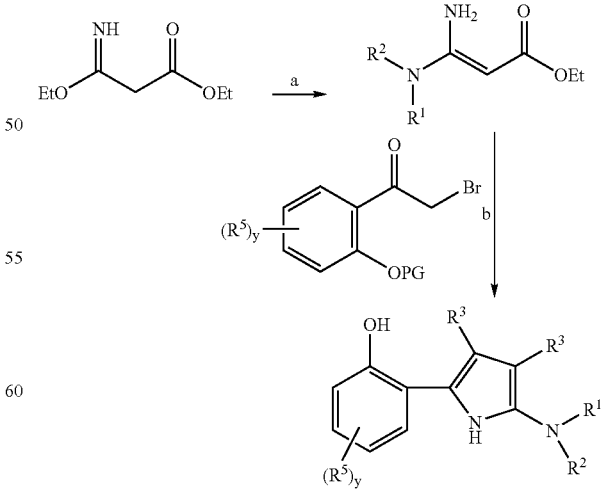

PG = Me, SiR$_3$,
COR, CO$_2$R,
P(O)R$_2$, SO$_2$R, etc.

Conditions: a) Et₃N, R¹R²NH, DMF; b) i. Ethanol, 0° C.-25° C.; ii. deprotect

Compounds of formula I-xiii-A-1 may be prepared as illustrated below in Scheme A-13-1.

Scheme A-13-1:

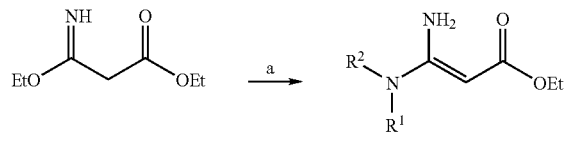

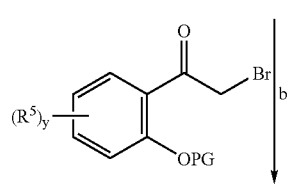

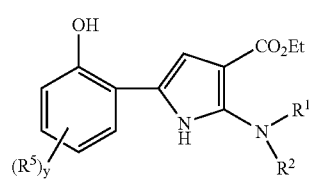

I-xiii-A-1

PG = Me, SiR₃,
COR, CO₂R,
P(O)R₂, SO₂R, etc.

Conditions: a) Et₃N, R¹R²NH, DMF; b) i. ethanol, 0° C.-25° C.; ii. deprotect

Compounds of formula I-i-B may be prepared as illustrated below in Scheme B-1.

Scheme B-1:

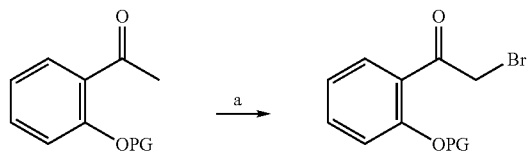

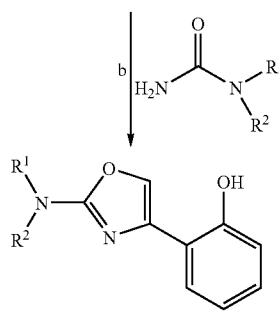

I-i-B

PG = Me, SiR₃,
COR, CO₂R,
P(O)R₂, SO₂R, etc.

Conditions: a) Br₂, MeOH; b) i. Et₃N, DMF, heat; ii. deprotect

Compounds of formula I-ii-B may be prepared as illustrated below in Scheme B-2.

Scheme B-2:

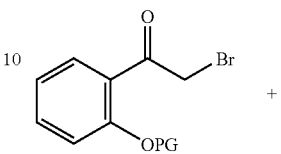

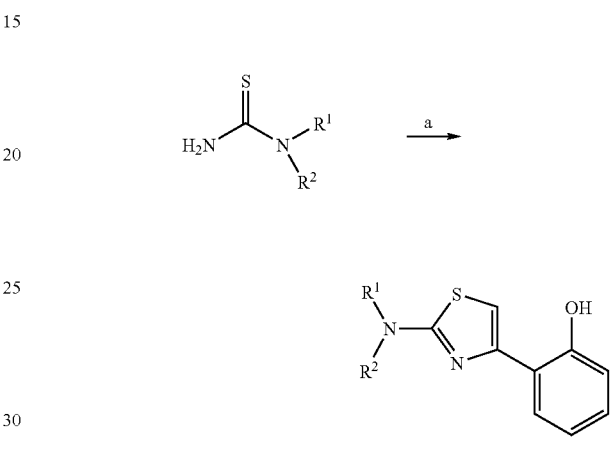

I-ii-B

PG = Me, SiR₃,
COR, CO₂R,
P(O)R₂, SO₂R, etc.

Conditions: a) i. Et₃N, THF, heat; ii. deprotect

Compounds of formula I-iii-B may be prepared as illustrated below in Scheme B-3.

Scheme B-3:

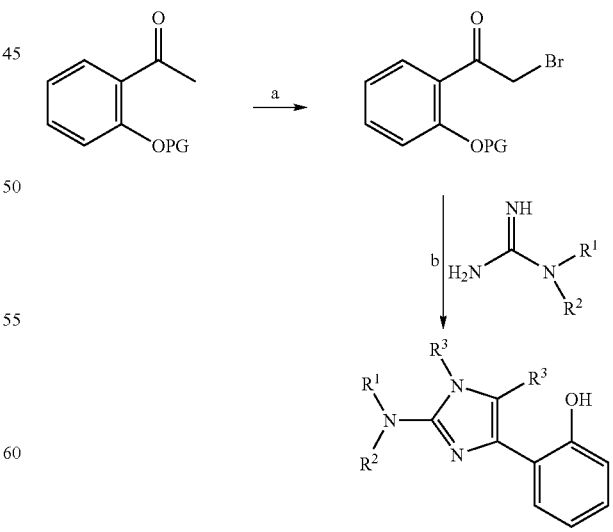

I-iii-B

PG = Me, SiR₃,
COR, CO₂R,
P(O)R₂, SO₂R, etc.

Conditions: a) Br$_2$, MeOH; b) i. Et$_3$N, DMF, heat, 10 h; ii. deprotect

Compounds of formula I-iv-B may be prepared as illustrated below in Scheme B-4.

Scheme B-4:

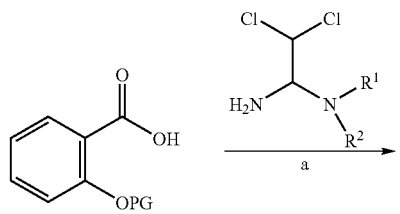

I-v-B

PG = Me, SiR$_3$,
COR, CO$_2$R,
P(O)R$_2$, SO$_2$R, etc.

Conditions: a) PdCl$_2$(dppf), Na$_2$CO$_3$, Tol, 140° C.; b) i. HNR$^1$R$^2$, DMF heat; ii. deprotect Compounds of formula I-v-B may also be prepared as illustrated below in Scheme B-5-1.

Scheme B-5-1:

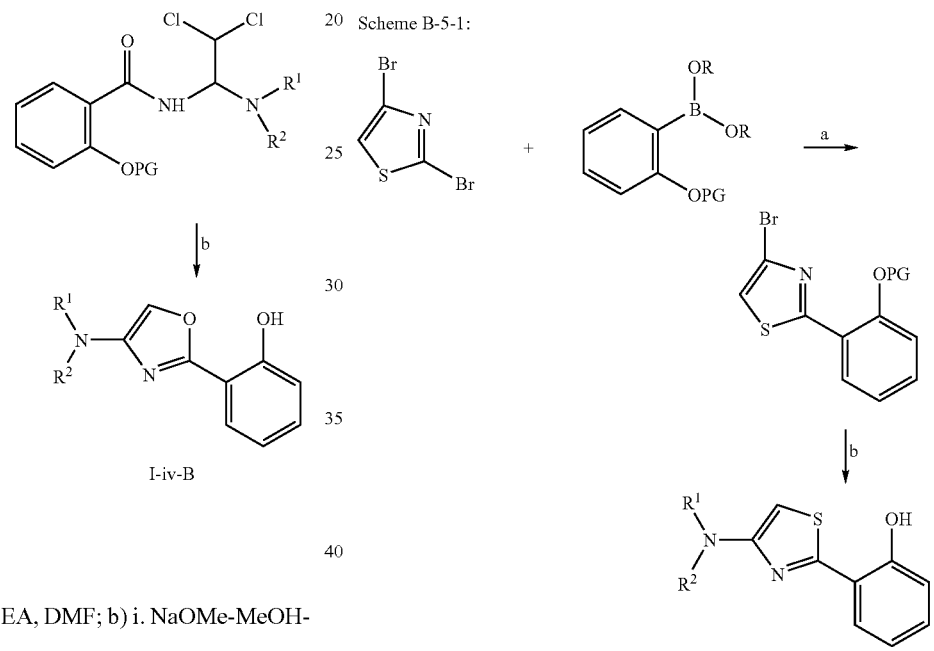

I-v-B

R = H, alkyl, cycloalkyl
PG = Me, SiR$_3$,
COR, CO$_2$R,
P(O)R$_2$, SO$_2$R, etc.

Conditions: a) PdCl$_2$(dppf), Na$_2$CO$_3$, toluene, 140° C.; b) i. HNR$^1$R$^2$, DMF heat; ii. deprotect.

Compounds of formula I-vi-B may be prepared as illustrated below in Scheme B-6.

Scheme B-6:

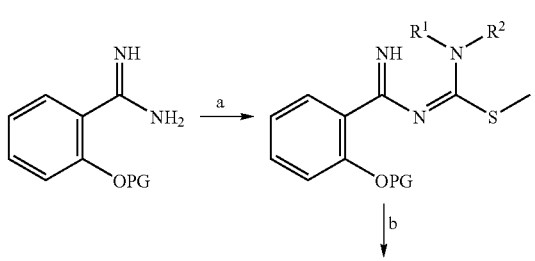

I-iv-B

PG = Me, SiR$_3$,
COR, CO$_2$R,
P(O)R$_2$, SO$_2$R, etc.

Conditions: a) HBTU, DIEA, DMF; b) i. NaOMe-MeOH-THF; ii. deprotect

Compounds of formula I-v-B may be prepared as illustrated below in Scheme B-5.

Scheme B-5:

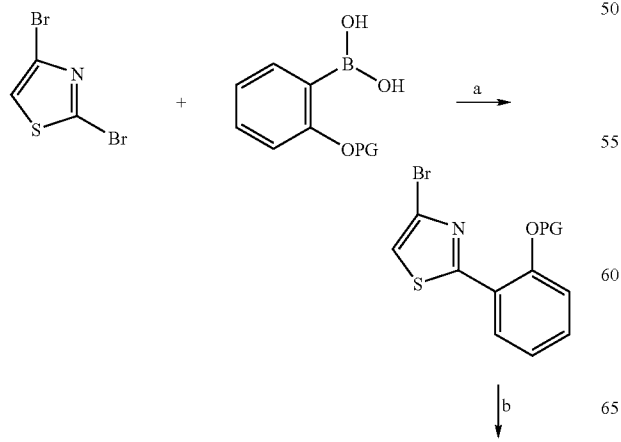

-continued

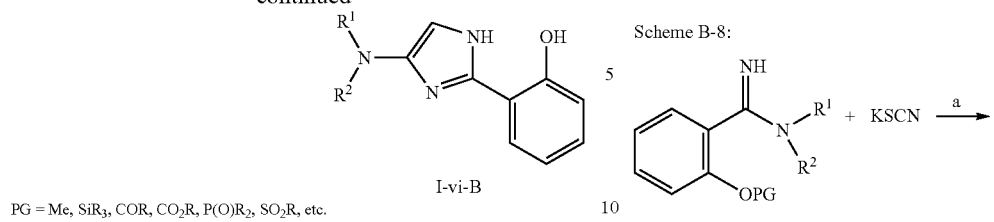

I-vi-B

PG = Me, SiR₃, COR, CO₂R, P(O)R₂, SO₂R, etc.

Conditions: a) p-TsOH, CH₂Cl₂; b) i. Zn(Cu), CH₂I₂, THF, heat; ii. deprotect

Compounds of formula I-vi-B may also be prepared as illustrated below in Scheme B-6-1.

Scheme B-6-1:

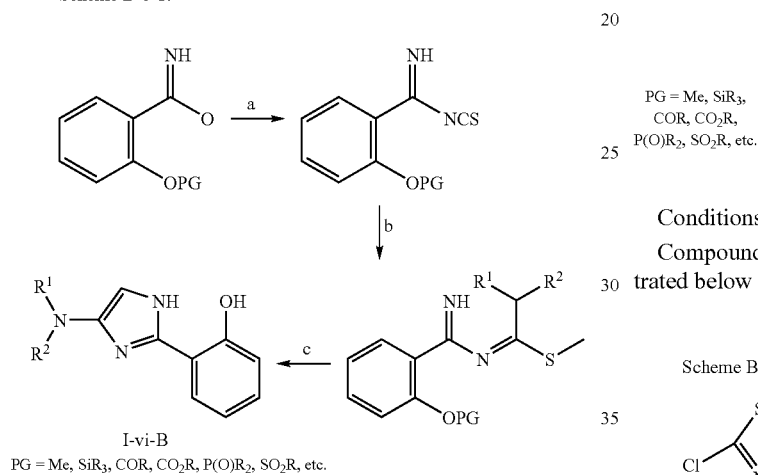

I-vi-B

PG = Me, SiR₃, COR, CO₂R, P(O)R₂, SO₂R, etc.

Conditions: a) i. PCl₅, CH₂Cl₂; ii. NaSCN, acetone; b) i. HNR¹R², acetone; ii. MeI; c) i. Zn(Cu), CH₂I₂, I₂, THF, heat; ii. deprotect.

Compounds of formula I-vii-B may be prepared as illustrated below in Scheme B-7.

Scheme B-7:

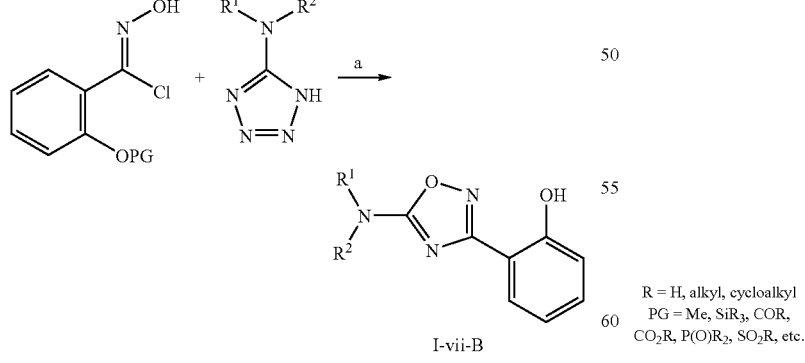

I-vii-B

PG = Me, SiR₃, COR, CO₂R, P(O)R₂, SO₂R, etc.

Conditions: a) i. Et₃N, Dioxane-Ethanol, heat; ii. deprotect

Compounds of formula I-viii-B may be prepared as illustrated below in Scheme B-8.

Scheme B-8:

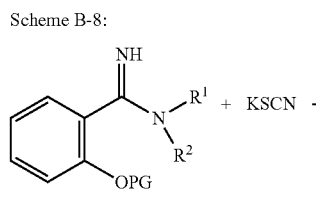

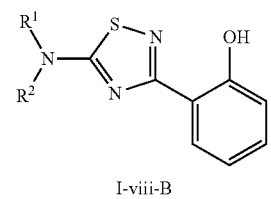

I-viii-B

PG = Me, SiR₃, COR, CO₂R, P(O)R₂, SO₂R, etc.

Conditions: a) i. NaOMe, methanol, heat; ii. deprotect

Compounds of formula I-viii-B may be prepared as illustrated below in Scheme B-8-1.

Scheme B-8-1:

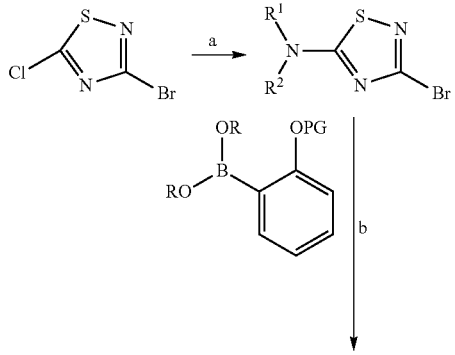

I-viii-B

R = H, alkyl, cycloalkyl
PG = Me, SiR₃, COR, CO₂R, P(O)R₂, SO₂R, etc.

Conditions: a) HNR¹R², DMF; b) i. Pd(Ph₃)₄, K₂CO₃, CH₃CN, H₂O; ii. deprotect.

Compounds of formula I-ix-B may be prepared as illustrated below in Scheme B-9.

Scheme B-9:

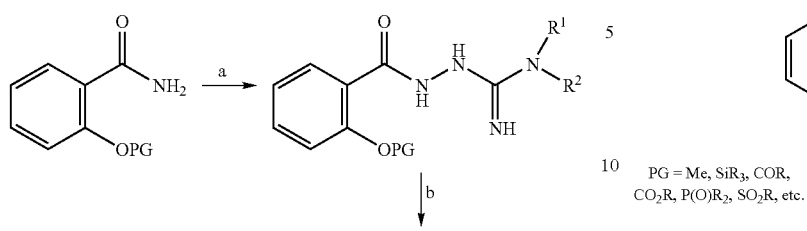

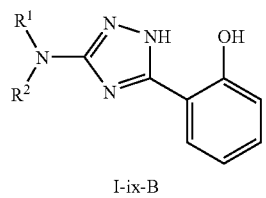

I-ix-B

PG = Me, SiR$_3$, COR, CO$_2$R, P(O)R$_2$, SO$_2$R, etc.

Conditions: a) Nitrosoguanidine, THF; b) i. 220° C.; ii. deprotect

Compounds of formula I-ix-B may also be prepared as illustrated below in Scheme B-9-1.

Scheme B-9-1:

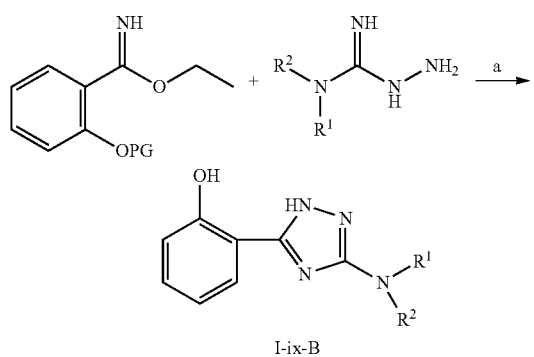

I-ix-B

PG = Me, SiR$_3$, COR, CO$_2$R, P(O)R$_2$, SO$_2$R, etc.

Conditions: a) i. NaOH, ethanol, H$_2$O, heat; ii. deprotect

Compounds of formula I-x-B may be prepared as illustrated below in Scheme B-10.

Scheme B-10:

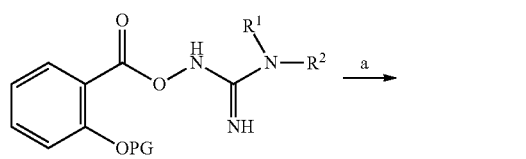

-continued

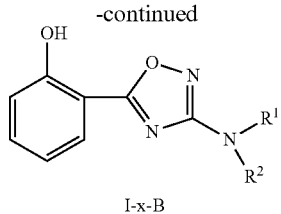

I-x-B

PG = Me, SiR$_3$, COR, CO$_2$R, P(O)R$_2$, SO$_2$R, etc.

Conditions: a) i. NaOH, methanol, heat; ii. deprotect

Compounds of formula I-x-B may also be prepared as illustrated below in Scheme B-10-1.

Scheme B-10-1:

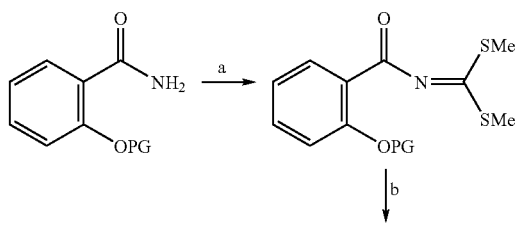

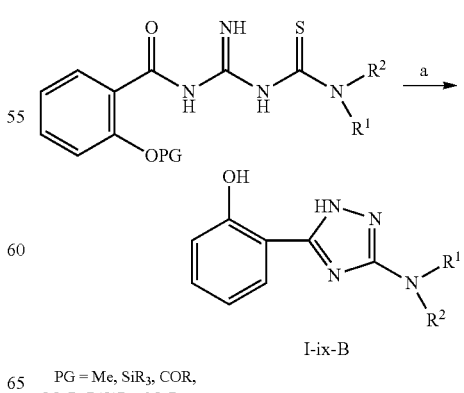

I-x-B

PG = Me, SiR$_3$, COR, CO$_2$R, P(O)R$_2$, SO$_2$R, etc.

Compounds of formula I-xi-B may be prepared as illustrated below in Scheme B-11.

Scheme B-11:

I-ix-B

PG = Me, SiR$_3$, COR, CO$_2$R, P(O)R$_2$, SO$_2$R, etc.

Conditions: a) i. H₂O₂, ethanol-H₂O, heat; ii. deprotect

Compounds of formula I-xi-B may also be prepared as illustrated below in Scheme B-11-1.

Scheme B-11-1:

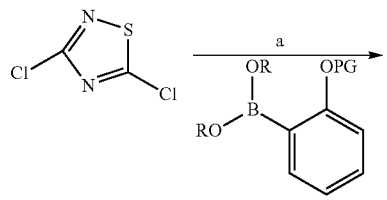

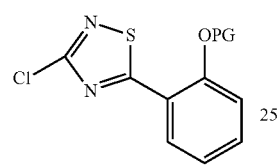

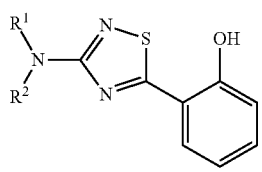

I-xi-B

R = H, alkyl, cycloalkyl
PG = Me, SiR₃, COR, CO₂R, P(O)R₂, SO₂R, etc.

Compounds of formula I-xii-B may be prepared as illustrated below in Scheme B-12.

Scheme B-12:

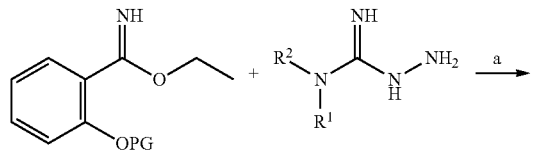

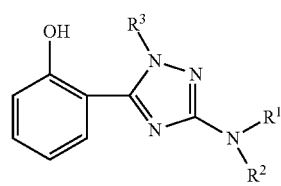

I-xii-B

PG = Me, SiR₃, COR,
CO₂R, P(O)R₂, SO₂R, etc.

Conditions: a) i. NaOH, ethanol-H₂O, heat; ii. deprotect

Compounds of formula I-xii-B may be prepared as illustrated below in Scheme B-12-1.

Scheme B-12-1:

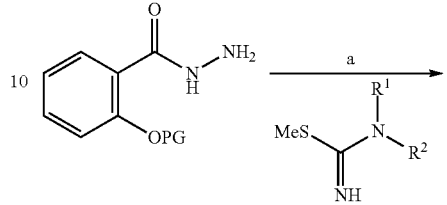

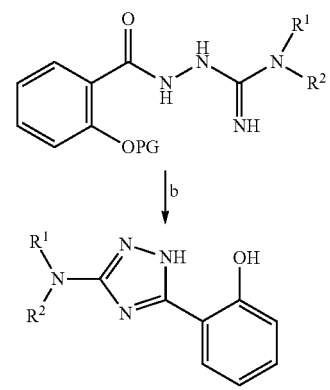

I-xii-B

PG = Me, SiR₃, COR, CO₂R, P(O)R₂, SO₂R, etc.

Compounds of formula I-xiii-B may be prepared as illustrated below in Scheme B-13.

Scheme B-13:

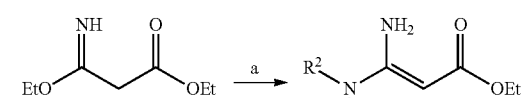

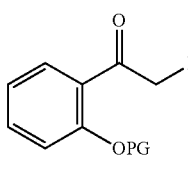

I-xiii-B

PG = Me, SiR₃,
COR, CO₂R,
P(O)R₂, SO₂R, etc.

Conditions: a) Et$_3$N, R$^1$R$^2$NH, DMF; b) i. Ethanol, 0° C.-25° C.; ii. deprotect Compounds of formula I-xiii-B-1 may be prepared as illustrated below in Scheme B-13-1.

Scheme B-13-1:

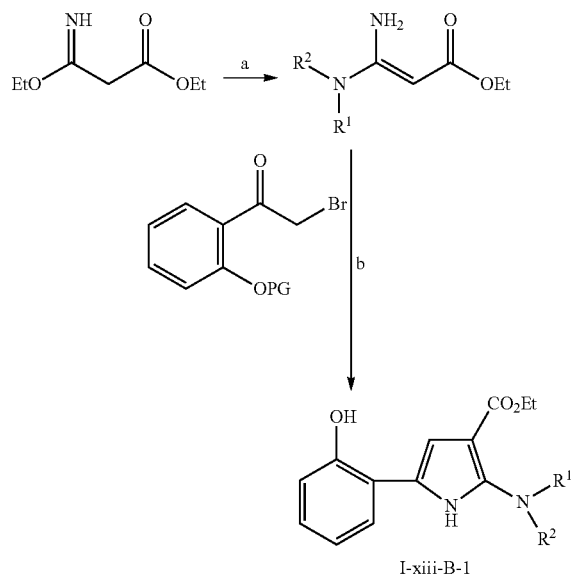

PG = Me, SiR$_3$,
COR, CO$_2$R,
P(O)R$_2$, SO$_2$R, etc.

5. Uses, Formulation and Administration

Pharmaceutically Acceptable Compositions

As discussed above, the present invention provides compounds that are inhibitors of voltage-gated sodium ion channels and/or calcium channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel or calcium channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitus or cancer pain is provided comprising administering an effective amount of a compound or a pharmaceutically acceptable composition to a subject in need thereof.

In certain embodiments of the present invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitus or cancer pain.

The compounds and compositions, according to the method of the present invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitus or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels or calcium channels, preferably N-type calcium channels. In one embodiment, the compounds and compositions of the invention are inhibitors of one or more of NaV1.1, NaV1.2, NaV1.3, NaV1.4, NaV1.5, NaV1.6, NaV1.7, NaV1.8, NaV1.9, or CaV2.2, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease, condition, or disorder. When activation or hyperactivity of NaV1.1, NaV1.2, NaV1.3, NaV1.4, NaV1.5, NaV1.6, NaV1.7, NaV1.8, NaV1.9, or CaV2.2, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder" or a "CaV2.2-mediated condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, NaV1.9, or CaV2.2 may be assayed according to methods described generally in the Examples herein, or according to methods available to one of ordinary skill in the art.

In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2. In yet other embodiments, compounds of the invention are useful as dual inhibitors of NaV1.8 and a TTX-sensitive ion channel such as NaV1.3 or NaV1.7.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, NaV1.9, or CaV2.2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, NaV1.9, or CaV2.2 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

In order that the invention described herein may be more fully understood, the following examples are set forth. It should be understood that these examples are for illustrative purposes only and are not to be construed as limiting this invention in any manner.

EXAMPLE

Benzyl 4-(4-(2-fluorophenyl)thiazol-2-yl)piperazine-1-carboxylate (9)

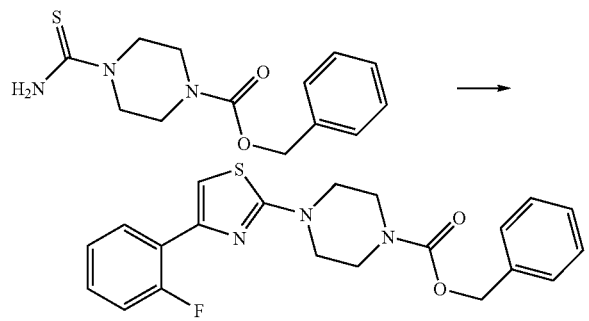

A solution of benzyl 4-thiocarbamoylpiperazine-1-carboxylate (2.7 g, 9.7 mmol), 2-bromo-1-(2-fluorophenyl)ethanone (2.1 g, 9.7 mmol), diisopropyl ethylamine (1.9 mL, 11 mmol), and THF (32 mL) was sealed in a microwave vessel and heated by microwave irradiation at 120° C. for 20 seconds. The reaction was cooled to room temperature, diluted with water, and extracted with $CH_2Cl_2$. The combined extracts were washed with water, dried over $Na_2SO_4$, and concentrated under reduced pressure. The residue was purified by flash chromatography ($SiO_2$, 0%-30% EtOAc/hexanes) to give benzyl 4-(4-(2-fluorophenyl)thiazol-2-yl)piperazine-1-carboxylate (1.05 g, 27% yield). LC/MS: m/z 398.3 (M+H)$^+$ at 3.84 min (10%-99% $CH_3CN$ (0.035% TFA)/$H_2O$ (0.05% TFA)).

1-(4-(2-Fluorophenyl)thiazol-2-yl)piperazine

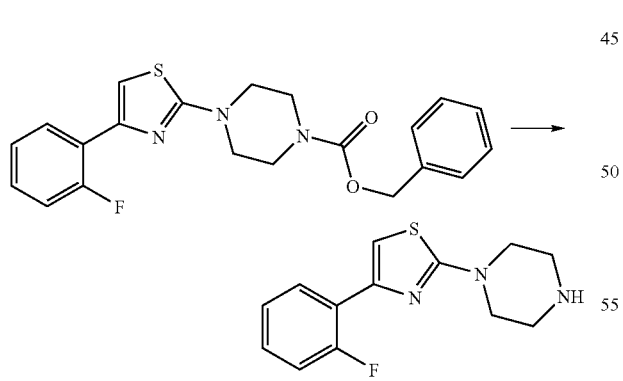

To a solution of benzyl 4-(4-(2-fluorophenyl)thiazol-2-yl)piperazine-1-carboxylate (0.85 g, 2.1 mmol) in $CH_2Cl_2$ (2 µL) cooled to −50° C. was added boron tribromide (1 M in $CH_2Cl_2$, 8.6 mL, 8.6 mmol). The reaction was stirred at −50° C. for 20 min and then carefully quenched with saturated aqueous $NaHCO_3$. The mixture was extracted with $CH_2Cl_2$, and the combined extracts were washed with water, dried over $Na_2SO_4$, and concentrated under reduced pressure to yield 1-(4-(2-fluorophenyl)thiazol-2-yl)piperazine. LC/MS: m/z 264.1 (M+H)$^+$ at 2.04 min (10%-99% $CH_3CN$ (0.035% TFA)/$H_2O$ (0.05% TFA)).

Isobutyl 4-(4-(2-fluorophenyl)thiazol-2-yl)piperazine-1-carboxylate (10)

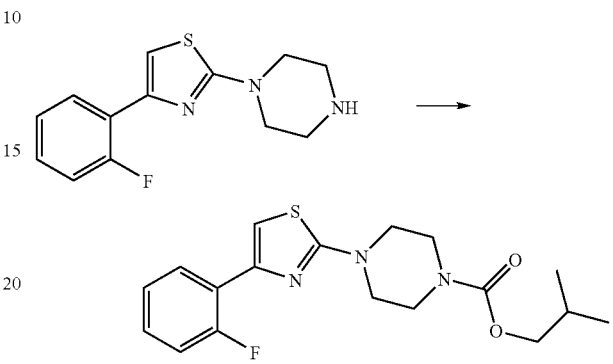

A solution of 1-(4-(2-fluorophenyl)thiazol-2-yl)piperazine (0.13 g, 0.50 mmol), triethylamine (0.10 mL, 0.75 mmol), and $CH_2Cl_2$ (1.7 mL) was cooled in an ice bath, and isobutyl chloroformate (0.10 mL, 0.75 mmol) was added. The reaction was stirred at 0° C. for 20 min, diluted with $CH_2Cl_2$, washed with water, dried over $Na_2SO_4$, and concentrated under reduced pressure. The residue was purified by reverse phase HPLC (10%-99% $CH_3CN$ (0.035% TFA)/$H_2O$ (0.05% TFA)) to yield isobutyl 4-(4-(2-fluorophenyl)thiazol-2-yl)piperazine-1-carboxylate. LC/MS: m/z 364.1 (M+H)$^+$ at 3.87 min (10%-99% $CH_3CN$ (0.035% TFA)/$H_2O$ (0.05% TFA)).

Isobutyl 1-(3-bromo-1,2,4-thiadiazol-5-yl)piperidin-4-ylcarbamate

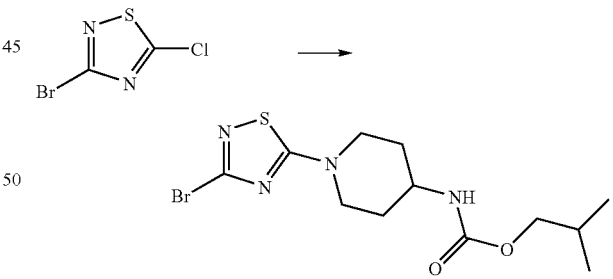

A mixture of 3-bromo-5-chloro-1,2,4-thiadiazole (0.21 g, 1.1 mmol), isobutyl piperidin-4-ylcarbamate (0.23 g, 1.2 mmol), and DMF (2 mL) was sealed in a microwave vessel and heated by microwave irradiation at 100° C. for two minutes. The reaction was cooled to room temperature, diluted with water, and extracted with $CH_2Cl_2$. The combined extracts were washed with water, dried over $Na_2SO_4$, and concentrated under reduced pressure to yield isobutyl 1-(3-bromo-1,2,4-thiadiazol-5-yl)piperidin-4-ylcarbamate. LC/MS: m/z 365.0 (M+H)$^+$ at 3.20 min (10%-99% $CH_3CN$ (0.035% TFA)/$H_2O$ (0.05% TFA)).

Isobutyl 1-(3-(2-hydroxyphenyl)-1,2,4-thiadiazol-5-yl)piperidin-4-ylcarbamate (20)

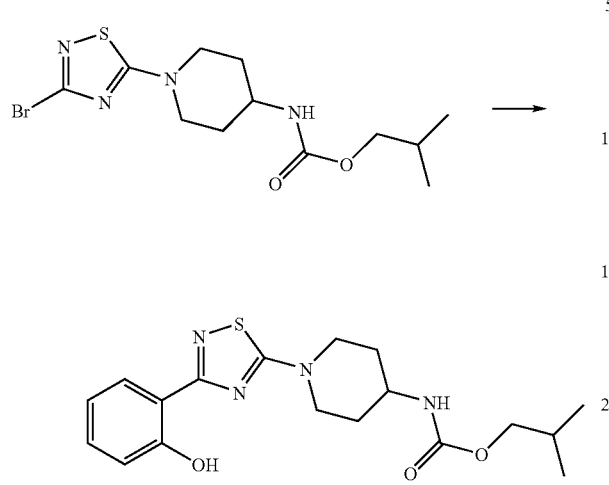

A mixture of isobutyl 1-(3-bromo-1,2,4-thiadiazol-5-yl)piperidin-4-ylcarbamate (0.38 g, 1.1 mmol), 2-(4,4,5,5-tetramethyl-1,3,2-dioxaborolan-2-yl)-phenol (0.35 g, 1.6 mmol), Pd(Ph$_3$)$_4$ (12 mg, 11 μmol), K$_2$CO$_3$ (0.29 g, 2.1 mmol), CH$_3$CN (3.0 mL), and H$_2$O (0.3 mL) was sealed in a microwave vessel and heated by microwave irradiation at 175° C. for 15 minutes. The reaction was cooled to room temperature, diluted with water, and extracted with CH$_2$Cl$_2$. The combined extracts were washed with water, dried over Na$_2$SO$_4$, and concentrated under reduced pressure. The residue was purified by reverse phase HPLC (10%-99% CH$_3$CN (0.035% TFA)/H$_2$O (0.05% TFA)) to yield isobutyl 1-(3-(2-hydroxyphenyl)-1,2,4-thiadiazol-5-yl)piperidin-4-ylcarbamate. LC/MS: m/z 377.3 (M+H)$^+$ at 3.77 min (10%-99% CH$_3$CN (0.035% TFA)/H$_2$O (0.05% TFA)).

3-Chloro-5-(2-methoxyphenyl)-1,2,4-thiadiazole

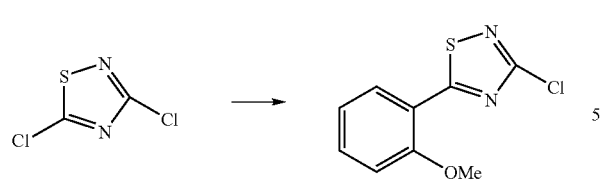

A mixture of 3,5-dichloro-1,2,4-thiadiazole (0.14 g, 0.93 mmol), 2-methoxyphenylboronic acid (0.16 g, 1.0 mmol), Pd(PPh$_3$)$_4$ (11 mg, 9.3 mmol), K$_2$CO$_3$ (0.26 g, 1.9 mmol), and CH$_3$CN (3 mL containing 10% H$_2$O) was sealed in a microwave vessel and heated by microwave irradiation at 100° C. for three minutes. The reaction was cooled to room temperature, diluted with water, and extracted with CH$_2$Cl$_2$. The combined extracts were washed with water, dried over Na$_2$SO$_4$, and concentrated under reduced pressure to yield 3-chloro-5-(2-methoxyphenyl)-1,2,4-thiadiazole. LC/MS: m/z 227 (M+H)$^+$ at 3.45 min (10%-99% CH$_3$CN (0.035% TFA)/H$_2$O (0.05% TFA)).

1-(5-(2-Methoxyphenyl)-1,2,4-thiadiazol-3-yl)piperazine

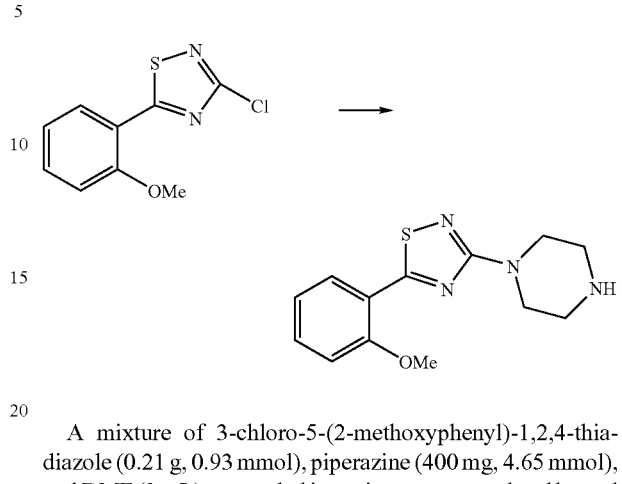

A mixture of 3-chloro-5-(2-methoxyphenyl)-1,2,4-thiadiazole (0.21 g, 0.93 mmol), piperazine (400 mg, 4.65 mmol), and DMF (3 mL) was sealed in a microwave vessel and heated by microwave irradiation at 150° C. for 5 minutes. The reaction was cooled to room temperature, diluted with water, and extracted with CH$_2$Cl$_2$. The combined extracts were washed with water, dried over Na$_2$SO$_4$, and concentrated under reduced pressure to yield 1-(5-(2-methoxyphenyl)-1,2,4-thiadiazol-3-yl)piperazine. LC/MS: m/z 277.1 (M+H)$^+$ at 2.19 min (10%-99% CH$_3$CN (0.035% TFA)/H$_2$O (0.05% TFA)).

Isobutyl 4-(5-(2-methoxyphenyl)-1,2,4-thiadiazol-3-yl)piperazine-1-carboxylate

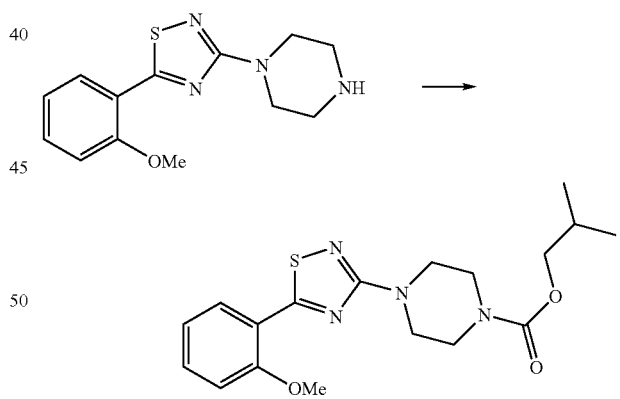

To a mixture of 1-(5-(2-methoxyphenyl)-1,2,4-thiadiazol-3-yl)piperazine (80 mg, 0.29 mmol) and triethylamine (61 μL, 0.43 mmol) in CH$_2$Cl$_2$ (0.5 mL) at 0° C. was added isobutyl chloroformate (59 mg, 0.43 mmol) in CH$_2$Cl$_2$ (0.5 mL). The reaction mixture was stirred at 0° C. for 1 h, diluted with water, and extracted with CH$_2$Cl$_2$. The combined extracts were washed with water, dried over Na$_2$SO$_4$, and concentrated under reduced pressure to yield isobutyl 4-(5-(2-methoxyphenyl)-1,2,4-thiadiazol-3-yl)piperazine-1-carboxylate. LC/MS: m/z 377.5 (M+H)$^+$ at 3.81 min (10%-99% CH$_3$CN (0.035% TFA)/H$_2$O (0.05% TFA)).

Isobutyl 4-(5-(2-hydroxyphenyl)-1,2,4-thiadiazol-3-yl)piperazine-1-carboxylate (21)

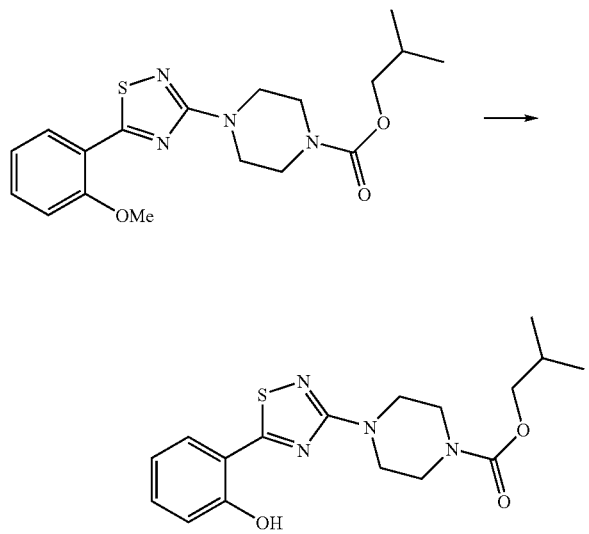

To isobutyl 4-(5-(2-methoxyphenyl)-1,2,4-thiadiazol-3-yl)piperazine-1-carboxylate from above was added boron tribromide solution (1 M in $CH_2Cl_2$, 1.7 mL, 1.7 mmol) at −30° C. The reaction mixture was stirred at −30° C. for 1 h and at room temperature for 3 h. To this mixture was added boron tribromide (1 M in $CH_2Cl_2$, 1.4 mL, 1.4 mmol), and the reaction was stirred for another hour. The reaction mixture was diluted with saturated $NaHCO_3$ and extracted with $CH_2Cl_2$. The combined extracts were washed with water, dried over $Na_2SO_4$, and concentrated under reduced pressure to give a residue which was filtered and purified by reverse phase HPLC (10%-99% $CH_3CN$ (0.035% TFA)/$H_2O$ (0.05% TFA)) to yield isobutyl 4-(5-(2-hydroxyphenyl)-1,2,4-thiadiazol-3-yl)piperazine-1-carboxylate. LC/MS: m/z 363.3 $(M+H)^+$ at 3.52 min (10%-99% $CH_3CN$ (0.035% TFA)/$H_2O$ (0.05% TFA)).

Representative analytical data is shown below in Table 2 for the compounds of the present invention.

TABLE 2

| Cmpd. No. | LC-MS M + 1 | LC-RT min |
|---|---|---|
| 1 | 260.8 | 3.54 |
| 2 | 362.2 | 3.85 |
| 3 | 376.3 | 3.29 |
| 4 | 382.2 | 3.65 |
| 5 | 360.2 | 2.98 |
| 6 | 348.3 | 3.66 |
| 7 | 376.5 | 3.22 |
| 8 | 364.3 | 3.23 |
| 9 | 398.3 | 3.84 |
| 10 | 364.1 | 3.87 |
| 11 | 378.2 | 4.19 |
| 12 | 378.2 | 3.34 |
| 13 | 366.0 | 3.36 |
| 14 | 362.3 | 2.89 |
| 15 | 391.1 | 3.23 |
| 16 | 377.3 | 3.77 |
| 17 | 363.3 | 3.52 |

Assays for Detecting and Measuring NaV Inhibition Properties of Compound

Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (ee Gonzalez, J. E. and R.Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

B) VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 µL of Bath Solution #2 (BS#2).

2) A 15 uM CC2-DMPE solution is prepared by mixing 5 mM coumarin stock solution with 10% Pluronic 127 1:1 and then dissolving the mix in the appropriate volume of BS#2.

3) After bath solution is removed from the 96-well plates, the cells are loaded with 80 µL of the CC2-DMPE solution. Plates are incubated in the dark for 30 minutes at room temperature.

4) While the cells are being stained with coumarin, a 15 µL oxonol solution in BS#2 is prepared. In addition to $DiSBAC_2$ (3), this solution should contain 0.75 mM ABSC1 and 30 µL veratridine (prepared from 10 mM EtOH stock, Sigma #V-5754).

5) After 30 minutes, CC2-DMPE is removed and the cells are washed twice with 225 µL of BS#2. As before, the residual volume should be 40 µL.

6) Upon removing the bath, the cells are loaded with 80 µL of the $DiSBAC_2(3)$ solution, after which test compound, dissolved in DMSO, is added to achieve the desired test concentration to each well from the drug addition plate and mixed thoroughly. The volume in the well should be roughly 121 µL. The cells are then incubated for 20-30 minutes.

7) Once the incubation is complete, the cells are ready to be assayed on VIPR® with a sodium addback protocol. 120 µL of Bath solution #1 is added to stimulate the NaV dependent depolarization. 200 µL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460nm} - background_{460nm})}{(intensity_{580nm} - background_{580nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound Solutions [mM]

Bath Solution #1: NaCl 160, KCl 4.5, CaCl$_2$ 2, MgCl$_2$ 1, HEPES 10, pH 7.4 with NaOH Bath Solution #2 TMA-Cl 160, CaCl$_2$ 0.1, MgCl$_2$ 1, HEPES 10, pH 7.4 with KOH (final K concentration ~5 mM)

CC2-DMPE: prepared as a 5 mM stock solution in DMSO and stored at −20° C.

DiSBAC$_2$(3): prepared as a 12 mM stock in DMSO and stored at −20° C.

ABSC1: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

C) VIPR® Optical Membrane Potential Assay Method with Electrical Stimulation

The following is an example of how NaV1.3 inhibition activity is measured using the optical membrane potential method#2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:

100 mg/mL Pluronic F-127 (Sigma #P2443), in dry DMSO 10 mM DiSBAC$_2$(3) (Aurora #00-100-010) in dry DMSO 10 mM CC2-DMPE (Aurora #00-100-008) in dry DMSO 200 mM ABSC1 in H$_2$0

Hank's Balanced Salt Solution (Hyclone #SH30268.02) supplemented with 10 mM HEPES (Gibco #15630-080)

Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is to wells containing washed cells, resulting in a 10 µM final staining concentration. The cells are stained for 30 minutes in the dark at RT.

2×DiSBAC$_2$(3) with ABSC1=6 µM DiSBAC$_2$(3) and 1 mM ABSC1: The required amount of 10 mM DiSBAC$_2$(3) is added to a 50 ml conical tube and mixed with 1 µL 10% pluronic for each mL of solution to be made and vortexed together. Then HBSS/HEPES is added to make up 2× solution. Finally, the ABSC1 is added.

The 2× DiSBAC$_2$(3) solution can be used to solvate compound plates. Note that compound plates are made at 2× drug concentration. Wash stained plate again, leaving residual volume of 50 µL. Add 50 uL/well of the 2× DiSBAC$_2$(3) w/ ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay buffer #1

140 mM NaCl, 4.5 mM KCl, 2 mM CaCl$_2$, 1 mM MgCl$_2$, 10 mM HEPES, 10 mM glucose, pH 7.40, 330 mOsm Pluronic stock (1000×): 100 mg/mL pluronic 127 in dry DMSO Oxonol stock (3333×): 10 mM DiSBAC$_2$(3) in dry DMSO Coumarin stock (1000×): 10 mM CC2-DMPE in dry DMSO ABSC1 stock (400×): 200 mM ABSC1 in water Assay Protocol 1. Insert or use electrodes into each well to be assayed.

2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460nm} - background_{460nm})}{(intensity_{580nm} - background_{580nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 µm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

VOLTAGE-CLAMP Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording.

Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), KH2PO4 (0.44), MgCl2 (0.5), MgSO4 (0.41), NaHCO3 (4), Na2HPO4 (0.3), glucose (5.6), HEPES (10), CdCl2 (0.4), NiCl2 (0.1), TTX ($0.25 \times 10^{-3}$).

CURRENT-CLAMP Assay for NaV Channel Inhibition Activity of Compounds

Cells were current-clamped in whole-cell configuration with a Multiplamp 700A amplifier (Axon Inst). Borosilicate pipettes (4-5 MOhm) were filled with (in mM): 150 K-gluconate, 10 NaCl, 0.1 EGTA, 10 Hepes, 2 $MgCl_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

The activity of selected compounds of the present invention against NaV 1.8 channel is shown below in Table 3. In Table 3, the symbols have the following meanings: "+++" means <10 µM; "++" means between 10 µM and 20 µM; and "+" means >20 µM.

TABLE 3

| Compound # | IC$_{50}$ |
|---|---|
| 1 | ++ |
| 2 | + |
| 3 | ++ |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |

What is claimed is:

1. A compound of formula I:

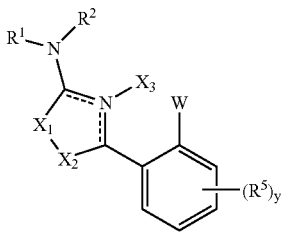

I or a pharmaceutically acceptable salt thereof,
wherein:
$\phantom{=}=$ is a single or double bond;
$X_1$ is —S—;
$X_2$ is =CR$^3$—;
$X_3$ is a lone pair of electrons;
provided that $X_1$, $X_2$, and $N(X_3)$, taken together with the intervening carbon atoms form a 5-membered heteroaryl ring;
W is halogen or OR';
$R^1$ and $R^2$, taken together with the nitrogen atom, form a piperidinyl ring (cc) or a piperazinyl ring (dd):

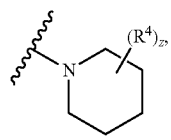

cc

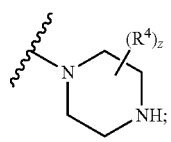

dd wherein z is 0-5;
y is 0;
$R^3$ is hydrogen;
$R^4$ is Q-$R^X$; wherein Q is a bond or is a $C_1$-$C_6$ alkylidene chain and $R^X$ is selected from —NR'COR', —NR'CO$_2$R', —COR', —CO$_2$R', or —SO$_2$R';
$R^5$ is halogen; and
each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur.

2. A compound according to claim 1, wherein $R^1$ and $R^2$ taken together form a piperazinyl ring:

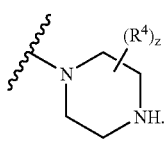

dd

3. The compound according to claim 1, wherein $R^1$ and $R^2$ together form a ring as shown below:

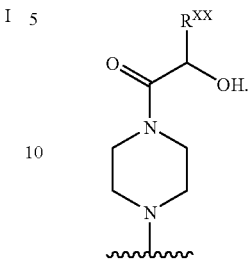

wherein $R^{xx}$ is C1-C6 alkyl.

4. The compound according to claim 3, wherein $R^{xx}$ is methyl, n-propyl, isopropyl, n-butyl, isobutyl, or t-butyl.

5. The compound according to claim 1, wherein $R^1$ and $R^2$ taken together form ring (kk) as shown below:

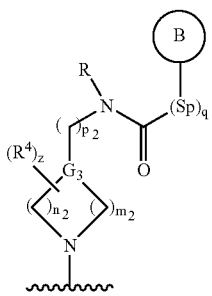

kk $G_3$ is —N—, or CH;
each of $m_2$ and $n_2$ is 2;
$p_2$ is 0-2; provided that when $G_3$ is N, then $p_2$ is not 0;
q is 0 or 1;
z is 0-4;
Sp is a bond or a C1-C6 alkylidene linker;
ring B is a 4-8 membered, saturated, partially unsaturated, or aromatic, monocyclic heterocyclic ring having 1-3 heteroatoms selected from O, S, or N, wherein ring B is optionally substituted with w independent occurrences of —$R^{12}$, wherein $w_2$ is 0-4;
each occurrence of $R^{12}$ is independently Q-$R^X$; wherein Q is a bond or is a $C_1$-$C_6$ alkylidene chain; and each occurrence of $R^X$ is independently selected from —NR'COR', —NR'CO$_2$R', —COR', —CO$_2$R' or —SO$_2$R'; and
each occurrence of R is independently hydrogen or $C_{1-6}$ aliphatic group having up to three substituents; and each occurrence of R' is independently hydrogen or $C_{1-6}$ aliphatic group, a 3-8-membered saturated, partially unsaturated, or fully unsaturated monocyclic ring having 0-3 heteroatoms independently selected from nitrogen, oxygen, or sulfur, wherein R' has up to four substituents.

6. The compound according to claim 1, wherein $R^1$ and $R^2$ taken together form a ring (ll):

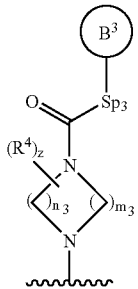

wherein:
each of $m_3$ and $n_3$ is 2;
z is 0-4;
$Sp^3$ is —O—, or a C1-C6 alkylidene linker,
ring $B_3$ is a 4-8 membered, saturated, partially unsaturated, or aromatic, monocyclic heterocyclic ring having 1-3 heteroatoms selected from O, S, or N, wherein ring $B_3$ is optionally substituted with w independent occurrences of —$R^{13}$, wherein $w_3$ is 0-4;
each occurrence of $R^{13}$ is independently Q-$R^X$; wherein Q is a bond or is a $C_1$-$C_6$ alkylidene chain; and each occurrence of $R^X$ is independently selected from NR'COR', —NR'CO$_2$R', —COR', —CO$_2$R'; and
each occurrence of R is independently hydrogen or $C_{1-6}$ aliphatic group having up to three substituents; and each occurrence of R' is independently hydrogen or $C_{1-6}$ aliphatic group, a 3-8-membered saturated, partially unsaturated, or fully unsaturated monocyclic ring having 0-3 heteroatoms independently selected from nitrogen, oxygen, or sulfur, wherein R' has up to four substituents.

7. The compound according to claim 1, wherein $R^1$ and $R^2$ taken together form a ring (mm):

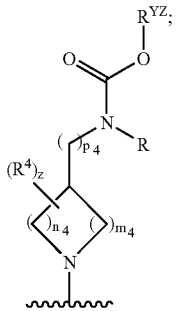

wherein:
each of $m_4$ and $n_4$ is 2;
$p_4$ is 1-2;
$R^{YZ}$ is $C_1$-$C_6$ aliphatic group, optionally substituted with $w_4$ independent occurrences of —$R^{14}$, wherein $w_4$ is 0-3;
each occurrence of $R^{14}$ is independently Q-$R^X$; wherein Q is a bond or is a $C_1$-$C_6$ alkylidene chain; and each occurrence of $R^X$ is independently selected from NR'COR', —NR'CO$_2$R', —COR', —CO$_2$R', or —SO$_2$R'; and each occurrence of R is independently hydrogen or $C_{1-6}$ aliphatic group having up to three substituents; and each occurrence of R' is independently hydrogen or $C_{1-6}$ aliphatic group, a 3-8-membered saturated, partially unsaturated, or fully unsaturated monocyclic ring having 0-3 heteroatoms independently selected from nitrogen, oxygen, or sulfur, wherein R' has up to four substituents.

8. The compound according to claim 1, wherein W is OR'.
9. The compound according to claim 8, wherein W is OH.
10. A pharmaceutical composition comprising a compound according to claim 1 and a pharmaceutically acceptable adjuvant or carrier.
11. A compound according to claim 1, wherein said compound is selected from the group consisting of the following compounds:

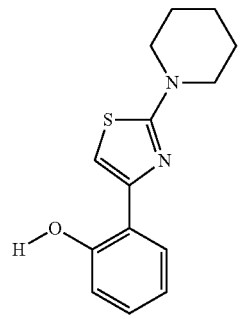

1

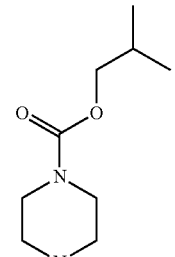

2

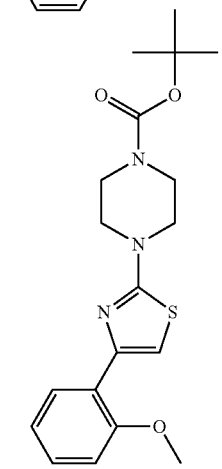

3

4
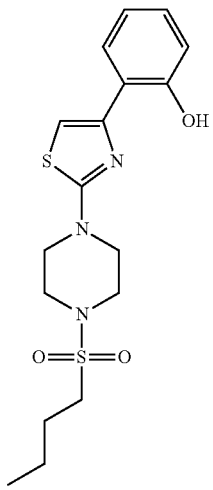
5
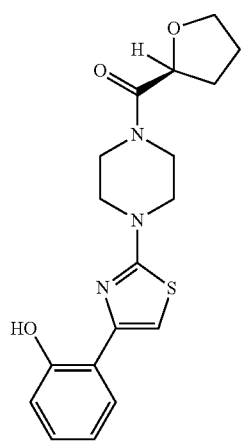
6
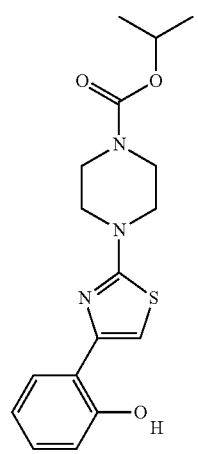
7
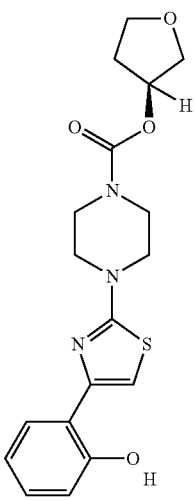
8
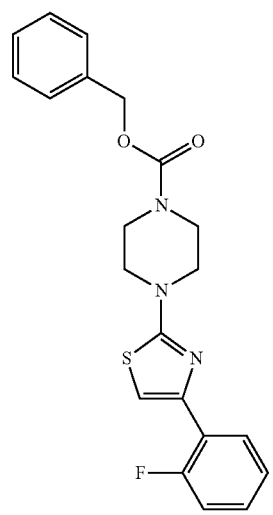
9

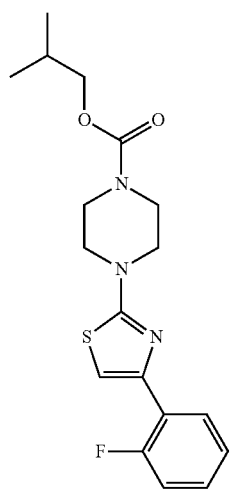
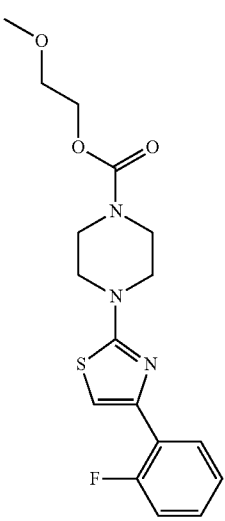
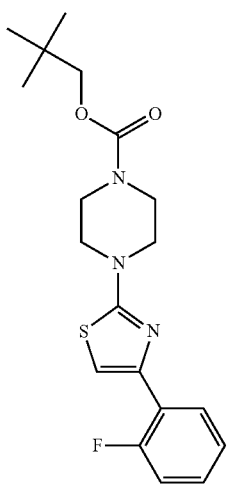
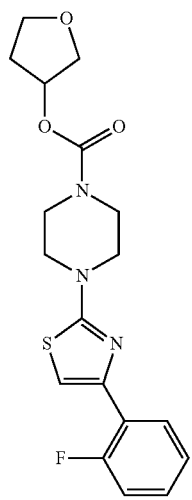
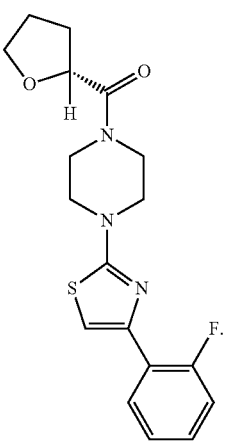
* * * * *